US010646329B2

(12) United States Patent
Zhao

(10) Patent No.: US 10,646,329 B2
(45) Date of Patent: May 12, 2020

(54) OPHTHALMIC APPARATUS WITH CORRECTIVE MERIDIANS HAVING EXTENDED TOLERANCE BAND

(71) Applicant: ABBOTT MEDICAL OPTICS INC., Santa Ana, CA (US)

(72) Inventor: Huawei Zhao, Irvine, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 0 days.

(21) Appl. No.: 15/467,963

(22) Filed: Mar. 23, 2017

(65) Prior Publication Data

US 2017/0273781 A1 Sep. 28, 2017

Related U.S. Application Data

(60) Provisional application No. 62/312,321, filed on Mar. 23, 2016, provisional application No. 62/312,338, (Continued)

(51) Int. Cl.
*A61F 2/16* (2006.01)
*A61B 3/00* (2006.01)
(Continued)

(52) U.S. Cl.
CPC .......... *A61F 2/1645* (2015.04); *A61B 3/0025* (2013.01); *A61F 2/1613* (2013.01);
(Continued)

(58) Field of Classification Search
CPC .................... A61F 2/1645; G02C 2202/02
See application file for complete search history.

(56) References Cited

U.S. PATENT DOCUMENTS 2,077,092 A 4/1937 Broder
3,305,294 A 2/1967 Alvarez
(Continued)

FOREIGN PATENT DOCUMENTS

CN 1035363 A 9/1989
CN 1039487 A 2/1990
(Continued)

OTHER PUBLICATIONS

Abelman H., et al. "Tolerance and Nature of Residual Refraction in Symmetric Power Space as Principal Lens Powers and Meridians Change," Computational and Mathematical Methods in Medicine, 2014, vol. 2014, pp. 1-12.
(Continued)

*Primary Examiner* — David H Willse
*Assistant Examiner* — Javier G Blanco
(74) *Attorney, Agent, or Firm* — Johnson & Johnson Surgical Vision, Inc.

(57) ABSTRACT

The embodiments disclosed herein include improved toric lenses and other ophthalmic apparatuses (including, for example, contact lens, intraocular lenses (IOLs), and the like) and associated method for their design and use. In an embodiment, an ophthalmic apparatus (e.g., a toric lens) includes one or more angularly-varying phase members comprising a diffractive or refractive structure, each varying the depths of focus of the apparatus so as to provide an extended tolerance to misalignment of the apparatus when implanted in an eye. That is, the ophthalmic apparatus establishes an extended band of operational meridian over the intended correction meridian.

20 Claims, 36 Drawing Sheets

Related U.S. Application Data filed on Mar. 23, 2016, provisional application No. 62/363,428, filed on Jul. 18, 2016.

(51) Int. Cl.
| | |
|---|---|
| *G02C 7/00* | (2006.01) |
| *G02C 7/04* | (2006.01) |
| *G02B 27/00* | (2006.01) |
| *G06F 7/548* | (2006.01) |
| *G06F 17/50* | (2006.01) |
| *G02C 7/06* | (2006.01) |
| *A61B 3/036* | (2006.01) |

(52) U.S. Cl.
CPC .......... *A61F 2/1624* (2013.01); *A61F 2/1654* (2013.01); *G02B 27/0012* (2013.01); *G02C 7/00* (2013.01); *G02C 7/042* (2013.01); *G02C 7/06* (2013.01); *G06F 7/548* (2013.01); *G06F 17/50* (2013.01); *A61B 3/036* (2013.01); *G02B 27/0075* (2013.01); *G02C 2202/02* (2013.01); *G02C 2202/10* (2013.01); *G02C 2202/20* (2013.01); *G02C 2202/22* (2013.01)

(56) References Cited

U.S. PATENT DOCUMENTS

| | | | |
|---|---|---|---|
| 3,367,734 A | 2/1968 | Karl et al. | |
| 3,735,685 A | 5/1973 | Plummer | |
| 4,010,496 A | 3/1977 | Neefe | |
| 4,056,311 A * | 11/1977 | Winthrop | G02C 7/061 351/159.42 |
| 4,162,122 A | 7/1979 | Cohen | |
| 4,210,391 A | 7/1980 | Cohen et al. | |
| 4,319,564 A | 3/1982 | Karickhoff | |
| 4,338,005 A | 7/1982 | Cohen | |
| 4,340,283 A | 7/1982 | Cohen et al. | |
| 4,370,760 A | 2/1983 | Kelman | |
| 4,377,873 A | 3/1983 | Reichert | |
| 4,402,579 A | 9/1983 | Poler | |
| 4,403,353 A | 9/1983 | Tennant | |
| 4,404,694 A | 9/1983 | Kelman | |
| 4,409,691 A | 10/1983 | Levy | |
| 4,424,597 A | 1/1984 | Schlegel | |
| 4,446,581 A | 5/1984 | Blake | |
| 4,480,340 A | 11/1984 | Shepard | |
| 4,500,382 A | 2/1985 | Foster | |
| 4,504,982 A | 3/1985 | Burk | |
| 4,551,864 A | 11/1985 | Akhavi | |
| 4,556,998 A | 12/1985 | Siepser | |
| 4,560,383 A | 12/1985 | Leiske | |
| 4,593,981 A | 6/1986 | Scilipoti | |
| 4,605,409 A | 8/1986 | Kelman | |
| 4,605,411 A | 8/1986 | Fedorov et al. | |
| 4,629,460 A | 12/1986 | Dyer | |
| 4,629,462 A | 12/1986 | Feaster | |
| 4,636,049 A | 1/1987 | Blaker | |
| 4,637,697 A | 1/1987 | Freeman | |
| 4,642,112 A | 2/1987 | Freeman | |
| 4,655,565 A | 4/1987 | Freeman | |
| 4,673,406 A | 6/1987 | Schlegel | |
| 4,676,791 A | 6/1987 | Lemaster et al. | |
| 4,676,792 A | 6/1987 | Praeger | |
| 4,681,102 A | 7/1987 | Bartell | |
| 4,687,484 A | 8/1987 | Kaplan | |
| 4,687,485 A | 8/1987 | Lim et al. | |
| RE32,525 E | 10/1987 | Pannu | |
| 4,725,277 A | 2/1988 | Bissonette | |
| 4,734,095 A | 3/1988 | Siepser | |
| 4,778,462 A | 10/1988 | Grendahl | |
| 4,781,717 A | 11/1988 | Grendahl | |
| 4,787,903 A | 11/1988 | Grendahl | |
| 4,787,904 A | 11/1988 | Severin et al. | |
| 4,795,462 A | 1/1989 | Grendahl | |
| 4,798,608 A | 1/1989 | Grendahl | |
| 4,798,609 A | 1/1989 | Grendahl | |
| 4,828,558 A | 5/1989 | Kelman | |
| 4,834,748 A | 5/1989 | McDonald | |
| 4,863,539 A | 9/1989 | Lee et al. | |
| 4,898,461 A | 2/1990 | Portney | |
| 4,932,970 A | 6/1990 | Portney | |
| 4,995,714 A | 2/1991 | Cohen | |
| 4,995,715 A | 2/1991 | Cohen | |
| 4,997,442 A | 3/1991 | Barrett | |
| 5,016,977 A | 5/1991 | Baude et al. | |
| 5,019,097 A | 5/1991 | Knight et al. | |
| 5,047,052 A | 9/1991 | Dubroff | |
| 5,054,905 A | 10/1991 | Cohen | |
| 5,056,908 A | 10/1991 | Cohen | |
| 5,066,301 A | 11/1991 | Wiley | |
| 5,071,432 A | 12/1991 | Baikoff | |
| 5,078,742 A | 1/1992 | Dahan | |
| 5,089,023 A | 2/1992 | Swanson | |
| 5,096,285 A | 3/1992 | Silberman | |
| 5,114,220 A | 5/1992 | Baude et al. | |
| 5,117,306 A | 5/1992 | Cohen | |
| 5,120,120 A | 6/1992 | Cohen | |
| 5,121,979 A | 6/1992 | Cohen | |
| 5,121,980 A | 6/1992 | Cohen | |
| 5,133,749 A | 7/1992 | Nordan | |
| 5,144,483 A | 9/1992 | Cohen | |
| 5,147,395 A | 9/1992 | Willis | |
| 5,147,397 A | 9/1992 | Christ et al. | |
| 5,173,723 A * | 12/1992 | Volk | A61F 2/1613 351/159.47 |
| 5,184,405 A | 2/1993 | Cress | |
| 5,197,981 A | 3/1993 | Southard | |
| 5,201,763 A | 4/1993 | Brady et al. | |
| 5,203,790 A | 4/1993 | McDonald | |
| 5,217,491 A | 6/1993 | Vanderbilt | |
| 5,225,858 A | 7/1993 | Portney | |
| 5,225,997 A | 7/1993 | Lederer et al. | |
| 5,229,797 A | 7/1993 | Futhey et al. | |
| 5,258,025 A | 11/1993 | Fedorov et al. | |
| 5,278,592 A | 1/1994 | Marie et al. | |
| 5,408,281 A | 4/1995 | Zhang | |
| 5,433,745 A | 7/1995 | Graham et al. | |
| 5,476,513 A | 12/1995 | Brady et al. | |
| 5,479,220 A | 12/1995 | Komatsu et al. | |
| 5,567,365 A | 10/1996 | Weinschenk, III et al. | |
| 5,571,177 A | 11/1996 | Deacon et al. | |
| 5,620,720 A | 4/1997 | Glick et al. | |
| 5,628,796 A | 5/1997 | Suzuki | |
| 5,652,638 A | 7/1997 | Roffman et al. | |
| 5,691,800 A | 11/1997 | Iki et al. | |
| 5,699,142 A | 12/1997 | Lee et al. | |
| 5,716,403 A | 2/1998 | Tran et al. | |
| 5,748,282 A | 5/1998 | Freeman | |
| 5,760,871 A | 6/1998 | Kosoburd et al. | |
| 5,796,462 A * | 8/1998 | Roffman | A61F 2/1613 351/159.21 |
| 5,801,807 A | 9/1998 | Satake et al. | |
| 5,928,282 A | 7/1999 | Nigam | |
| 5,968,094 A | 10/1999 | Werblin et al. | |
| 6,015,435 A | 1/2000 | Valunin et al. | |
| 6,051,024 A | 4/2000 | Cumming | |
| 6,055,111 A | 4/2000 | Nomura et al. | |
| 6,126,283 A | 10/2000 | Wen et al. | |
| 6,126,286 A | 10/2000 | Portney | |
| 6,129,759 A | 10/2000 | Chambers | |
| 6,142,625 A | 11/2000 | Sawano et al. | |
| 6,179,870 B1 | 1/2001 | Sourdille et al. | |
| 6,210,005 B1 | 4/2001 | Portney | |
| 6,235,055 B1 | 5/2001 | Chu | |
| 6,261,321 B1 | 7/2001 | Kellan | |
| 6,286,956 B1 | 9/2001 | Oyama et al. | |
| 6,319,282 B1 | 11/2001 | Nishi | |
| 6,338,559 B1 | 1/2002 | Williams et al. | |
| 6,419,697 B1 | 7/2002 | Kelman | |
| 6,457,826 B1 | 10/2002 | Lett | |
| 6,464,355 B1 | 10/2002 | Gil | |
| 6,474,814 B1 | 11/2002 | Griffin | |
| 6,488,708 B2 | 12/2002 | Sarfarazi | |
| 6,491,721 B2 | 12/2002 | Freeman et al. | |

(56) References Cited

U.S. PATENT DOCUMENTS

| | | |
|---|---|---|
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,554,859 B1 | 4/2003 | Lang et al. |
| 6,557,992 B1 | 5/2003 | Dwyer et al. |
| 6,598,606 B2 | 7/2003 | Terwee et al. |
| 6,609,793 B2 | 8/2003 | Norrby et al. |
| 6,705,729 B2 | 3/2004 | Piers et al. |
| 6,709,102 B2 | 3/2004 | Duppstadt |
| 6,802,605 B2 | 10/2004 | Cox et al. |
| 6,808,262 B2 | 10/2004 | Chapoy et al. |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,899,425 B2 | 5/2005 | Roffman et al. |
| 6,923,539 B2 | 8/2005 | Simpson et al. |
| 6,923,540 B2 | 8/2005 | Ye et al. |
| 6,986,578 B2 | 1/2006 | Jones |
| 7,036,931 B2 | 5/2006 | Lindacher et al. |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,188,949 B2 | 3/2007 | Bandhauer et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,425,068 B2 | 9/2008 | Koest |
| 7,441,894 B2 | 10/2008 | Zhang et al. |
| 7,455,404 B2 | 11/2008 | Bandhauer et al. |
| 7,455,407 B2 | 11/2008 | Neal et al. |
| 7,475,986 B2 | 1/2009 | Dai et al. |
| 7,615,073 B2 | 11/2009 | Deacon et al. |
| 7,616,330 B2 | 11/2009 | Neal et al. |
| 7,713,299 B2 | 5/2010 | Brady et al. |
| 7,794,497 B2 | 9/2010 | Brady et al. |
| 7,857,451 B2 | 12/2010 | Thibos et al. |
| 7,871,162 B2 | 1/2011 | Weeber |
| 7,993,398 B2 | 8/2011 | Deacon et al. |
| 8,241,354 B2 | 8/2012 | Hong et al. |
| 8,740,382 B1 | 6/2014 | Liu et al. |
| 8,764,822 B2 | 7/2014 | Harris et al. |
| 8,862,447 B2 | 10/2014 | Weeber |
| 9,241,627 B2 | 1/2016 | Steinmueller |
| 9,393,108 B2 | 7/2016 | Canovas Vidal et al. |
| 9,491,431 B2 | 11/2016 | Zhou |
| 2001/0051825 A1 | 12/2001 | Peterson |
| 2002/0118337 A1 | 8/2002 | Perrott et al. |
| 2002/0173846 A1 | 11/2002 | Blake et al. |
| 2002/0196408 A1 | 12/2002 | Bhalakia et al. |
| 2002/0196412 A1 | 12/2002 | Abitbol |
| 2003/0076478 A1 | 4/2003 | Cox |
| 2003/0171808 A1 | 9/2003 | Phillips |
| 2004/0021824 A1 | 2/2004 | Ye et al. |
| 2004/0021825 A1 | 2/2004 | Richardson |
| 2004/0054358 A1 | 3/2004 | Cox |
| 2004/0068317 A1 | 4/2004 | Knight |
| 2004/0080710 A1 | 4/2004 | Wooley et al. |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150789 A1 | 8/2004 | Jones |
| 2004/0150790 A1 | 8/2004 | Roffman et al. |
| 2004/0156014 A1 | 8/2004 | Piers et al. |
| 2004/0167622 A1 | 8/2004 | Sunalp et al. |
| 2005/0096226 A1 | 5/2005 | Stock et al. |
| 2005/0122474 A1 | 6/2005 | Koretz |
| 2005/0125056 A1 | 6/2005 | Deacon et al. |
| 2005/0128432 A1 | 6/2005 | Altmann |
| 2005/0203619 A1 | 9/2005 | Altmann |
| 2005/0251254 A1 | 11/2005 | Brady et al. |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0055877 A1 | 3/2006 | Yanari |
| 2006/0066808 A1 | 3/2006 | Blum et al. |
| 2006/0068453 A1 | 3/2006 | Altieri |
| 2006/0109421 A1 | 5/2006 | Ye et al. |
| 2006/0116763 A1 | 6/2006 | Simpson |
| 2006/0116764 A1 | 6/2006 | Simpson |
| 2006/0116765 A1 | 6/2006 | Blake et al. |
| 2006/0238702 A1 | 10/2006 | Glick et al. |
| 2006/0244904 A1 | 11/2006 | Hong et al. |
| 2006/0244916 A1 | 11/2006 | Guillon |
| 2006/0279700 A1 | 12/2006 | Liang |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0268453 A1 | 11/2007 | Hong et al. |
| 2008/0018910 A1 | 1/2008 | Neal et al. |
| 2008/0030677 A1 | 2/2008 | Simpson |
| 2008/0161914 A1 | 7/2008 | Brady et al. |
| 2008/0231809 A1 | 9/2008 | Haigis |
| 2008/0273169 A1 | 11/2008 | Blum et al. |
| 2008/0291393 A1 | 11/2008 | Menezes |
| 2009/0012609 A1 | 1/2009 | Geraghty et al. |
| 2009/0036980 A1 | 2/2009 | Norrby et al. |
| 2009/0051876 A1 | 2/2009 | Seiler et al. |
| 2009/0062911 A1 | 3/2009 | Bogaert |
| 2009/0088840 A1 | 4/2009 | Simpson et al. |
| 2009/0164008 A1 | 6/2009 | Hong et al. |
| 2009/0210054 A1 | 8/2009 | Weeber et al. |
| 2009/0234448 A1 | 9/2009 | Weeber et al. |
| 2009/0275929 A1 | 11/2009 | Zickler |
| 2009/0279048 A1 | 11/2009 | Hong et al. |
| 2009/0303465 A1 | 12/2009 | Clements et al. |
| 2009/0323020 A1 | 12/2009 | Zhao et al. |
| 2010/0016965 A1 | 1/2010 | Hong et al. |
| 2010/0082017 A1 | 4/2010 | Zickler et al. |
| 2010/0161048 A1 | 6/2010 | Schaper, Jr. |
| 2010/0220185 A1 | 9/2010 | Vertoprakhov et al. |
| 2010/0274234 A1 | 10/2010 | Liang |
| 2010/0315589 A1* | 12/2010 | Portney .............. A61F 2/1613 351/159.21 |
| 2011/0166652 A1 | 7/2011 | Bogaert et al. |
| 2011/0205486 A1 | 8/2011 | Zhao |
| 2012/0140166 A1 | 6/2012 | Zhao |
| 2012/0249955 A1 | 10/2012 | Sarver et al. |
| 2012/0310337 A1 | 12/2012 | Hacker et al. |
| 2012/0320334 A1 | 12/2012 | Ho et al. |
| 2013/0050637 A1 | 2/2013 | Roffman et al. |
| 2013/0307965 A1 | 11/2013 | Widman et al. |
| 2014/0016088 A1 | 1/2014 | De Rossi et al. |
| 2014/0135919 A1 | 5/2014 | Gontijo et al. |
| 2014/0160436 A1 | 6/2014 | Kasthurirangan et al. |
| 2014/0268042 A1 | 9/2014 | Bor et al. |
| 2014/0293426 A1 | 10/2014 | Dobschal |
| 2015/0062529 A1 | 3/2015 | Kasthurirangan et al. |
| 2015/0138350 A1 | 5/2015 | Videcoq |
| 2015/0250583 A1 | 9/2015 | Rosen et al. |
| 2015/0320547 A1 | 11/2015 | Rosen et al. |
| 2015/0359625 A1* | 12/2015 | Argal .................. A61F 2/1618 623/6.24 |
| 2015/0362746 A1* | 12/2015 | Skudder .............. G02C 7/022 351/159.22 |
| 2016/0157997 A1* | 6/2016 | Gerlach .............. A61F 2/1637 623/6.25 |
| 2016/0299355 A1* | 10/2016 | Biemold .............. G02C 7/04 |

FOREIGN PATENT DOCUMENTS

| | | |
|---|---|---|
| CN | 1406120 A | 3/2003 |
| CN | 1833192 A | 9/2006 |
| CN | 102099729 A | 6/2011 |
| DE | 8107675 U1 | 7/1981 |
| DE | 3439551 A1 | 4/1986 |
| DE | 102005022683 A1 | 11/2006 |
| EP | 226400 A2 | 6/1987 |

(56) References Cited

FOREIGN PATENT DOCUMENTS

| | | | |
|---|---|---|---|
| EP | 227357 | A2 | 7/1987 |
| EP | 0343067 | A1 | 11/1989 |
| EP | 0457553 | A2 | 11/1991 |
| EP | 681198 | A1 | 11/1995 |
| EP | 0926531 | A1 | 6/1999 |
| EP | 949529 | A2 | 10/1999 |
| EP | 957331 | A2 | 11/1999 |
| EP | 1424049 | A1 | 6/2004 |
| EP | 1310267 | B1 | 1/2008 |
| EP | 1424049 | B1 | 6/2009 |
| EP | 2182891 | B1 | 4/2014 |
| FR | 2745711 | A1 | 9/1997 |
| JP | H0255314 | A | 2/1990 |
| WO | 8603961 | A1 | 7/1986 |
| WO | 9109336 | A1 | 6/1991 |
| WO | 9222264 | A1 | 12/1992 |
| WO | 9303409 | A1 | 2/1993 |
| WO | 9507487 | A1 | 3/1995 |
| WO | 9856315 | A1 | 12/1998 |
| WO | 9905499 | A1 | 2/1999 |
| WO | 0019906 | A1 | 4/2000 |
| WO | 0111418 | A1 | 2/2001 |
| WO | 0135868 | A1 | 5/2001 |
| WO | 0154569 | A1 | 8/2001 |
| WO | 0163344 | A1 | 8/2001 |
| WO | 0182839 | A1 | 11/2001 |
| WO | 0189424 | A1 | 11/2001 |
| WO | 0221194 | A2 | 3/2002 |
| WO | 03009053 | A1 | 1/2003 |
| WO | 2004034129 | A1 | 4/2004 |
| WO | 2004090611 | A2 | 10/2004 |
| WO | 2004096014 | A2 | 11/2004 |
| WO | 05019906 | A1 | 3/2005 |
| WO | 06025726 | A1 | 3/2006 |
| WO | 2006032263 | A2 | 3/2006 |
| WO | 2006047698 | A1 | 5/2006 |
| WO | 06060477 | A2 | 6/2006 |
| WO | 2006060480 | A2 | 6/2006 |
| WO | 2007067872 | A2 | 6/2007 |
| WO | 2007092948 | A1 | 8/2007 |
| WO | 2007133384 | A2 | 11/2007 |
| WO | 2008045847 | A2 | 4/2008 |
| WO | 2008083283 | A2 | 7/2008 |
| WO | 2009020963 | A1 | 2/2009 |
| WO | 2009029515 | A1 | 3/2009 |
| WO | 2009076670 | A1 | 6/2009 |
| WO | 2009105567 | A1 | 8/2009 |
| WO | 2009137491 | A1 | 11/2009 |
| WO | 2010009254 | A1 | 1/2010 |
| WO | 2010009257 | A1 | 1/2010 |
| WO | 2012083143 | A1 | 6/2012 |
| WO | 2012085917 | A1 | 6/2012 |
| WO | 2012154597 | A1 | 11/2012 |
| WO | 2015022215 | A1 | 2/2015 |
| WO | 2016123167 | A1 | 8/2016 |

OTHER PUBLICATIONS

Baumeister M., et al., "Tilt and Decentration of Spherical and Aspheric Intraocular Lenses: Effect on Higher-Order Aberrations," Journal of Cataract & Refractive Surgery, 2009, vol. 35 (6), pp. 1006-1012.
Brown W.L., "Revisions to Tolerances in Cylinder Axis and in Progressive Addition Lens Power in ANSI Z80.1-2005," Optometry, 2006, vol. 77 (7), pp. 343-349.
Canovas C., et al., "Customized Eye Models for Determining Optimized Intraocular Lenses Power," Biomedical Optics Express, Jun. 1, 2011, vol. 2 (6), pp. 1649-1662.
International Search Report and Written Opinion for Application No. PCT/US2017/023772, dated Jul. 21, 2017, 14 pages.
International Search Report and Written Opinion for Application No. PCT/US2017/023864, dated Jul. 6, 2017, 15 pages.
International Search Report and Written Opinion for Application No. PCT/US2017/023888, dated Jul. 24, 2017, 14 pages.
International Search Report and Written Opinion for Application No. PCT/US2017/023897, dated Jul. 11, 2017, 17 pages.
Olsen T., "Simple Method to Calculate the Surgically Induced Refractive Change," Journal of Cataract & Refractive Surgery, Mar. 1993, vol. 19 (2), pp. 319-320.
International Search Report and Written Opinion for Application No. PCT/US2017/023836, dated Jun. 19, 2017, 12 pages.
International Search Report and Written Opinion for Application No. PCT/US2018/023946, dated Jun. 12, 2018, 16 pages.
Hill W., et al., "Monte Carlo Simulation of Expected Outcomes with the Acrysof Toric Intraocular Lens," BMC Ophthalmology, Oct. 2008, vol. 8, pp. 22.
International Preliminary Report on Patentability for Application No. PCT/US2017/023772, dated Oct. 4, 2018, 7 pages.
Mencucci R., et al., "Clinical outcomes and rotational stability of a 4-haptic toric intraocular lens in myopic eyes," Journal of Cataract & Refractive Surgery, Sep. 2014, vol. 40 (9), pp. 1479-1487.
Einighammer J., et al., "The Individual Virtual Eye: a Computer Model for Advanced Intraocular Lens Calculation, " Journal of optometry, Apr.-Jun. 2009, vol. 2 (2), pp. 70-82.
Gobin L., et al., "Spherotoric Bag-In-The-Lens Intraocular Lens: Power Calculation and Predictive Misalignment Nomogram, " Journal of Cataract & Refractive Surgery, Jun. 2011, vol. 37 (6), pp. 1020-1030.
Naeser K., "Assessment and Statistics of Surgically Induced Astigmatism, " Acta Ophthalmologica, May 2008, vol. 86 Suppl 1, pp. 5-28.
Narvaez J., et al., "Accuracy of Intraocular Lens Power Prediction Using the Hoffer Q, Holladay 1, Holladay 2, and SRK/T formulas, " Journal of Cataract & Refractive Surgery, Dec. 2006, vol. 32 (12), pp. 2050-2053.
Patel S., et al., "An Evaluation of Unexpected Refractive Outcomes Following Toric IOL Implantation for Astigmatism: A Sector Subtraction Graphical Method for Calculating the Effective Astigmatic Correction, " Research Gate, Jan. 2016, 90 Reads.
Alfonso J.F., et al., "Prospective Study of the Acri.LISA Bifocal Intraocular Lens," Journal of Cataract Refractive Surgery, Nov. 2007, vol. 33 (11), pp. 1930-1935.
Alio J.L., et al., "Phakic Anterior Chamber Lenses for the Correction of Myopia: A 7-Year Cumulative Analysis of Complications in 263 Cases," Ophthalmology, Mar. 1999, vol. 106 (3), pp. 458-466.
Apple D.J., et al., "Anterior Chamber Lenses Part 1: Complications and Pathology and a Review of Designs," Journal pf Cataract Refractive Surgery, Mar. 1987, vol. 13 (2), pp. 157-174.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 22 (36), pp. 205-221.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.
Baikoff G., et al., "Angle-fixated Anterior Chamber Phakic Intraocular Lens for Myopia 7 to -19 Diopters," Journal of Refractive Surgery, May-Jun. 1998, vol. 14 (3), pp. 282-292.
Canovas C., et al., "Hybrid Adaptive-Optics Visual Simulator," Optical Letters, Jan. 15, 2010, vol. 35 (2), pp. 196-198.
Cheng X., et al., "Predicting Subjective Judgment of Best Focus with Objective Image Quality Metrics," Journal of Vision, Apr. 2004, vol. 4 (4), pp. 310-321.
CILCO Advertisement Brochure, Oct. 1982, 3 pages.
Cohen A.L., "Practical Design of a Bifocal Hologram Contact Lens or Intraocular Lens," Applied Optics, Jul. 1, 1992, vol. 31 (19), pp. 3750-3754.
De Almeida M.S., et al., "Different Schematic Eyes and their Accuracy to the in Vivo Eye: A Quantitative Comparison Study," Brazilian Journal of Physics, Jun. 2007, vol. 37 (2A), 10 pages.
Diffractive Lenses for Extended Depth of Focus and Presbyopic Correction, Presentation from Wavefront Congress held on Feb. 15, 2008, Rochester, New York.
Doskolovich L.L., et al., "Special Diffractive Lenses," Lens and Optical Systems Design, Apr. 1992, vol. 1780, pp. 393-402.

(56) References Cited

OTHER PUBLICATIONS

Egger J.R., "Use of Fresnel Lenses in Optical Systems: Some Advantages and Limitations," in: Atomic and Vlolecular Spectroscopy, vol. 193, Paul R. Yoder, Jr., ed., SPIE Proceedings, the International Society for Optical Engineering, 1979, pp. 63-69.

Farberov, "Manufacturing Fresnel Lenses for Cameras," Soviet Journal of Optical Technology, 1983, vol. 50 (3), pp. 186-188.

Gupta P.A., "Theoretical Analysis of the Fresnel lens As a Function of Design Parameters," Applied Energy, 1981, vol. 9 (4), pp. 301-310.

Kim J.H., et al., "The Analysis of Predicted Capsular Bag Diameter using Modified Model of Capsule Measuring Ring in Asians," Clinical and Experimental Ophthalmology, Apr. 2008, vol. 36 (3), pp. 238-244.

Liou H.L. et al. "Anatomically Accurate, Finite Model Eye for Optical Modeling," Journal of Optical Society of America, Aug. 1997, vol. 14 (8), pp. 1684-1695.

Liou H.L., et al., "The Prediction of Spherical Aberration with Schematic Eyes," Ophthalmic and Physiological Optics, Jan. 1996, vol. 16 (4), pp. 348-354.

Marinho A., "Results are Encouraging for Phakic IOLs, but More Work is needed," Refractive Surgery, Feb. 2000, p. 12, 15.

Marsack J.D., et al., "Metrics of Optical Quality Derived from Wave Aberrations Predict Visual Performance," Journal of Vision, Apr. 2004, vol. 4 (4), pp. 322-328.

Menapace R., "The Capsular Tension Rings," Journal of Cataract & Refractive Surgery, Dec. 10, 2008, Chap. 3, pp. 27-44.

Monsoriu J.A., et al., "Devil's Lenses," Optics Express, Oct. 17, 2007, vol. 15 (21), pp. 13858-13864.

Navarro R., et al., "Accommodation-Dependent Model of the Human Eye with Aspherics," Journal of the Optical Society of America, Aug. 1985, vol. 2 (8), pp. 1273-1281.

Nio Y.K., et al., "Effect of Intraocular Lens Implantation on Visual Acuity, Contrast Sensitivity, and Depth of Focus," Journal of Cataract and Refractive Surgery, Nov. 2003, vol. 29 (11), pp. 2073-2081.

Norrby S., et al., "Model Eyes for Evaluation of Intraocular Lenses," Applied Optics, Sep. 7, 2007, vol. 46 (26), pp. 6595-6605.

Piers P.A., et al., "Eye Models for the Prediction of Contrast Vision in Patients with New Intraocular Lens Designs," optics Letters, Apr. 1, 2004, vol. 29 (7), pp. 733-735.

Piers P.A., et al., "Theoretical Comparison of Aberration-Correcting Customized and Aspheric Intraocular Lenses," Journal of Refractive Surgery, Apr. 2007, vol. 23 (4), pp. 374-384.

Praeger D.L, "Praeger Technique for the Insertion of the Copeland Radial IOL Posterior Chamber Placement," aopeland Lens, 1982, 7 pages.

Siedlecki D., et al., "Radial Gradient index Intraocular Lens: a Theoretical Model," Journal of Modern Optics, Feb. 20, 2008-Mar. 10, 2008, vol. 55 (4-5), pp. 639-647.

Strenn K., et al., "Capsular bag Shrinkage after Implantation of an Open-Loop Silicone Lens and a Poly(methyl methacrylate) Capsule Tension Ring," Journal of Cataract and Refractive Surgery, Dec. 1997, vol. 23 (10), pp. 1543-1547.

Tehrani M., et al., "Capsule Measuring Ring to Predict Capsular Bag Diameter and Follow its Course after Foldable Intraocular Lens Implantation," Journal of Cataract Refractive Surgery, Nov. 2003, vol. 29 (11), pp. 2127-2134.

Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.

Van Den Berg T.J., "Analysis of Intraocular Straylight, Especially in Relation to Age," Optometry and Vision Science Feb. 1995, vol. 72 (2), pp. 52-59.

Van Meeteren A., "Calculations on the Optical Modulation Transfer Function of the Human Eye for White Light," Optica Acta, May 1974, vol. 21 (5), pp. 395-412.

Vanderwerf D., et al., "Approximating the Fresnel Lens," Electro Optical Systems Design, 1982, pp. 47-52.

Vass C., et al., "Prediction of Pseudophakic Capsular bag Diameter based on Biometric Variables," Journal of Cataract and Refractive Surgery, Oct. 1999, vol. 25 (10), pp. 1376-1381.

Villegas E.A., et al., "Correlation between Optical and Psychophy, Sical Parameters as a Function of Defocus," Optometry and Vision Science, Jan. 1, 2002, vol. 79 (1), pp. 60-67.

\* cited by examiner

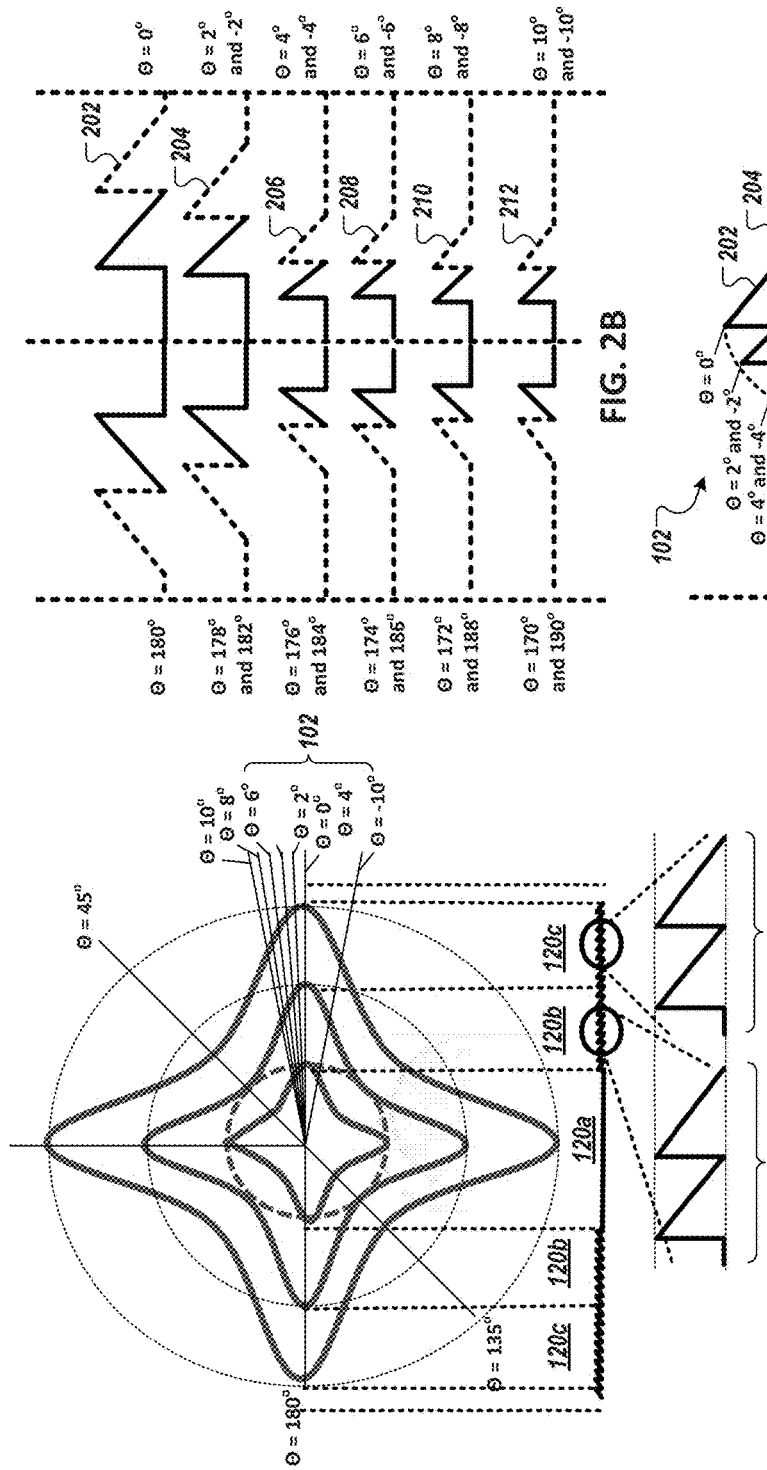
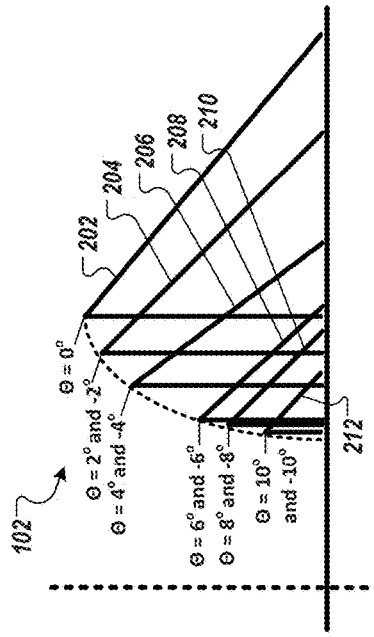
FIG. 2A
FIG. 2B
FIG. 2C

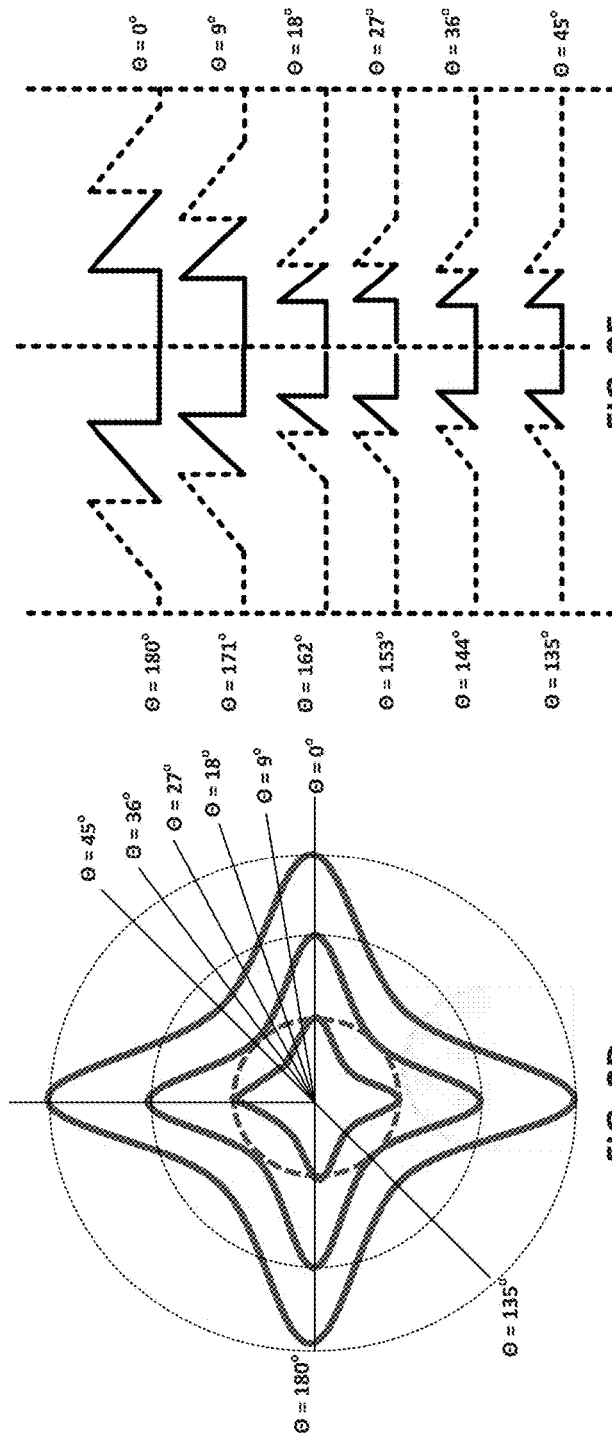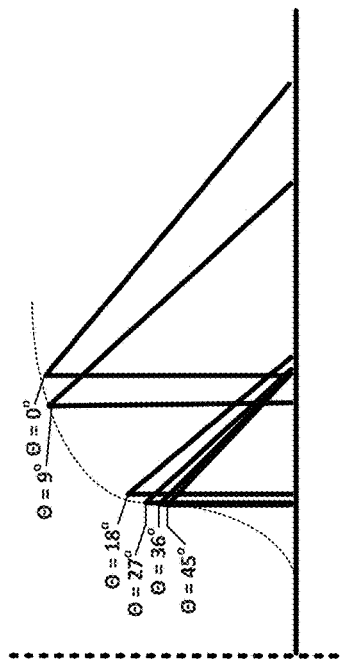

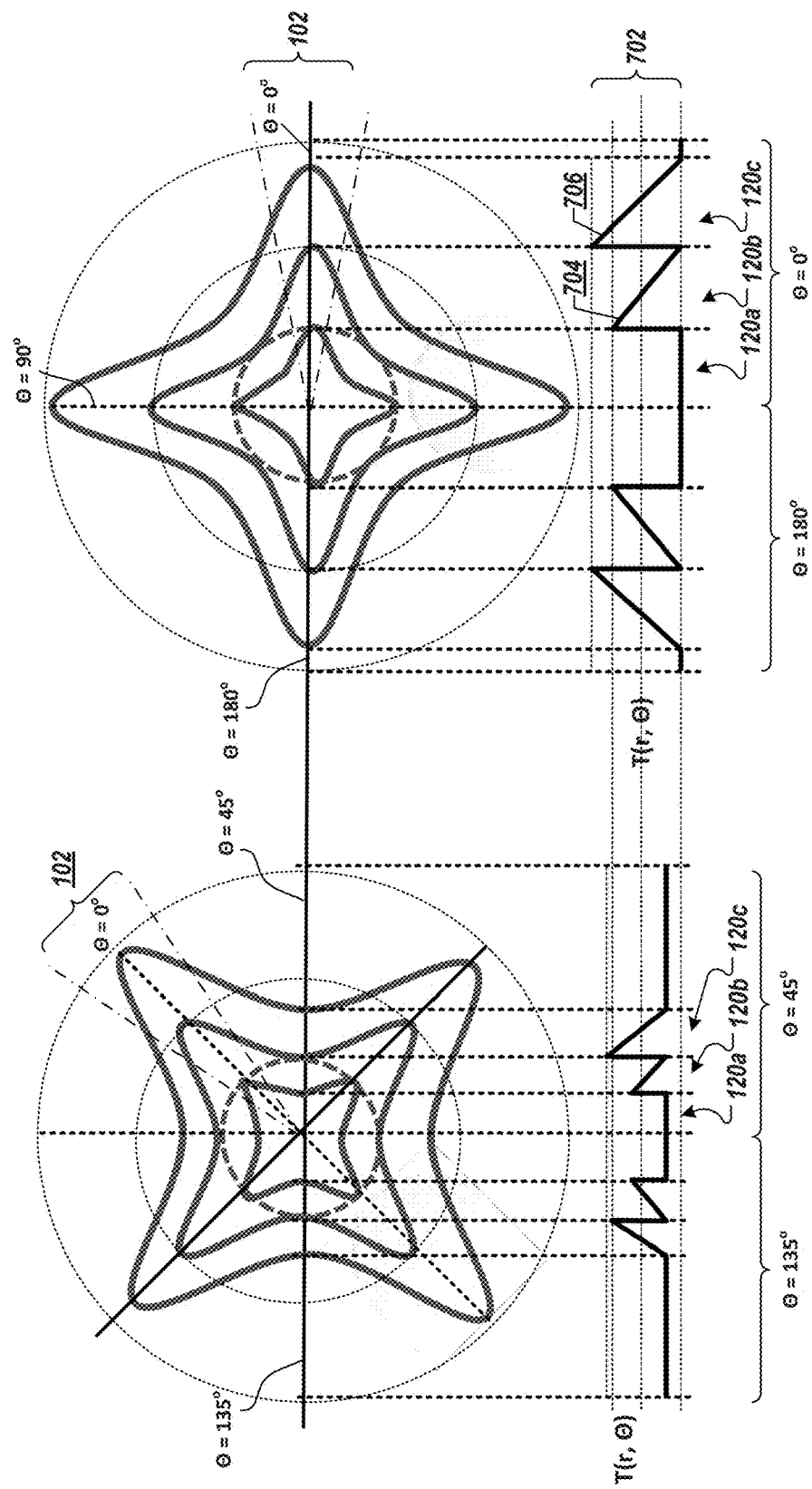

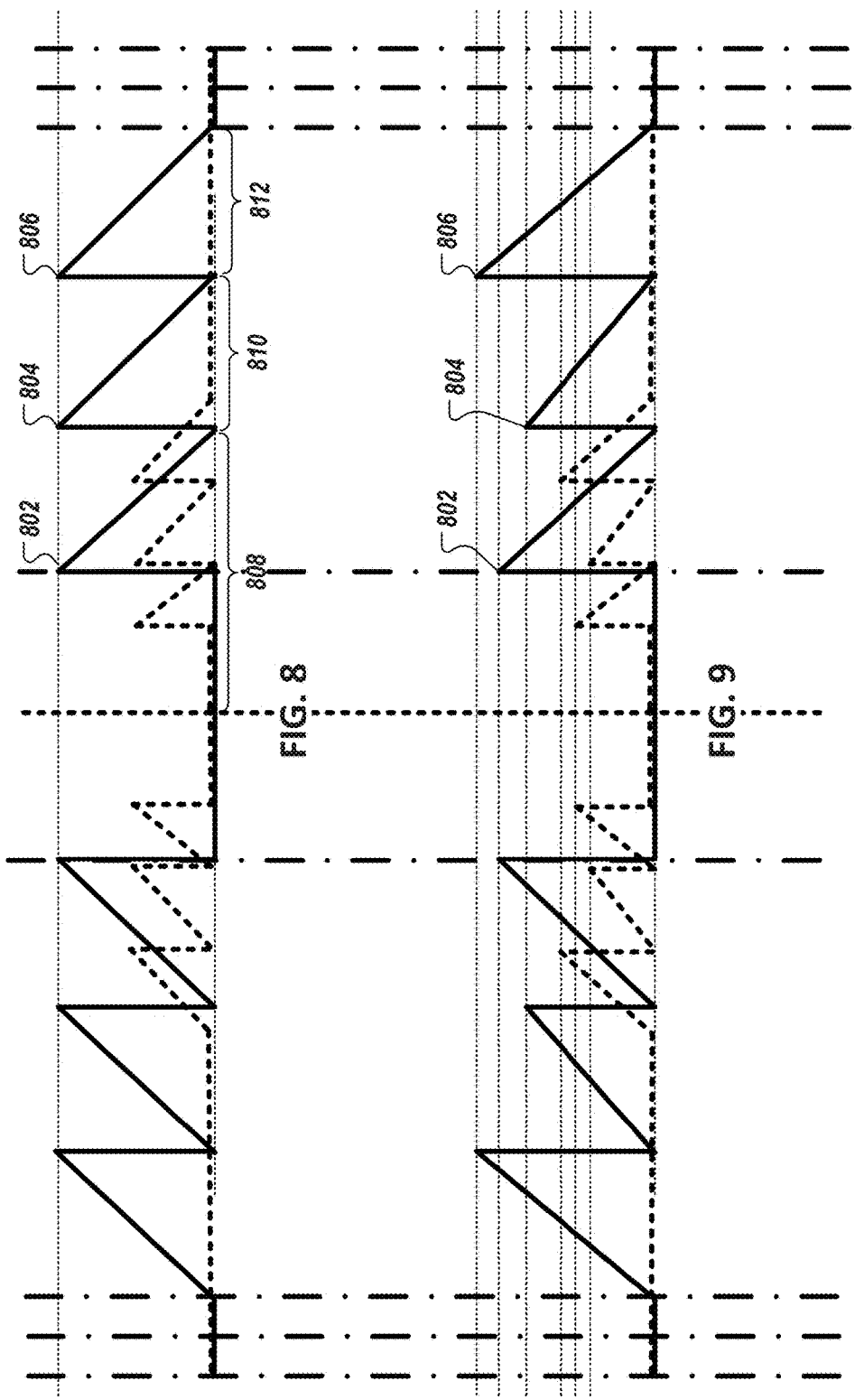

| Trifocal design example, in each foci Efficiency (%) | | | | |
|---|---|---|---|---|
| Meridian | foci0 | Foci0 + add1 | foci0 – add2 | Chromatic aberration |
| 0 | 100 | 0 | 0 | reduced |
| ±45 | 50 | 25 | 25 | reduced |
| ±90 | 100 | 0 | 0 | reduced |
| ±135 | 50 | 25 | 25 | reduced |
| 180 | 100 | 0 | 0 | reduced |

FIG. 14

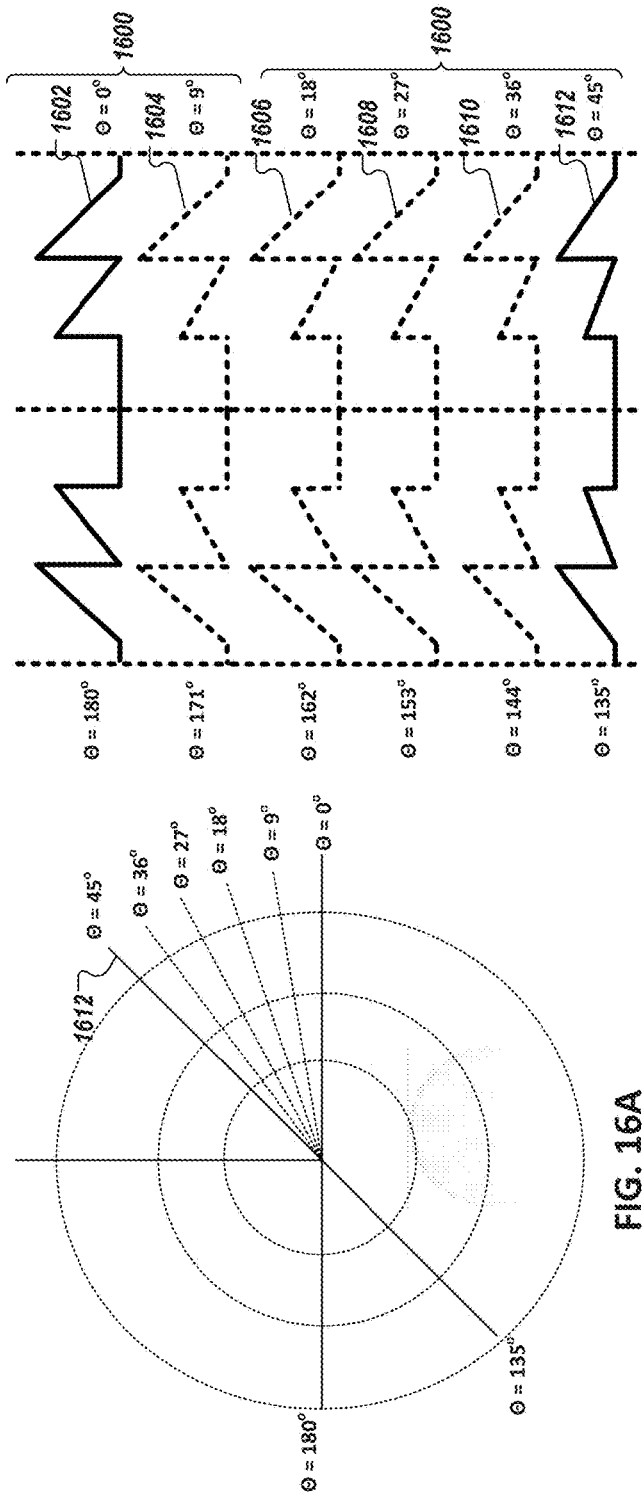
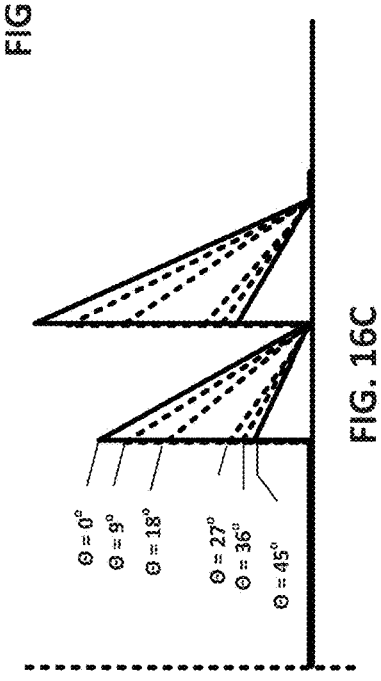
FIG. 16A
FIG. 16B
FIG. 16C

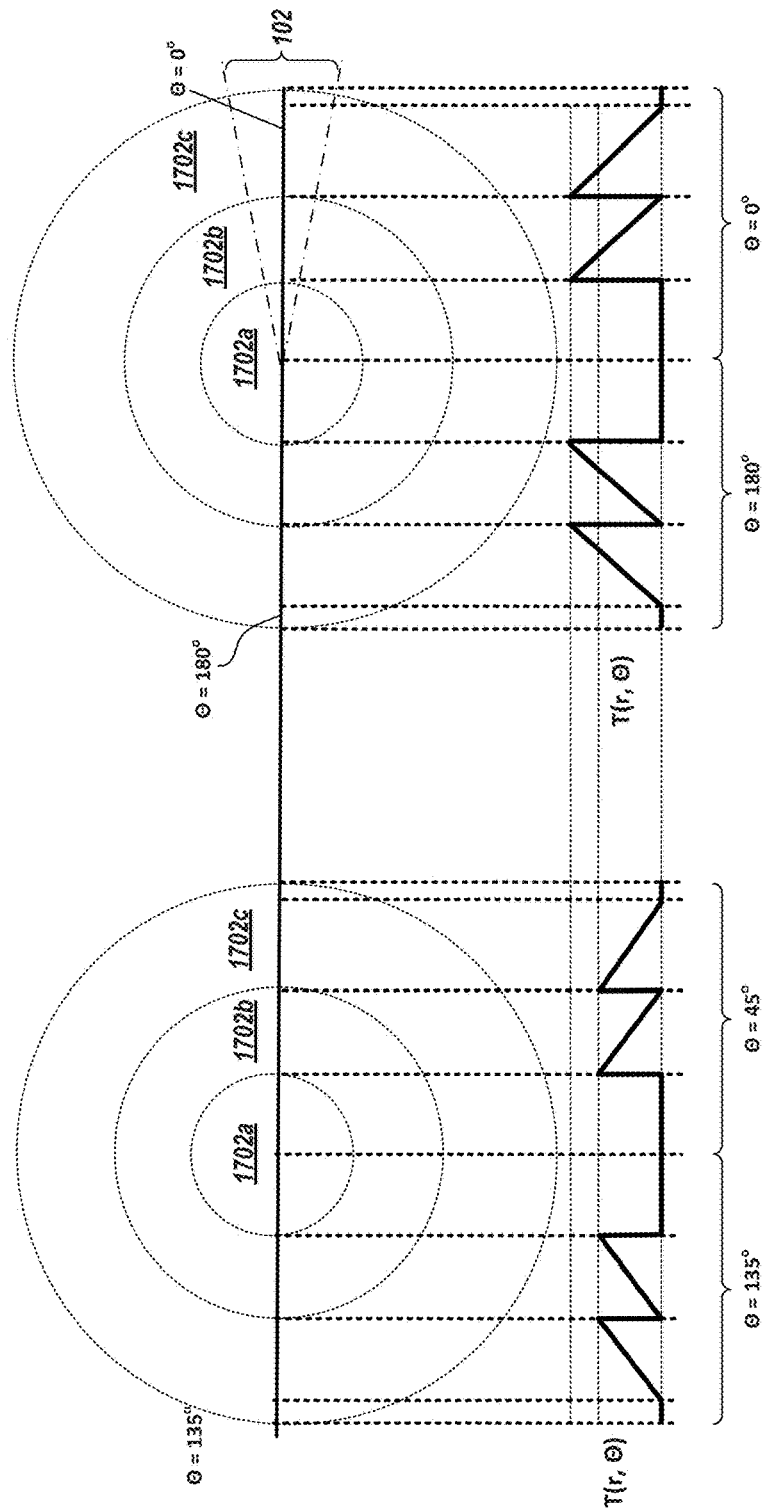

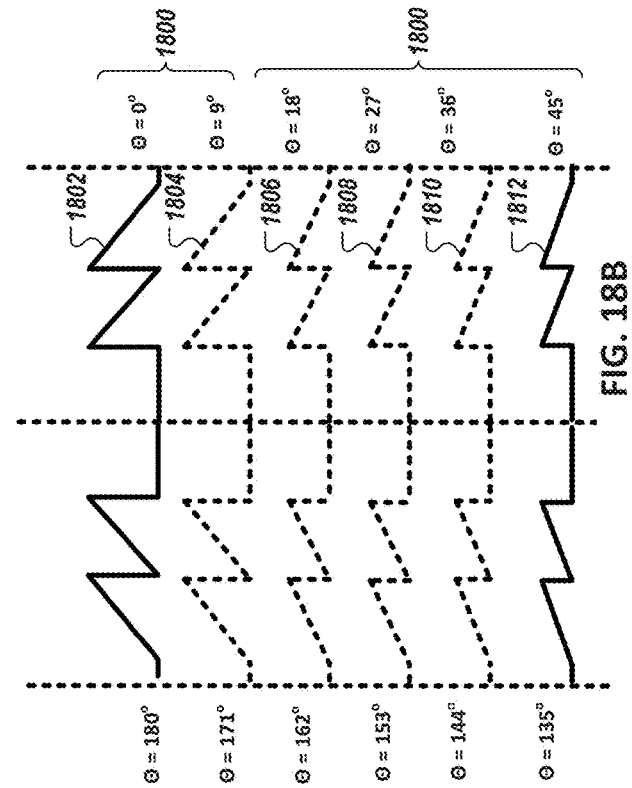
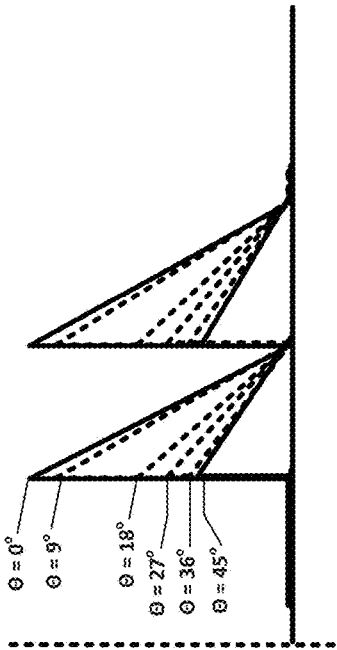
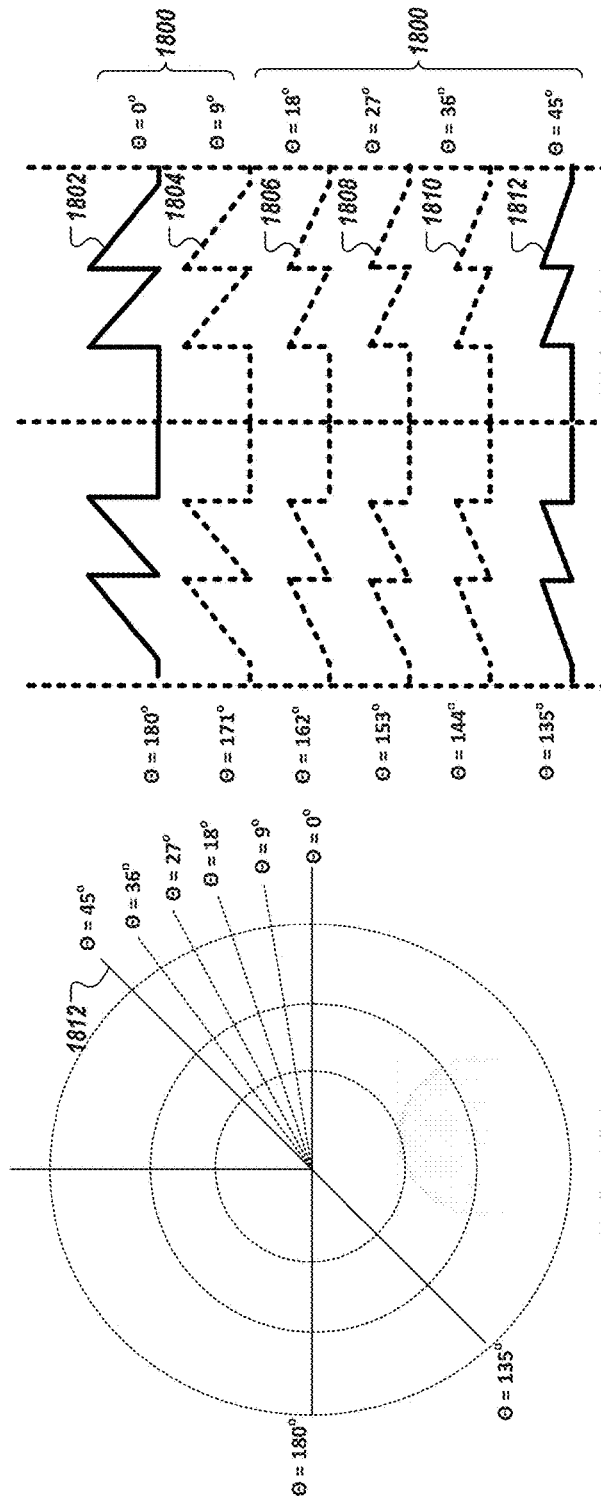

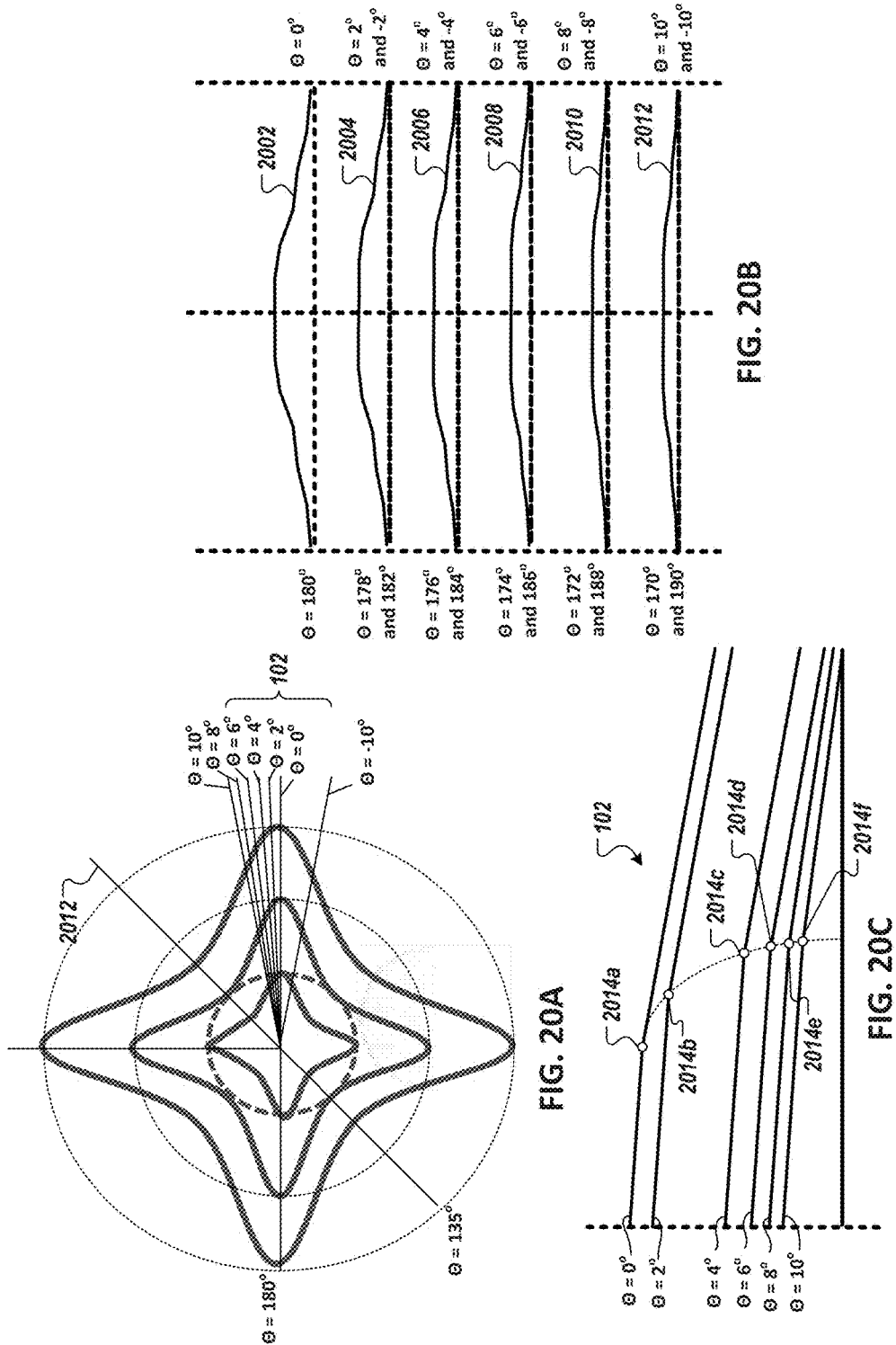

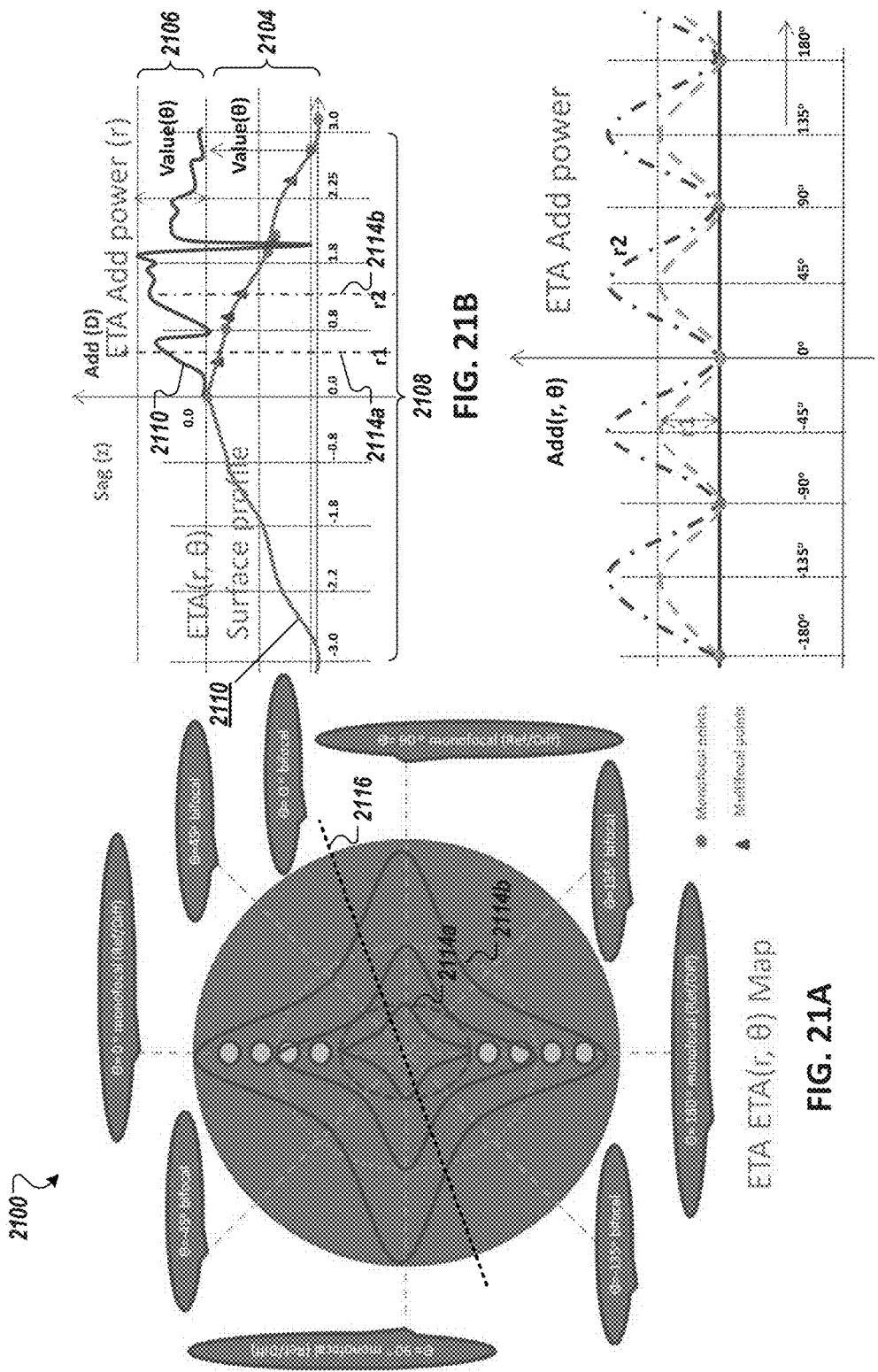

OPHTHALMIC APPARATUS WITH CORRECTIVE MERIDIANS HAVING EXTENDED TOLERANCE BAND

RELATED APPLICATIONS

This application claims priority to, and the benefit of, U.S. Provisional Appl. No. 62/312,321, filed Mar. 23, 2016; U.S. Provisional Appl. No. 62/312,338, filed Mar. 23, 2016; and 62/363,428, filed Jul. 18, 2016, each of which is incorporated by reference herein in its entirety.

TECHNICAL FIELD

This application is directed to lenses for correcting astigmatism, including providing increased tolerance for lens placement during implantation.

BACKGROUND

Ophthalmic lenses, such as spectacles, contact lenses and intraocular lenses, may be configured to provide both spherical and cylinder power. The cylinder power of a lens is used to correct the rotational asymmetric aberration of astigmatism of the cornea or eye, since astigmatism cannot be corrected by adjusting the spherical power of the lens alone. Lenses that are configured to correct astigmatism are commonly referred to as toric lenses. As used herein, a toric lens is characterized by a base spherical power (which may be positive, negative, or zero) and a cylinder power that is added to the base spherical power of the lens for correcting astigmatism of the eye.

Toric lenses typically have at least one surface that can be described by an asymmetric toric shape having two different curvature values in two orthogonal axes, wherein the toric lens is characterized by a "low power meridian" with a constant power equal to the base spherical power and an orthogonal "high power meridian" with a constant power equal to the base spherical power plus the cylinder power of the lens. Intraocular lenses, which are used to replace or supplement the natural lens of an eye, may also be configured to have a cylinder power for reducing or correcting astigmatism of the cornea or eye.

Existing toric lenses are designed to correct astigmatic effects by providing maximum cylindrical power that precisely matches the cylinder axis. Haptics are used to anchor an intraocular lens to maintain the lenses at a desired orientation once implanted in the eye. However, existing toric lenses themselves are not designed to account for misalignment of the lens that may occur during the surgical implantation of the lens in the eye or to account for unintended post-surgical movement of the lens in the eye.

Accordingly, it would be desirable to have intraocular lenses that are tolerant to misalignments.

SUMMARY

The embodiments disclosed herein include improved toric lenses and other ophthalmic apparatuses (including, for example, contact lens, intraocular lenses (IOLs), and the like) and associated method for their design and use. In an embodiment, an ophthalmic apparatus (e.g., a toric lens) includes one or more angularly-varying phase members comprising a diffractive or refractive structure, each varying the depths of focus of the apparatus so as to provide an extended tolerance to misalignment of the apparatus when implanted in an eye. That is, the ophthalmic apparatus establishes a band of operational meridian over the intended correction meridian.

Several embodiments of ophthalmic apparatus with extended tolerance astigmatism features are disclosed, each configured to establish the extended band of operational meridian.

In an aspect, an ophthalmic apparatus is disclosed. The ophthalmic apparatus includes an angularly-varying phase member configured to direct light, at a first meridian, to a first point of focus, wherein at angular positions nearby to the first meridian, the angularly-varying phase member is configured to direct light to points of focus nearby to the first point of focus such that rotational offsets of the angularly-varying phase member from the first meridian directs light from the nearby points of focus to the first point of focus, thereby establishing an extended band of operational meridian.

In some embodiments, the ophthalmic apparatus includes a multi-zonal lens body having a plurality of optical zones, wherein the multi-zonal lens body forms the angularly-varying phase member, wherein a height profile T1(r, θ) for each meridian θ is defined as: $T1(r, \theta) = t_1(r)|\cos 2(\theta)| + t_2(r)|\sin 2(\theta)|$, where $t_1(r)$ and $t_2(r)$ are the added power for each zone.

In some embodiments, the angularly-varying phase member and other angularly-varying phase members of the apparatus, collectively, forms a butterfly pattern.

In some embodiments, the multi-zonal lens body includes at least four optical zones, the at least four optical zones forming an angularly varying efficiency quadric optics (e.g., wherein the angularly varying efficiency trifocal optics comprises a first angularly varying phase member, e.g., a first refractive angularly varying phase member, at the first meridian; a second angularly varying phase member, e.g., a second refractive angularly varying phase member, at a second meridian; a third angularly varying phase member, e.g., a third refractive angularly varying phase member, at a third meridian; and a fourth refractive angularly varying phase member, e.g., a fourth refractive angularly varying phase member, at a fourth meridian).

In some embodiments, the angularly-varying phase members, collectively, form a butterfly pattern that is expressed as $$r(\theta) = \sqrt{2 \cdot n \cdot \frac{s(\theta) \cdot \lambda}{A(\theta)}},$$

where r(θ) is the contour radius for the given meridian added power A(θ), wavelength λ, zone number n, and the scaling value s(θ), all at meridian θ.

In some embodiments, the angularly phase member spans an optical zone defined by a polynomial-based surface coincident at a plurality of meridians having distinct cylinder powers, wherein each of the plurality of meridians is uniformly arranged on the optical zone for a same given added diopter of power up to 1.0D.

In some embodiments, differences among each continuously uniformly distributed contour line, at a given IOL plane, associated with a given meridian of the plurality of meridians is less than about 0.6D (diopters).

In some embodiments, the polynomial-based surface is characterized by a series of weighted cosine-based functions.

In some embodiments, the angularly phase member spans an optical zone defined by a freeform-polynomial surface area (e.g., as area having one or more refractive surfaces) coincident with one or more distinct cylinder powers, wherein the freeform-polynomial surface area is defined as a mathematical expression comprising a combination of one or more polynomial expressions (e.g., Chebyshev-based polynomial expression, Zernike-based polynomial expression, etc.) each having a distinct complex orders.

In some embodiments, at least one of the one or more polynomial expressions are selected from the group consisting of a Chebyshev polynomial and a Zernike polynomial.

In some embodiments, the freeform-polynomial surface area establishes the extended band of operational meridian across a range selected from the group consisting of about ±4 degrees, about ±5 degrees, about ±6 degrees, about ±7 degrees, about ±8 degrees, about ±9 degrees, about ±10 degrees, about ±11 degrees, about ±12 degrees, about ±13, degrees, about ±14 degrees, and about ±15 degrees.

In some embodiments, the freeform-polynomial surface area has a second height profile T(x,y) (e.g., an extra height profile having an associated cylinder power) on a first base height profile (e.g., a base or typical aspheric height profile), the second height profile being defined as:

$$T(x,y) = \Sigma \{c(i,j) * \cos(i * \arccos(t)) * \cos(j * \arccos(t))\}$$

where c(i, j) is a coefficient based on i and j, which are each integers (e.g., having a range between 0 and 10), x and y are spatial locations on the freeform-polynomial surface area, and t is a normalized parameter having values between −1.0 and 1.0.

In some embodiments, the optical zone is one of a plurality of optical zones, including a second optical zone, wherein the second optical zone is defined by a second freeform-polynomial surface region characterized and defined by a second polynomial, wherein the second freeform-polynomial surface area has a third height profile $T_2(x,y)$ (e.g., an extra height profile associated with cylinder power) superimposed on a first height profile (e.g. a base or typical aspheric height profile), the third height profile being defined as:

$$T_2(x,y) = \Sigma \{c_2(i_2,j_2) * \cos(i_2 * \arccos(t_2)) * \cos(j_2 * \arccos(t_2))\}$$

where $c_2(i, j)$ is a coefficient based on $i_2$ and $j_2$, which are each integers (e.g., ranging between 0 and 10), x and y are spatial locations on the second freeform-polynomial surface area and has values between −1.0 and 1.0, and $t_2$ is a normalized parameter having values between −1.0 and 1.0 (e.g., associated with the intended correction meridian).

In some embodiments, the first freeform-polynomial surface area and the second freeform-polynomial surface area each comprises a monofocal lens, a bifocal lens, a multi-focal lens, or an extended range of vision lens.

In some embodiments, the coefficients c(i, j) or $c_2$ ($i_2$, $j_2$) are a function of local coordinates that puts accumulated high surface amplitude to area of non-functional retinal area.

In some embodiments, the coefficients c(i, j) or $c_2(i_2, j_2)$ are a function of local coordinates that accounts for irregular corneal shape.

In some embodiments, the angularly-varying phase member is formed of a refractive structure.

In some embodiments, the angularly-varying phase member is formed of a diffractive structure.

In some embodiments, an offset of each meridian of the plurality of meridians of about 10 degrees causes a MTF (modulation transfer function) measure change of less than 10% at 30 cycles per degree (cpd).

In another aspect, an intraocular lens is disclosed, the intraocular lens comprising an angularly-varying phase member configured to direct light, at a first meridian, to a first point of focus, wherein at angular positions nearby to the first meridian, the angularly-varying phase member is configured to direct light to points of focus nearby to the first point of focus such that rotational offsets of the angularly-varying phase member from the first meridian directs light from the nearby points of focus to the first point of focus, thereby establishing an extended band of operational meridian.

In another aspect, an ophthalmic apparatus is disclosed. The ophthalmic apparatus includes a multi-zonal lens body having a plurality of optical zones, wherein the multi-zonal lens body forms an angularly-varying phase member having a center at a first meridian, the angularly-varying phase member, at the center of the first meridian, comprising a refractive structure to direct light to a first point of focus, wherein at angular positions nearby to the first meridian, the refractive structure directs light to points of focus nearby to the first point of focus such that rotational offsets of the multi-zonal lens body from the center of the first meridian directs light from the nearby points of focus to the first point of focus, thereby establishing a band of operational meridian for the apparatus to an intended correction meridian.

In some embodiments, the refractive structure has a height profile at a face of the ophthalmic apparatus that angularly varies along each meridian nearby to the center of the first meridian.

In some embodiments, the height profile of the refractive structure angularly varies in a continuous gradual manner (e.g., in a cosine, sine, or polynomial-based profile).

In some embodiments, the refractive structure angularly varies along each meridian nearby to the center of the first meridian up to a pre-defined angular position of the apparatus.

In some embodiments, pre-defined angular position is at least about 5 degrees from the center of the first meridian.

In some embodiments, the refractive structure varies along each meridian between the first meridian and a third meridian that is about 45 degrees offset to the first meridian and between the first meridian and a fourth meridian that is about −45 degrees offset to the first meridian.

In some embodiments, the multi-zonal lens body comprises at least three optical zones, the at least three optical zones forming an angularly varying efficiency trifocal optics (e.g., wherein the angularly varying efficiency trifocal optics comprises a first angularly varying phase member, e.g., a first refractive angularly varying phase member, at the first meridian; a second angularly varying phase member, e.g., a second refractive angularly varying phase member, at a second meridian; and a third angularly varying phase member, e.g., a third refractive angularly varying phase member, at a third meridian).

In some embodiments, the multi-zonal lens body comprises at least four optical zones, the at least four optical zones forming an angularly varying efficiency quadric optics (e.g., wherein the angularly varying efficiency trifocal optics comprises a first angularly varying phase member, e.g., a first refractive angularly varying phase member, at the first meridian; a second angularly varying phase member, e.g., a second refractive angularly varying phase member, at a second meridian; a third angularly varying phase member, e.g., a third refractive angularly varying phase member, at a third meridian; and a fourth refractive angularly varying phase member, e.g., a fourth refractive angularly varying phase member, at a fourth meridian).

In some embodiments, the multi-zonal lens body forms a second angularly-varying phase member at a second meridian, wherein the second meridian is orthogonal to the first meridian.

In some embodiments, the first angularly-varying phase member and the second angularly-varying phase member, collectively, form an angularly varying efficiency bifocal optics.

In some embodiments, the second angularly-varying phase member has a center at the second meridian, the second angularly-varying phase member varying along each meridian nearby to the center of the second meridian i) between the second meridian and a third meridian that is about 45 degrees offset to the second meridian and ii) between the second meridian and a fourth meridian that is about −45 degrees offset to the second meridian.

In some embodiments, the refractive structure of the first and second angularly-varying phase members each forms a butterfly pattern.

In some embodiments, the refractive structure of the first and second angularly-varying phase members, collectively, forms butterfly pattern that is expressed as $$r(\theta) = \sqrt{2 \cdot n \cdot \frac{s(\theta) \cdot \lambda}{A(\theta)}},$$

where $r(\theta)$ is the contour radius for the given meridian added power $A(\theta)$, wavelength $\lambda$, zone number n, and the scaling value $s(\theta)$, all at meridian $\theta$.

In some embodiments, the angularly-varying phase member at the first meridian comprises a monofocal lens.

In some embodiments, the second angularly-varying phase member at the second meridian comprises a second monofocal lens.

In some embodiments, each of i) the third meridian located about 45 degrees from first meridian and ii) the fourth meridian located about −45 degrees from the first meridian, collectively, form a bifocal lens.

In some embodiments, the height profile $T1(r, \theta)$ for each meridian $\theta$ is defined as:

$$T1(r,\theta) = t_1(r)|\cos 2(\theta)| + t_2(r)|\sin 2(\theta)|$$

where $t_1(r)$ and $t_2(r)$ are the added power for each zone.

In some embodiments, the first angularly-varying phase member establishes the extended band of operational meridian across a range selected from the group consisting of about ±4 degrees, about ±5 degrees, about ±6 degrees, about ±7 degrees, about ±8 degrees, about ±9 degrees, about ±10 degrees, about ±11 degrees, about ±12 degrees, about ±13, degrees, about ±14 degrees, and about ±15 degrees.

In some embodiments, the ophthalmic apparatus includes a plurality of alignment markings, including a first set of alignment markings and a second set of alignment markings, wherein the first set of alignment markings corresponds to the center of the first meridian, and wherein the second set of alignment markings corresponds to the extended band of operational meridian.

In another aspect, a rotationally-tolerant ophthalmic apparatus is disclosed for correcting astigmatism. The ophthalmic apparatus includes a multi-zonal lens body having a plurality of optical zones configured to apply cylinder power at an astigmatism meridian of an eye, the multi-zonal lens body forming an angularly-varying phase member having a peak cylinder power centered at an astigmatism correcting meridian, the angularly-varying phase member, at the astigmatism correcting meridian, having a refractive structure configured to direct light to a first point of focus on the retina, and wherein the refractive structure of the angularly-varying phase member varies, at each optical zone, along meridians nearby to the astigmatism correcting meridian, to direct light to points of focus nearby to the first point of focus such the refractive structure, when rotationally offset from the peak cylinder power, directs light from the nearby points of focus to the first point of focus, thereby establishing a band of operational meridians over the astigmatism meridian.

In another aspect, a rotationally-tolerant ophthalmic apparatus is disclosed for correcting astigmatism. The ophthalmic apparatus includes an astigmatism correcting meridian corresponding to a peak cylinder power associated with a correction of an astigmatism, the ophthalmic apparatus having a plurality of exterior alignment markings, including a first set of alignment markings and a second set of alignment markings, wherein the first set of alignment markings corresponds to the astigmatism correcting meridian, and wherein the second set of alignment markings corresponds to an operational band of the rotationally-tolerant ophthalmic apparatus.

In another aspect, an ophthalmic apparatus is disclosed. The ophthalmic apparatus has regions of one or more base spherical powers and one or more cylinder powers that are added to one or more base spherical power for correcting an astigmatism (e.g., an intended astigmatism), the apparatus comprising one or more optical zones, including an optical zone defined by a polynomial-based surface coincident at a plurality of meridians having distinct cylinder powers, wherein light incident to a given region of a given meridian of each of the plurality of meridians, and respective regions nearby, is directed to a given point of focus such that the regions nearby to the given region direct light to the given point of focus when the given meridian is rotationally offset from the given region, thereby establishing an extended band of operation, and wherein each of the plurality of meridians is uniformly arranged on the optical zone for a same given added diopter of power up to 1.0D.

In some embodiments, differences among each continuously uniformly distributed contour line, at a given IOL plane, associated with a given meridian of the plurality of meridians is less than about 0.6D (diopters).

In some embodiments, the same given added diopter is about 0.5D (diopters).

In some embodiments, the polynomial-based surface establishes the extended band of operation across a range selected from the group consisting of about ±5 degrees, about ±6 degrees, about ±7 degrees, about ±8 degrees, about ±9 degrees, about ±10 degrees, about ±11 degrees, about ±12 degrees, about ±13, degrees, about ±14 degrees, and about ±15 degrees.

In some embodiments, the polynomial-based surface is characterized by a series of weighted cosine-based functions.

In some embodiments, the plurality of meridians include a first meridian, a second meridian, and a third meridian, each having the extended band of operation of at least 10 degrees.

In some embodiments, a first center of the first meridian is angularly spaced about 90 degrees to a second center of the second meridian.

In some embodiments, the optical zone comprises a fourth meridian having an accumulated high surface amplitude such that the first meridian, the second meridian, and the third meridian have the established extended band of operation.

In some embodiments, the fourth meridian is purposely positioned at an angular position that coincides with a diagnosed limited retinal functional area of a patient.

In some embodiments, the polynomial-based surface comprises a refractive surface.

In some embodiments, the polynomial-based surface comprises a diffractive surface.

In some embodiments, an offset of each meridian of the plurality of meridians of about 10 degrees causes a MTF (modulation transfer function) measure change of less than 10% at 30 cycles per degree (cpd).

In some embodiments, the polynomial-bases surface at a first meridian and at a second meridian comprises a bifocal monofocal lens.

In some embodiments, the polynomial-bases surface at a first meridian comprises a monofocal lens.

In some embodiments, the polynomial-bases surface at a first meridian comprises an extended range lens.

In some embodiments, the ophthalmic apparatus includes an accumulated high surface amplitude area disposed at coordinates that coincides with non-functional or limited functional retinal regions of a given patient.

In another aspect, a rotationally-tolerant ophthalmic apparatus is disclosed for correcting astigmatism, the ophthalmic apparatus comprising a multi-zonal lens body having a plurality of optical zones configured to apply cylinder power at an astigmatism meridian of an eye, the multi-zonal lens body forming a angularly-varying phase member having a peak cylinder power centered at an astigmatism correcting meridian, the angularly-varying phase member at the peak cylinder power being configured to direct light to a first point of focus on the retina, and wherein the angularly-varying phase member varies, at each optical zone, along meridians nearby to the astigmatism correcting meridian to direct light to points of focus nearby to the first point of focus such the multi-zonal lens body, when rotational offset from the peak cylinder power, directs light from the nearby points of focus to the first point of focus, thereby establishing a band of operational meridians over the astigmatism meridian, and wherein the angularly-varying phase member has a profile that is uniformly spaced for a same given added diopter of power up to 1.0D (diopters).

In some embodiments, the band of operation is established across a range selected from the group consisting of about ±5 degrees, about ±6 degrees, about ±7 degrees, about ±8 degrees, about ±9 degrees, about ±10 degrees, about ±11 degrees, about ±12 degrees, about ±13, degrees, about ±14 degrees, and about ±15 degrees.

In some embodiments, the polynomial-based surface is characterized by a series of weighted cosine-based function.

In some embodiments, the angularly-varying phase member has a band of operation of at least 10 degrees.

In some embodiments, the multi-zonal lens body forms a second angularly-varying phase member having a second peak cylinder power centered at a second correcting meridian, the second angularly-varying phase member at the second peak cylinder power being configured to direct light to a second point of focus on the retina, and wherein the second angularly-varying phase member varies, at each optical zone, along meridians nearby to the second correcting meridian to direct light to points of focus nearby to the second point of focus such the multi-zonal lens body, when rotational offset from the second peak cylinder power, directs light from the nearby points of focus to the second point of focus, and wherein the second angularly-varying phase member has the profile that is uniformly spaced for a same given added diopter of power up to 1.0D (diopters).

In some embodiments, the multi-zonal lens body forms a second angularly-varying phase member having a second peak cylinder power centered at a second correcting meridian, the second angularly-varying phase member at the second peak cylinder power being configured to direct light to a second point of focus on the retina, and wherein the second angularly-varying phase member varies, at each optical zone, along meridians nearby to the second correcting meridian to direct light to points of focus nearby to the second point of focus such the multi-zonal lens body, when rotational offset from the second peak cylinder power, directs light from the nearby points of focus to the second point of focus, and wherein the second angularly-varying phase member has a second profile that is uniformly spaced for a same given added diopter of power up to 1.0D.

In another aspect, an ophthalmic apparatus is disclosed, the apparatus having regions of one or more base spherical powers and one or more cylinder powers that are added to the one or more base spherical power for correcting an astigmatism (e.g., an intended astigmatism), the apparatus comprising one or more optical zones, including a first optical zone defined by a freeform-polynomial surface area (e.g., as area having one or more refractive surfaces) coincident with one or more distinct cylinder powers, wherein light incident to a first region of the freeform-polynomial surface area, and regions nearby to the first region, is directed to a first point of focus such that the regions nearby to the first region direct light to the first point of focus when the first freeform-polynomial surface area is rotationally offset from the first region, thereby establishing a band of operational meridian for the apparatus to an intended correction meridian, and wherein the freeform-polynomial surface area is defined as a mathematical expression comprising a combination of one or more polynomial expressions (e.g., Chebyshev-based polynomial expression, Zernike-based polynomial expression, etc.) each having a distinct complex orders.

In some embodiments, at least one of the one or more polynomial expression is selected from the group consisting of a Chebyshev polynomial and a Zernike polynomial.

In some embodiments, the freeform-polynomial surface area establishes the band of operational meridian across a range selected from the group consisting of about ±4 degrees, about ±5 degrees, about ±6 degrees, about ±7 degrees, about ±8 degrees, about ±9 degrees, about ±10 degrees, about ±11 degrees, about ±12 degrees, about ±13, degrees, about ±14 degrees, and about ±15 degrees.

In some embodiments, the freeform-polynomial surface area has a height profile T(x,y) (e.g., an extra height profile having an associated cylinder power) on a first base height profile (e.g., a base or typical aspheric height profile), the height profile being defined as:

$$T(x,y)=\Sigma\{c(i,j)*\cos(i*\arccos(t))*\cos(j*\arccos(t))\}$$

where c(i, j) is a coefficient based on i and j, which are each integers (e.g., having a range between 0 and 10), x and y are spatial locations on the freeform-polynomial surface area, and t is a normalized parameter having values between −1.0 and 1.0.

In some embodiments, the freeform-polynomial surface area has the second height profile T(x,y) in which i has an order of 0 to at least 6 and j has an order of 0 to at least 6.

In some embodiments, the freeform-polynomial surface area spans the entire optical face of the apparatus), wherein the ophthalmic apparatus comprises an optical face (e.g., the portion of the face surface of the ophthalmic apparatus that include corrective optical structures) that includes the one or more optical zones, the optical face having a boundary defined by a first axis of the face and a second axis of the face (e.g., wherein the first axis is orthogonal to the second axis), and wherein each of the x-spatial locations at value −1.0 and at value 1.0 coincides with, or near, the boundary, and each of the y-spatial locations at value −1.0 and at value 1.0 coincides with, or near, the boundary.

In some embodiments, the ophthalmic apparatus comprises an optical face (e.g., the portion of the face surface of the ophthalmic apparatus that include corrective optical structures) that includes the one or more optical zones, the optical face having a boundary defined by a first axis of the face and a second axis of the face (e.g., wherein the first axis is orthogonal to the second axis), and wherein each of the x-spatial locations at value −1.0 and at value 1.0 is located at a first radial position along the first axis between a center location of the ophthalmic apparatus and the boundary, and wherein each of the y-spatial locations at value −1.0 and at value 1.0 is located at the first radial position along the second axis between the center location of the ophthalmic apparatus and the boundary.

In some embodiments, the ophthalmic apparatus comprises an optical face (e.g., the portion of the face surface of the ophthalmic apparatus that include corrective optical structures) that includes the one or more optical zones, the optical face having a boundary defined by a first axis of the face and a second axis of the face (e.g., wherein the first axis is orthogonal to the second axis), and wherein each of the x-spatial locations at value −1.0 and at value 1.0 is located at a first radial position along the first axis between a center location of the ophthalmic apparatus and the boundary, and wherein each of the y-spatial locations at value −1.0 and at value 1.0 is located at a second radial position along the second axis between the center location of the ophthalmic apparatus and the boundary, wherein the first radial position and the second radial position are different.

In some embodiments, the freeform-polynomial surface area has for each continuously distributed contour line at the IOL plane a difference of less than about 0.6 Diopters.

In some embodiments, the one or more optical zones includes a second optical zone defined by a second freeform-polynomial surface region, wherein the second freeform-polynomial surface area is characterized and defined by a second polynomial.

In some embodiments, the second freeform polynomial surface area has a second height profile that varies according to a freeform polynomial selected from the group consisting of a Chebyshev polynomial and a Zernike polynomial.

In some embodiments, the one or more optical zones includes a second optical zone defined by a second freeform-polynomial surface region, wherein the second freeform-polynomial surface area is characterized and defined by a second combination of one or more polynomial expressions (e.g., Chebyshev-based polynomial expression, Zernike-based polynomial expression, etc.) each having a distinct complex orders.

In some embodiments, at least one of the one or more polynomial expression is selected from the group consisting of a Chebyshev polynomial and a Zernike polynomial.

In some embodiments, light incident to a second region of the second freeform-polynomial surface area, and regions nearby to the second region, is directed to a second point of focus such that the regions nearby to the second region direct light to the second point of focus when the second freeform-polynomial surface area is rotationally offset from the second region.

In some embodiments, light incident to a second region of the second freeform-polynomial surface area, and regions nearby to the second region, is directed to the first point of focus such that the regions nearby to the second region direct light to the first point of focus when the second freeform-polynomial surface area is rotationally offset from the second region (e.g., over the band of operational meridian).

In some embodiments, the second freeform-polynomial surface area has a third height profile $T_2(x,y)$ (e.g., an extra height profile associated with cylinder power) superimposed on a first height profile (e.g. a base or typical aspheric height profile), the third height profile being defined as:

$$T_2(x,y) = \Sigma \{c_2(i_2,j_2)*\cos(i_2*\arccos(t_2))*\cos(j_2*\arccos(t_2)))\}$$

where $c_2(i, j)$ is a coefficient based on $i_2$ and $j_2$, which are each integers (e.g., ranging between 0 and 10), x and y are spatial locations on the second freeform-polynomial surface area and has values between −1.0 and 1.0, and $t_2$ is a normalized parameter having values between −1.0 and 1.0 (e.g., associated with the intended correction meridian).

In some embodiments, the first freeform-polynomial surface area comprise a monofocal lens, a bifocal lens, or a multi-focal lens.

In some embodiments, the second freeform-polynomial surface area comprise a monofocal lens, a bifocal lens, or a multi-focal lens.

In some embodiments, the first freeform-polynomial surface area comprise an extended range of vision lens.

In some embodiments, the second freeform-polynomial surface area comprise an extended range of vision lens.

In some embodiments, the first freeform-polynomial surface area comprises refractive surfaces.

In some embodiments, the first freeform-polynomial surface area comprises diffractive surfaces.

In some embodiments, the coefficients $c(i, j)$ are a function of local coordinates that puts accumulated high surface amplitude to area of non-functional retinal area.

In some embodiments, the coefficients $c(i, j)$ are a function of local coordinates that accounts for irregular corneal shape.

In another aspect, a method of designing an ophthalmic apparatus (e.g., the design of FIG. 4) having regions of one or more base spherical powers and one or more cylinder powers that are added to the one or more base spherical power for correcting an astigmatism (e.g., an intended astigmatism), the method comprising: generating, via a processor, one or more optical zones, including a first optical zone defined by a freeform-polynomial surface area (e.g., as area having one or more refractive surfaces) coincident with one or more distinct cylinder powers, wherein light incident to a first region of the freeform-polynomial surface area, and regions nearby to the first region, is directed to a first point of focus such that the regions nearby to the first region direct light to the first point of focus when the first freeform-polynomial surface area is rotationally offset from the first region, thereby establishing a band of operational meridian for the apparatus to an intended correction meridian, and wherein the freeform-polynomial surface area is defined as a mathematical expression comprising a combination of one or more polynomial expressions (e.g., Chebyshev-based polynomial expression, Zernike-based polynomial expression, etc.) each having a distinct complex orders.

It is contemplated that the angularly-varying phase member may be purely refractive or a hybrid of diffractive and refractive. It is also contemplated that angularly-varying phase members may comprise of different materials such as a stacking lens, where each layer is comprised of a different material. It is further contemplated that the angularly-varying phase members may be comprised of a material or materials that have a variation in refractive index, a gradient index, or a programmed index, for example liquid crystal which creates the refractive change.

In some embodiments, the angularly-varying phase member establishes the band of operational meridian across a range selected from the group consisting of about ±4 degrees, about ±5 degrees, about ±6 degrees, about ±7 degrees, about ±8 degrees, about ±9 degrees, about ±10 degrees, about ±11 degrees, about ±12 degrees, about ±13, degrees, about ±14 degrees, and about ±15 degrees.

In another aspect, a rotationally-tolerant ophthalmic apparatus (e.g., toric intraocular lens) having an established band of operation meridians (e.g., at least about ±4 degrees or more) for placement over an intended astigmatism meridian is disclosed. The ophthalmic apparatus includes a multi-zonal lens body having a plurality of optical zones, where the multi-zonal lens body forms the angularly-varying phase member. The angularly-varying phase member has a center at an astigmatism correction meridian that directs light to a first point of focus (e.g., on the retina). At angular positions nearby to the astigmatism correction meridian, the portion of the angularly-varying phase member at such angular positions directs light to points of focus of varying depths and nearby to the first point of focus such that rotational offsets of the multi-zonal lens body from the center of the astigmatism correction meridian directs light from the nearby points of focus to the first point of focus.

In another aspect, a rotationally-tolerant ophthalmic apparatus for correcting astigmatism is disclosed. The ophthalmic apparatus includes an astigmatism correcting meridian that corresponds to a peak cylinder power associated with a correction of an astigmatism. The rotationally-tolerant ophthalmic apparatus may include a plurality of exterior alignment markings, including a first set of alignment markings and a second set of alignment markings. The first set of alignment markings corresponds to the astigmatism correcting meridian, and the second set of alignment markings corresponds to an operation band of the rotationally-tolerant ophthalmic apparatus.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIGS. 2A, 2B, 2C, 2D, 2E, and 2F, each illustrates a plurality of exemplary height profiles of the anterior or posterior face of the ophthalmic apparatus of FIGS. 1A-1B in accordance with an illustrative embodiment.

FIGS. 7A and 7B are diagrams of an exemplary ophthalmic apparatus that includes angularly-varying phase members in accordance with another illustrative embodiment.

FIGS. 8 and 9 are diagrams illustrating height profiles of exemplary ophthalmic apparatuses of FIGS. 1A-1B and 7A-7B in accordance with the illustrative embodiments.

FIG. 14 is a table of the ophthalmic apparatus of FIG. 13 configured as a tri-focal lens in accordance with another illustrative embodiment.

FIGS. 16A, 16B, and 16C, each illustrates a plurality of exemplary height profiles of the ophthalmic apparatus of FIGS. 15A-15B in accordance with an illustrative embodiment.

FIGS. 17A and 17B are diagrams of an exemplary ophthalmic apparatus that includes angularly-varying phase members and a symmetric height profile in accordance with another illustrative embodiment.

FIGS. 18A, 18B, and 18C, each illustrates a plurality of exemplary height profiles of the anterior or posterior face of the ophthalmic apparatus of FIGS. 17A-17B in accordance with an illustrative embodiment.

FIGS. 20A, 20B, 20C, 20D, and 20E illustrate a plurality of exemplary height profiles of the anterior or posterior face of the ophthalmic apparatus of FIGS. 19A-19B, in accordance with an illustrative embodiment.

FIGS. 21A, 21B, and 21C are diagrams illustrating an exemplary ophthalmic apparatus that includes refractive angularly-varying phase members, in accordance with another illustrative embodiment.

DETAILED DESCRIPTION OF THE PREFERRED EMBODIMENT

Each and every feature described herein, and each and every combination of two or more of such features, is included within the scope of the present invention provided that the features included in such a combination are not mutually inconsistent.

Embodiments of the present invention are generally directed to toric lenses or surface shapes, and/or related methods and systems for fabrication and use thereof. Toric lenses according to embodiments of the present disclosure find particular use in or on the eyes of human or animal subjects. Embodiments of the present disclosure are illustrated below with particular reference to intraocular lenses; however, other types of lenses fall within the scope of the present disclosure. Embodiments of the present disclosure provide improved ophthalmic lens (including, for example, contact lenses, and intraocular lenses, corneal lenses and the like) and include monofocal refractive lenses, monofocal diffractive lenses, bifocal refractive lenses, bifocal diffractive lenses, and multifocal refractive lenses, multifocal diffractive lenses.

As used herein, the term "refractive optical power" or "refractive power" means optical power produced by the refraction of light as it interacts with a surface, lens, or optic. As used herein, the term "diffractive optical power" or "diffractive power" means optical power resulting from the diffraction of light as it interacts with a surface, lens, or optic.

As used herein, the term "optical power" means the ability of a lens or optics, or portion thereof, to converge or diverge light to provide a focus (real or virtual), and is commonly specified in units of reciprocal meters ($m^{-1}$) or Diopters (D). When used in reference to an intraocular lens, the term "optical power" means the optical power of the intraocular lens when disposed within a media having a refractive index of 1.336 (generally considered to be the refractive index of the aqueous and vitreous humors of the human eye), unless otherwise specified. Except where noted otherwise, the optical power of a lens or optic is from a reference plane associated with the lens or optic (e.g., a principal plane of an optic). As used herein, a cylinder power refers to the power required to correct for astigmatism resulting from imperfections of the cornea and/or surgically induced astigmatism.

As used herein, the terms "about" or "approximately", when used in reference to a Diopter value of an optical power, mean within plus or minus 0.25 Diopter of the referenced optical power(s). As used herein, the terms "about" or "approximately", when used in reference to a percentage (%), mean within plus or minus one percent (±1%). As used herein, the terms "about" or "approximately", when used in reference to a linear dimension (e.g., length, width, thickness, distance, etc.) mean within plus or minus one percent (1%) of the value of the referenced linear dimension.

Figures 1A, 1B:
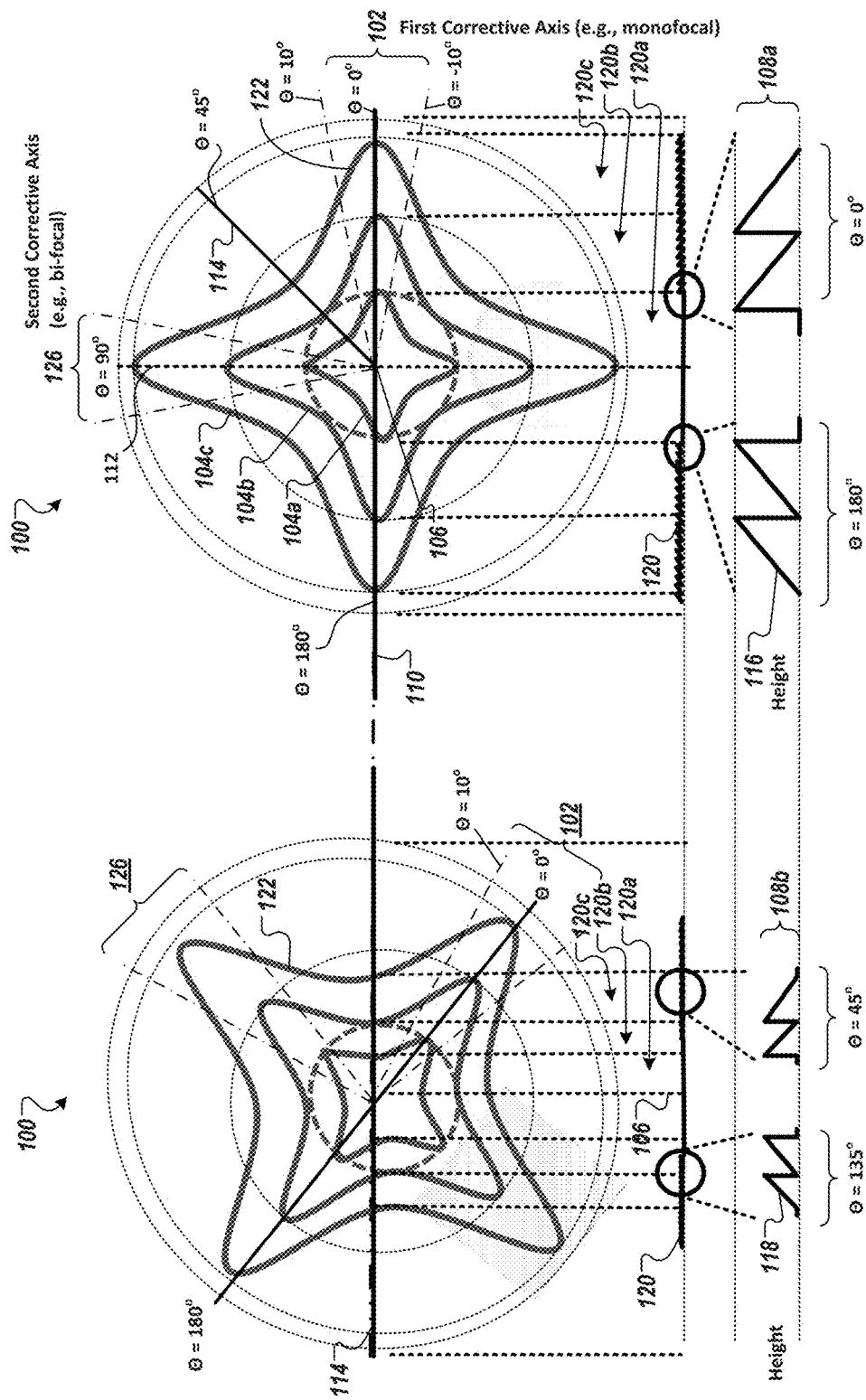
FIGS. 1A and 1B are diagrams of an exemplary ophthalmic apparatus (e.g., an intraocular toric lens) that includes angularly-varying phase members (reflective, diffractive, or both) that each provides an extended rotational tolerance of the apparatus in accordance with an illustrative embodiment.

FIGS. 1A and 1B are diagrams of an exemplary ophthalmic apparatus 100 (e.g., an intraocular toric lens) that includes angularly-varying phase members 102 (refractive, diffractive, or both) configured to provide extended rotational tolerance in accordance with an illustrative embodiment.

The angularly-varying phase members have a center structure that applies cylinder power at a corrective meridian (e.g., the high power meridian). In FIGS. 1A and 1B, the corrective meridian is shown at Θ=0° and Θ=180° with the center structure being disposed at such Θ positions. Off-center structures of the angularly-varying phase members extend from the center structure in a gradually varying manner to apply cylinder power to a band of meridians surrounding the corrective meridian enabling the ophthalmic apparatus to operate off-axis (or off-meridian) to the corrective meridian (e.g., the astigmatism meridian). As shown in FIG. 1A, the off-center structures extends, at least, from $\Theta=0°$ to $\Theta=10°$ and $\Theta=-10°$ to facilitate off-axis operation (from $\Theta=0°$) up to ±10°. The off-center structures may extend from $\Theta=0°$ to $\Theta=90°$ and $\Theta=-90°$. These meridians may be referred to as a dynamic meridian.

Although the operational boundaries of the angularly varying phase members are shown to be at about ±10°, it is contemplated that other angular values may be used, as are discussed herein. In addition, in some embodiments, it is also contemplated that operational boundaries may be symmetrical or asymmetrical. For example, in certain embodiments, the operational boundaries may be skewed to one rotation, e.g., between +9° and −11° or, e.g., between +11° and −9°.

The angularly-varying phase members, in some embodiments, include an optimized combination of angularly and zonally diffractive (or refractive) phase structure located at each meridian to vary the extended depth of focus to a plurality of nearby focus points. Light directed to such nearby focus points are thus directed to the desired focus point when the ophthalmic apparatus is subjected to a rotational offset from a primary intended axis of alignment, thereby extending the rotational tolerance of the apparatus to an extended tolerance band. This may also be referred to as "extended tolerance astigmatism band" or "extended misalignment band." Remarkably, this extended tolerance astigmatism band delivers cylinder power to correct for the astigmatism for a range of meridians (e.g., up to ±10° or more as shown in FIGS. 1A and 1B), thereby eliminating any need for additional corrective measures (e.g., supplemental corrective devices or another surgical intervention) when the implanted ophthalmic apparatus is not perfectly aligned to the desired astigmatism meridian in the eye.

Put another way, the angularly-varying phase members facilitate an extended band of the corrective meridian that has minimal, and/or clinically acceptable, degradation of the visual acuity and modulation transfer function when the ophthalmic apparatus is subjected to rotational misalignment between the astigmatic axis and a center axis of the corrective meridian.

In some embodiments, an exemplified toric IOL includes dynamic meridian or angularly varying efficiency quadric optics. In another embodiment, an exemplified toric IOL includes dynamic meridian or angularly varying efficiency trifocal optics. In another embodiment, an exemplified toric IOL includes double dynamic meridian or angularly varying efficiency bifocal optics. In another embodiment, the bifocal or trifocal feature may be disposed on one optical surface or on both optical surfaces of a single optical lens or on any surfaces of a multiple optical elements working together as a system.

Referring still to FIGS. 1A and 1B, an embodiment of the angularly-varying phase members 102 is shown. In this embodiment, the angularly-varying phase members 102 are formed in multiple-zones (shown as zones 120a, 120b, 120c), each forming a spatially-varying "butterfly" shaped structure centered around the optical axis 106. The multiple-zone structure (120a, 120b, and 120c), and angularly-varying phase members 102 therein, form a first "high power meridian" (e.g., having a constant power equal to the base spherical power plus a cylinder power of the lens) at a first meridian (e.g., axis 110 shown as $\Theta=0°$ and $\Theta=180°$) that corresponds to an axis of the eye to apply a correction. The first corrective meridian 110 focuses light that passes therethrough to a first foci (i.e., point of focus) and is intended to align with the astigmatic axis of the eye. At nearby meridians (e.g., −10°, −9°, −8°, −7°, −6°, −5°, −4°, −3°, −2°, −1°, 1°, 2°, 3°, 4°, 5°, 6°, 7°, 8°, 9°, and 10°), the angularly-varying phase members 102 focus light that passes therethrough to a plurality of foci near the first foci. The angularly-varying phase members 102 vary from between the first meridian ($\Theta=0°$) and another meridian located about 10 degrees from the first meridian (e.g., axis 114 shown as $\Theta=10°$).

FIGS. 1A and 1B illustrate the exemplary ophthalmic apparatus 100 having a diffractive surface 120. A diffractive surface comprises multiple echelette elements. In some embodiments, an intraocular lens, which has a diffractive grating covering its entire surface, has between 15 and 32, or more echelette elements. In some embodiments, the diffractive grating includes more than 32 echelette elements. As shown in FIGS. 1A and 1B, multiple echelette elements cover each region, or if there is one echelette element, or the echelette spans only a portion of the region, then a refractive area will cover the rest of the region. Though shown here as a diffractive surface, the angularly varying phase members are later illustrated as a refractive surface, as later discussed herein.

As shown in FIGS. 1A and 1B, both the heights (i.e., thicknesses) of the lens and the spatial sizes, at each zone, vary among the different axes to form the angularly-varying phase member 102. To illustrate this structure, both a first height profile 116 of the lens along the first corrective meridian (e.g., at $\Theta=0°$) and a second height profile 118 of the lens along a lower power meridian (i.e., at axis 114 shown as $\Theta=10°$) are presented at plots 108a and 108b, respectively, for each of FIGS. 1A and 1B. The height profile of the lens varies at each axis as the first height profile 116 gradually transitions (e.g., as shown by the curved profile 122) into the second height profile 118. The first and second height profiles 116 and 118 are illustrated relative to one another in a simplified format. It should be appreciated that there may be multiple echelette elements (i.e., diffractive structures) in each of the multiple zone structures, surrounded by a refractive region. Alternatively, rather than relying on diffraction, one or more of the multiple zone structures may have only refraction surfaces to vary power.

It should also be appreciated that the height profiles herein are illustrated in a simplified form (e.g., as a straight line). The height profiles for each zone may form other surfaces—such as refractive, diffractive—or have other shapes—such convex, concave, or combinations thereof. The profiles may be added to, or incorporated into, a base lens as, for example, shown in FIGS. 4A, 4B, 4C, and 4D. FIGS. 4A, 4B, 4C, and 4D are schematic diagrams of exemplary ophthalmic apparatuses that include either refractive or diffractive angularly-varying phase members, in accordance with an illustrative embodiment.

Referring still to FIGS. 1A and 1B, the multiple-zone structure (e.g., 104a, 104b, and 104c), and angularly-varying phase members 126 therein, form a second "high power meridian" 112 (i.e., axis 112 shown as $\Theta=90°$) which is orthogonal to the first corrective meridian 110. The second corrective meridian 112 includes a second angularly varying phase structure 126. In some embodiments, the second angularly varying phase structure focuses light to a second set of foci (e.g., as part of a multi-focal lens configuration).

FIGS. 2A, 2B, 2C, 2D, 2E, and 2F, each illustrates a plurality of height profiles of the angularly-varying phase member 102 of FIGS. 1A and 1B between the first high power meridian (at $\Theta=0°$) and the operational edge of the angularly varying phase members in accordance with an illustrative embodiment. In FIG. 2B, representative height profiles (of an echelette element) at Θ=0° (202); Θ=2° (204); Θ=4° (206); Θ=6° (208); Θ=8° (210); and Θ=10° (212) (also shown in FIG. 2A) are provided as cross-sections of the echelette elements at the different meridians shown in FIG. 2A. As shown, the height profiles at axes nearby to the first high power meridian (e.g., between ±10°) have a similar shape, as the first high power meridian. The height profile varies in a continuous gradual manner (e.g., having a sine and cosine relationship) along the radial direction (e.g., at different radial values) and along the angular direction (e.g., at different angular positions). The varying of the angular position and of the radial position, e.g., between Θ=0° and Θ=10° and between Θ=0° and Θ=−10° forms the angularly varying phase member. This can also be observed in FIGS. 2B and 2C. In FIGS. 2B and 2C, the edge of an echelette element of the height profile of the angularly-varying phase member at Θ=2° (204) is shown to vary more abruptly in relation to the center meridian at Θ=0° (202). The abrupt transition in the edge position is shown to transition more slowly at Θ=4° (206), and even more slowly at Θ=6° (208); then Θ=8° (210); and then Θ=10° (212). In contrast, the height profile transitions more slowly near the center meridian at Θ=0° and then more sharply at the edge. This transition may be described as a cosine-based or sine-based function, a polynomial function, or a function derived from a combination thereof.

FIG. 2C illustrates a height profiles (near the optical axis and between the operational boundaries of the angularly varying phase member 102) at Θ=0° (202); Θ=2° and −2° (204); Θ=4° and −4° (206); Θ=6° and −6° (208); Θ=8° and −8° (210); and Θ=10° and −10° (212) superimposed next to one another. This variation of the height profile along the radial axis provides a lens region that focuses light at the desired foci and other foci nearby. To this end, radial offset (i.e., misalignment) of the ophthalmic apparatus from the center axis of a desired corrective meridian results in its nearby regions focusing the light to the desired foci. This effect is further illustrated in FIG. 3.

In FIGS. 2D, 2E, and 2F, example height profiles of the lens surface between Θ=0° and Θ=45° are shown. As shown in FIGS. 2E and 2F, the height profiles of the angularly varying phase member vary as a cosine-based or sine-based function. In some embodiments, the height profiles of the lens surface between Θ=45° and Θ=90° are mirrored at Θ=45° to the lens surface between Θ=0° and Θ=45°.

Figure 3:
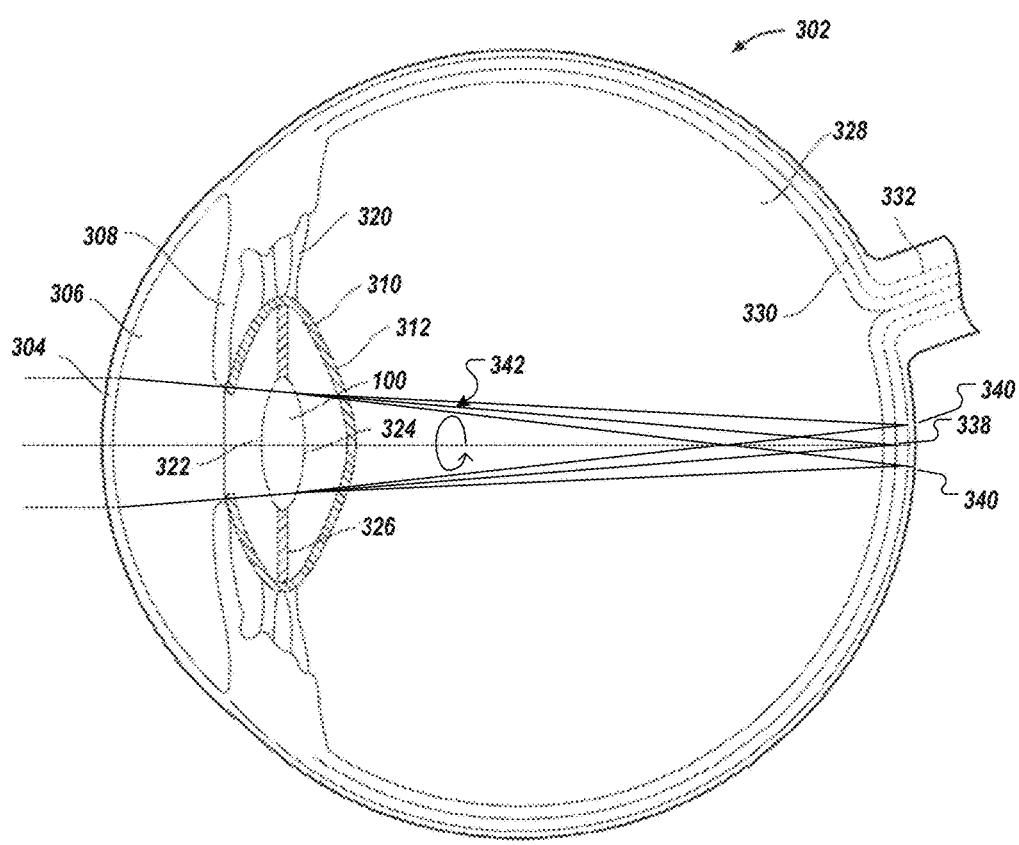
FIG. 3 is a schematic drawing of a top view of a human eye, in which the natural lens of the eye has been removed and replaced with an ophthalmic apparatus that includes angularly-varying phase members in accordance with an illustrative embodiment.

FIG. 3 is a schematic drawing of a top view of a human eye 302, in which the natural lens of the eye 302 has been removed and replaced with an intraocular lens 100 (shown in simplified form in the upper portion of FIG. 3 and in greater detail in the lower portion of FIG. 3). Light enters from the left of FIG. 3, and passes through the cornea 304, the anterior chamber 306, the iris 308, and enters the capsular bag 310. Prior to surgery, the natural lens occupies essentially the entire interior of the capsular bag 310. After surgery, the capsular bag 310 houses the intraocular lens 100, in addition to a fluid that occupies the remaining volume and equalizes the pressure in the eye.

After passing through the intraocular lens, light exits the posterior wall 312 of the capsular bag 310, passes through the posterior chamber 328, and strikes the retina 330, which detects the light and converts it to a signal transmitted through the optic nerve 332 to the brain. The intraocular lens 100 comprises an optic 324 and may include one or more haptics 326 that are attached to the optic 324 and may serve to center the optic 324 in the eye and/or couple the optic 324 to the capsular bag 310 and/or zonular fibers 320 of the eye.

Figures 4A, 4B, 4C, 4D:
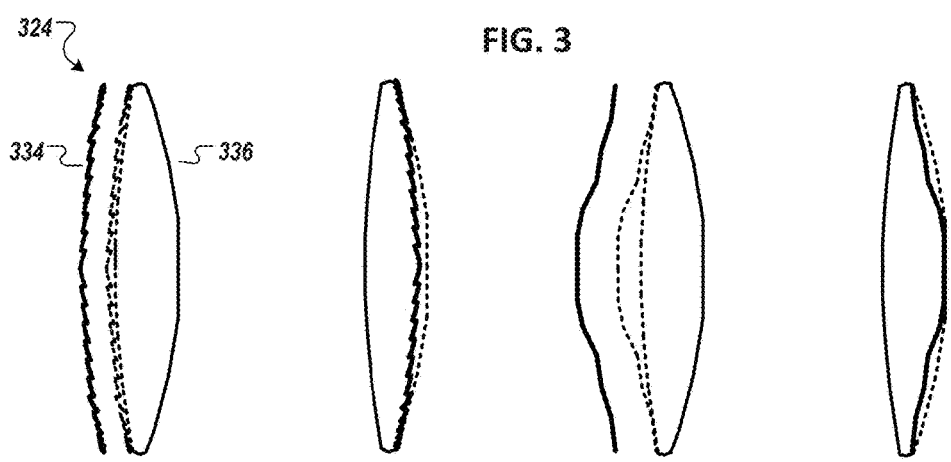
FIGS. 4A, 4B, 4C, and 4D are schematic diagrams of exemplary ophthalmic apparatuses that include either refractive or diffractive angularly-varying phase members, in accordance with an illustrative embodiment.

The optic 324 has an anterior surface 334 and a posterior surface 336, each having a particular shape that contributes to the refractive or diffractive properties of the lens. Either or both of these lens surfaces may optionally have an element made integral with or attached to the surfaces. FIGS. 4A, 4B, 4C, and 4D are schematic diagrams of exemplary ophthalmic apparatuses that include either refractive or diffractive angularly-varying phase members, in accordance with an illustrative embodiment. Specifically, FIGS. 4A and 4B show examples of diffractive lenses, and FIGS. 4C and 4D show examples of refractive lenses. The diffractive lenses or refractive lenses includes the angularly varying phase members as described herein. The refractive and/or diffractive elements on the anterior and/or posterior surfaces, in some embodiments, have anamorphic or toric features that can generate astigmatism to offset the astigmatism from a particular cornea in an eye.

Referring still to FIG. 3, the intraocular lens 100 includes angularly-varying phase members (reflective, diffractive, or both) that focus at a plurality of focus points that are offset radially to one another so as to provide an extended tolerance to misalignments of the lens 100 when implanted into the eye 302. That is, when the center axis of a corrective meridian is exactly matched to the desired astigmatic axis, only a first portion of the cylinder axis is focused at the desired point of focus (338) (e.g., at the retina) while second portions of the cylinder axis focuses at other points (340) nearby that are radially offset to the desired point of focus (338). To this end, when the primary axis of the astigmatism of the intraocular lens is rotationally offset (shown as arrow 342) with the astigmatism of the eye, the second portion of the cylinder axis focuses the light to the desired point of focus.

Artificial lenses (e.g., contact lenses or artificial intraocular lenses) can correct for certain visual impairments such as an inability of the natural lens to focus at near, intermediate or far distances; and/or astigmatism. Intraocular toric lenses have the potential for correcting astigmatism while also correcting for other vision impairments such as cataract, presbyopia, etc. However, in some patients, implanted intraocular toric lenses may not adequately correct astigmatism due to rotational misalignment of the corrective meridian of the lenses with the astigmatic meridian. In some patients following the surgical implant of the toric lenses, the corrective meridian of the implanted toric lenses can be rotationally misaligned to the astigmatic meridian, in some instances, by as much as 10 degrees. However, toric lenses that are designed to provide maximum correction (e.g., 1D to 9D) at the astigmatic meridian are subject to significant reduction in effectiveness of the correction due to any misalignment from the corrective meridian. In certain designs, it is observed that if the cylindrical power axis were mismatched by 1 degree, there would be about 3 percent reduction of the effectiveness of the correction. The degradation increases with the degree of misalignment. If there were a 10-degree misalignment, there would be about 35% reduction of the effectiveness of the correction. This effect is illustrated in FIG. 4 discussed below.

Figure 5A:
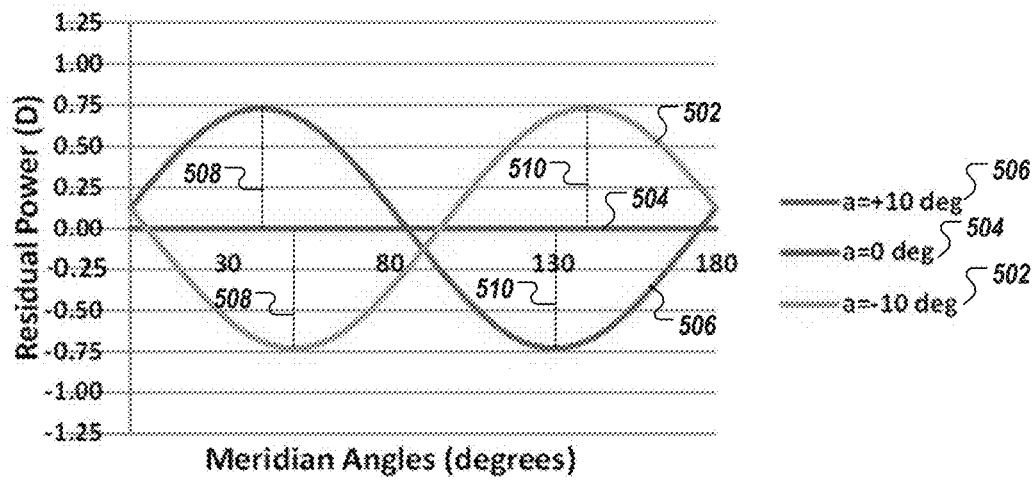
FIGS. 5A and 5B are plots illustrating performance of a conventional toric lens designed to apply maximum cylinder power at a corrective meridian when subjected to rotational misalignment.
Figure 5B:
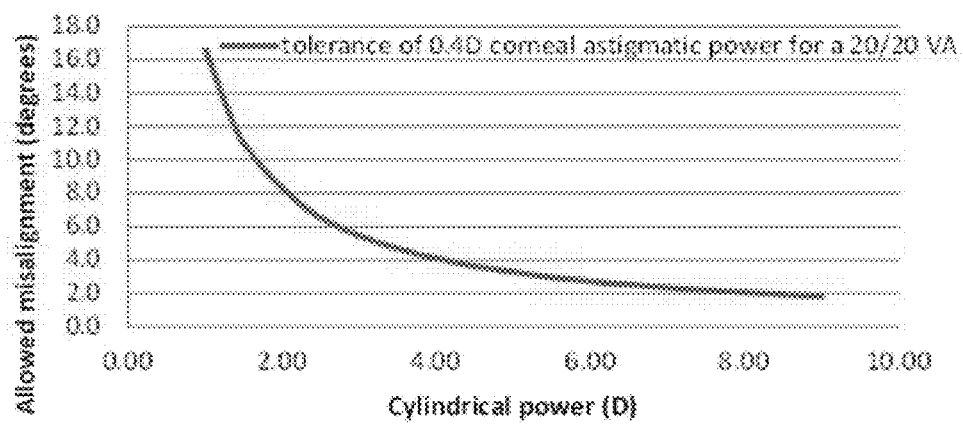

FIGS. 5A and 5B include plots that illustrated the above-discussed degraded performance of conventional toric lens when subjected to rotational misalignments. This conventional toric lens is configured to provide 6.00 Diopters cylinder powers at the IOL plane, 4.11 Diopters cylinder power at the corneal plane, and a corneal astigmatism correction range (i.e., preoperative corneal astigmatism to predicted effects) between 4.00 and 4.75 Diopters.

Referring to FIG. 5A, a plot of the undesired meridian power (also referred to as a residual meridian power ("OC")) (shown along the y-axis) added due to the rotational misalignments (shown along the x-axis) of the toric IOL is shown, including the residual powers for i) a negative 10-degree misalignment (shown as line 502), ii) a 0-degree misalignment (shown as line 504), and iii) a positive 10-degree misalignment (shown as line 506). As shown, the undesired added meridian power varies between a maximum of ±0.75 Diopters at around the 45-degree meridian angle (shown as 508) and at about the 135-degree meridian angle (shown as 510). Notably, this undesired added meridian power is outside the tolerance of a healthy human eye, which can tolerant undesired effects up to about 0.4 Diopters (e.g., at the cornea plane) for normal visual acuity (i.e., "20/20 vision"). Because the undesired effects exceeds the astigmatism tolerance of the human eye, corrective prescription glasses, or further surgical operation to correct the implant misalignment, may be necessary to mitigate the effects of the misalignment of such toric IOLs.

This undesired meridian power may be expressed as Equation 1 below.

$$OC = 2\sin\alpha * \frac{c}{2} 0.7 \cos\left(2\left(\theta + 90 + \frac{\alpha}{2}\right)\right) \quad \text{(Equation 1)}$$

As shown in Equation 1, $\theta$ is the correction meridian (also referred to as the cylindrical power axis) (in degrees); C is the astigmatic power (at the IOL plane) to be corrected at meridian $\theta$ (in Diopters); and a is the magnitude of rotational misalignment of the cylindrical power axis to the astigmatic axis (in degrees).

FIG. 5B shows a plot illustrating the tolerance of a toric IOL to misalignment (shown in the y-axis) and a corresponding cylindrical power that may be applied (shown in the x-axis) for each misalignment to not exceed the astigmatism tolerance of the human eye (i.e., degrade the overall visual acuity). The tolerance to misalignment may be calculated as $$|\alpha| \le \sin^{-1}\frac{\frac{0.4}{2}}{\frac{C}{0.7}}$$

where $\alpha$ is the magnitude of rotational misalignment (in degrees). The calculation may be reduced to $$|\alpha| \le \sin^{-1}\frac{0.29}{C}.$$

As shown, for a misalignment of 5 degrees, which is routinely observed in IOL implantations, the correction effectiveness of such IOL implants can only be maintained for a toric IOL with 3.75 Diopters or less. That is, a toric IOL having cylinder power above 3.75 Diopters would exhibit degraded visual acuity due to the residual power exceeding the astigmatism tolerance of a human eye. This effect is worsen with further degrees of misalignment. For example, at about 10 degrees, the effectiveness of a toric IOL is greatly reduced where only 1.5 Diopters cylinder power or less can be applied so as to not detrimentally effect the visual acuity. Given that cylinder power of convention toric IOLs may range between 1.00 Diopters and 9.00 Diopters, these toric IOLs are reduced in effectiveness post-operation due to the misalignments of cylinder axis.

Figure 6A:
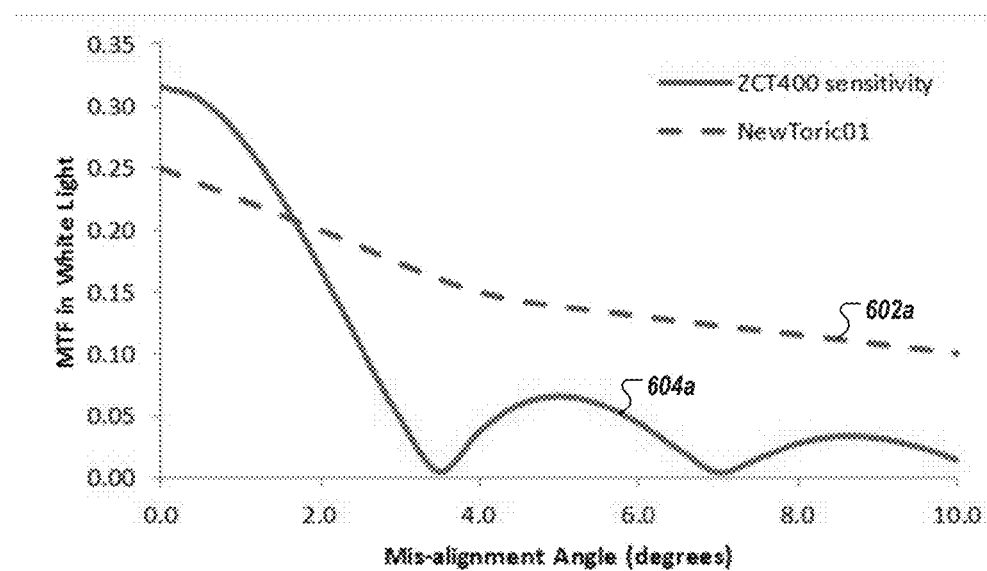
FIGS. 6A and 6B show plots of off-axis performances of an exemplary ophthalmic apparatus (diffractive or refractive) that includes angularly-varying phase members in accordance with an illustrative embodiment.
Figure 6B:
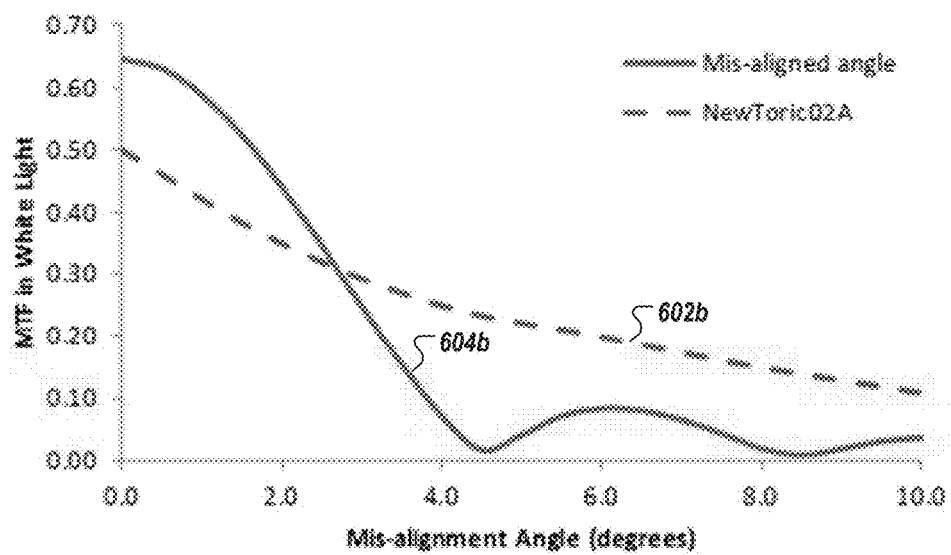

Each of FIGS. 6A and 6B shows plots illustrating modular transfer functions (MTFs) in white light for two toric IOLs (shown as 602a and 602b) each configured with angularly-varying phased members when subjected to off-axis rotations. FIG. 6A illustrates the performance for a refractive toric IOL, and FIG. 6B illustrates performance for a diffractive toric IOL.

Remarkably, the cylinder power of the lens configured with angularly varying phase members provides an extended tolerance of misalignment up to 10 degrees, and more, of off-axis rotation. As shown in FIGS. 6A and 6B, the modulation transfer function (MTF) is maintained across the extended range of alignment for a lens configured with the angularly varying phase members. In contrast, at certain degrees of misalignment, the MTF of a toric IOL (shown as lines 604a and 604b) without the angularly varying phase member is near zero. For example, as shown in FIG. 6A, the MTF at about 3.5 degrees misalignment for a conventional toric lens is near zero. MTF is a modulation of the amplitude and phase functions of an image formed by the white light on a specified plane, e.g., the retina of the human eye, and characterizes the sensitivity of the lens.

Referring still to FIGS. 6A and 6B, an ophthalmic apparatus that includes angularly varying phase members has a lower maximum cylinder range (as compared to lens without such structure). Rather, the angularly varying phase members apply the cylinder power to a band surrounding the corrective meridian, thereby providing a continuous band that makes the lens may tolerant due to misalignment. As shown, in this embodiment, the sensitivity of the ophthalmic apparatus with the angularly varying phase members is less by 20% as compared to a lens without the angularly varying phase members. And, at 10 degrees of misalignment (or off-axis operation) from the targeted corrective axis, the modulation transfer function (MTF) degradation for the ophthalmic apparatus configured with the angularly varying phase member is still acceptable. In this example, the ophthalmic apparatus configured with the angularly varying phase members is configured as a monofocal toric lens with 4.0 Diopters cylindrical power. Here, the MTF is at 100 lp/-mm and has a spatial frequency equivalent to 30 c/degree for an emmetropia eye with 20/20 visual acuity. The performance of the toric IOL with the angularly varying phase member at 5 degrees off-meridian (e.g., line 602a) has comparable MTF performance to a similar toric IOL without the angularly varying phase structure at 2 degrees of misalignment (e.g., line 604a).

FIGS. 7A and 7B are diagrams of an ophthalmic apparatus 100 (e.g., an intraocular toric lens) that includes angularly-varying phase members 102 (reflective, diffractive, or both) that disperse light therethrough to a plurality of foci that are offset radially to one another so as to provide an extended tolerance to misalignments of the lens 100 when implanted in an eye in accordance with another illustrative embodiment. As shown in FIGS. 7A-7B, the apparatus 100 has an asymmetric height profile 702 in which the maximum height of the face of the apparatus differs between the different zones. To demonstrate the asymmetric height profile 702, representative echelette in zones 120b and 120c of an example refractive surface is shown. In zone 120b, the height of a representative echelette 704 is shown to be greater than the height of a representative echelette 706 in zone 120c.

In some embodiments, the asymmetric height profile 702 may be configured to direct light to a plurality foci. For example, the apparatus 100 with the asymmetric height profile 702 may be used for as a trifocal lens. In other embodiments, the apparatus with the asymmetric height profile 702 is used for a quad-focal lens. In some embodiments, the apparatus 100 with the asymmetric height profile 702 is used for a double bi-focal lens. In some embodiments, the apparatus 100 with the asymmetric height profile 702 is used for a mono-focal lens. In some embodiments, the apparatus 100 with the asymmetric height profile 702 is used for a combined bi-focal and tri-focal lens. In some embodiments, the apparatus 100 with the asymmetric height profile 702 is used for an anterior bifocal and a posterior tri-focal lens. In some embodiments, the apparatus 100 with the asymmetric height profile 702 is used for a posterior bifocal and an anterior tri-focal lens.

FIGS. 8 and 9 illustrate a plurality of height profiles of the angularly-varying phase members 102 of the lens in accordance with various illustrative embodiments. As shown in FIG. 8, the height profile is symmetric at each meridian in that the maximum height (shown as 802, 804, and 806) at the face of the lens are the same. As shown in FIG. 9, the height profile is asymmetric in that the maximum height at the face of the lens are different.

Figure 10:
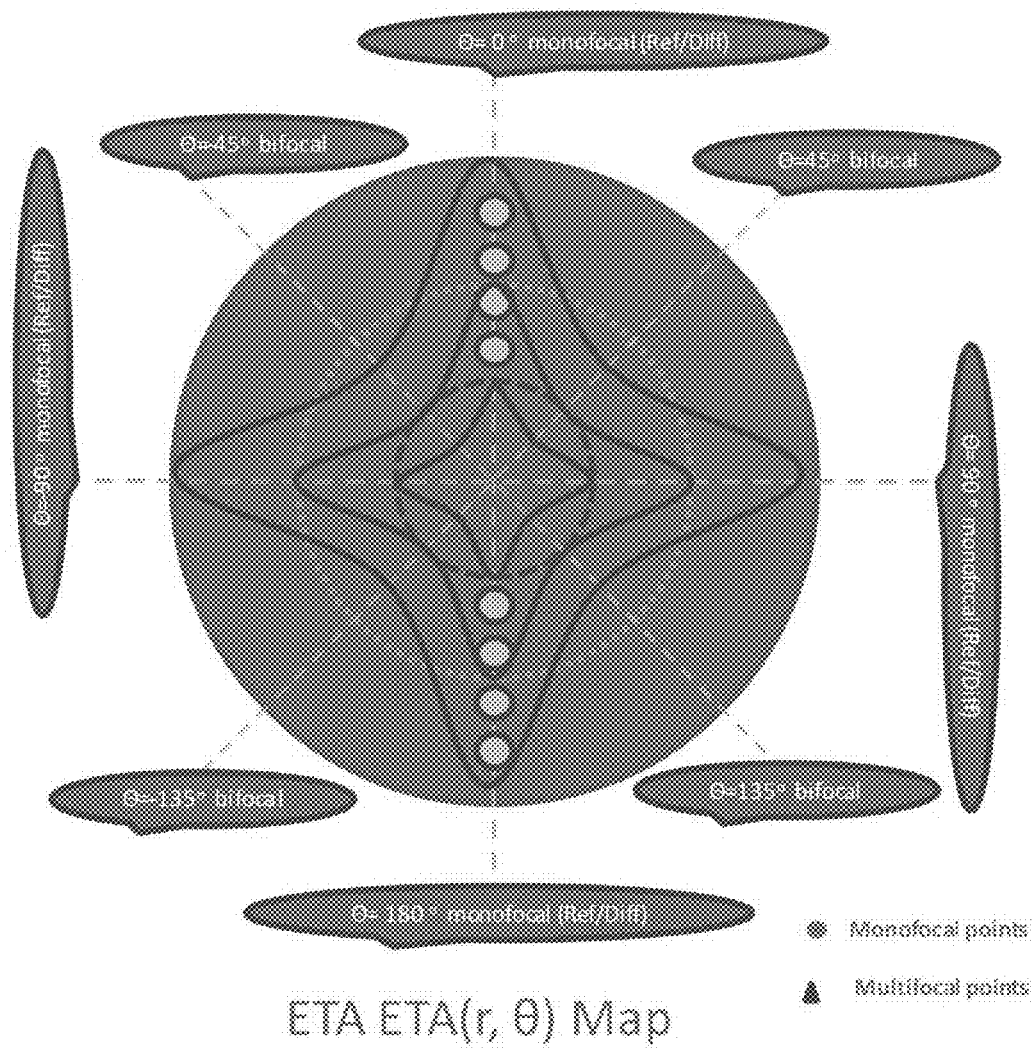
FIG. 10 is a diagram of an exemplary multi-focal lens ophthalmic apparatus that includes angularly-varying phase members in accordance with another illustrative embodiment.

FIG. 10 illustrates an example multi-focal intraocular lens 1000 configured with angularly varying phase members in accordance with an illustrative embodiment. As shown, the lens 1000 provides a mono-focal at corrective meridian Θ=0° and 180°. In addition, the lens 1000 provides a second mono-focal at corrective meridian Θ=90° and −90°. In addition, the lens 1000 provides a first bi-focal at Θ=−45° and 135°. In addition, the lens 1000 provides a second bi-focal at Θ=45° and −135°. In some embodiments, the lens is refractive. In other embodiments, the lens is diffractive.

Figure 11:
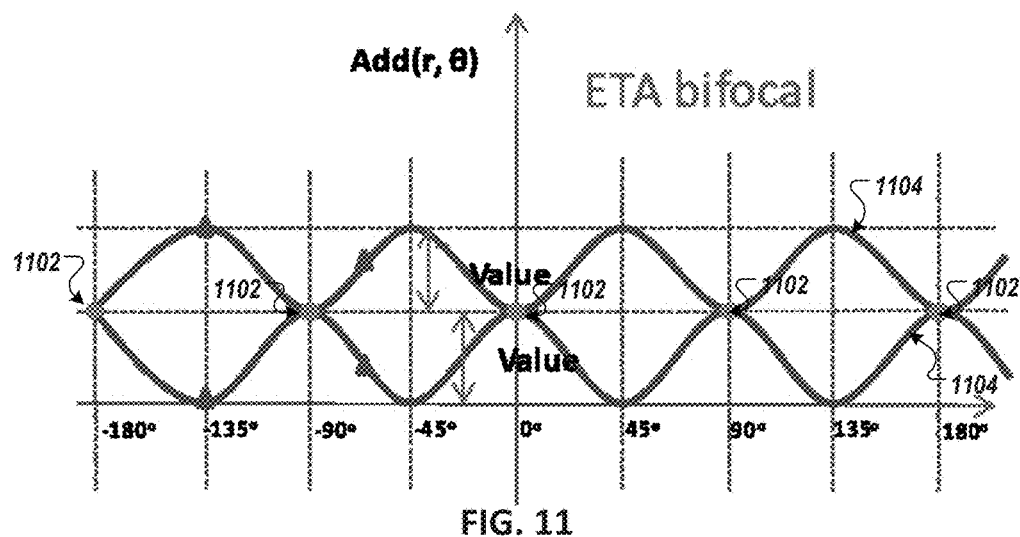
FIG. 11 is a diagram illustrating the multi-focal lens ophthalmic apparatus of FIG. 10 configured as a bifocal lens in accordance with another illustrative embodiment.
Figure 12:
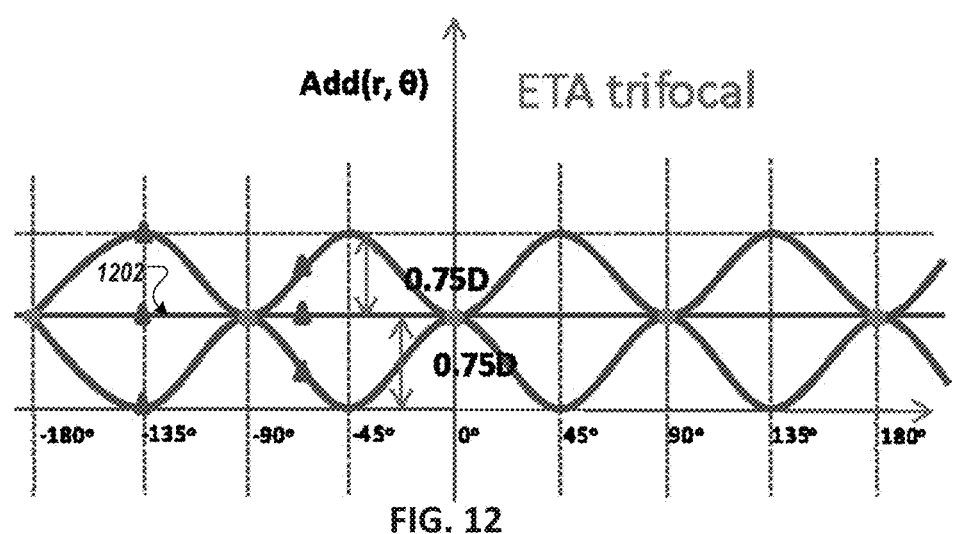
FIG. 12 is a diagram illustrating the multi-focal lens ophthalmic apparatus of FIG. 10 configured as a tri-focal lens in accordance with another illustrative embodiment.

With the angularly varying phase members, images at all meridians (Θ=0°, Θ=45°, Θ=90°, Θ=135°, Θ=180°, Θ=−135°, Θ=−90°, and Θ=−45°) reach a 20/20 "uncorrected distance visual acuity" (UDVA). FIGS. 11 and 12 are diagrams illustrating added cylindrical power, from the angularly varying phase members, in the radial and angular position in accordance with the illustrative embodiments.

FIG. 11 illustrates added cylinder power by the angularly varying phase members for a multi-focal intraocular lens configured as a bifocal. As shown in FIG. 11, for a given cylindrical power (e.g., 6.0 Diopters), the angularly varying phase members add varying magnitudes of cylinder powers between, e.g., 0.125 Diopters and 1.0 Diopter between the peak corrective meridian Θ=0° (e.g., the astigmatic meridian) and the non-peak corrective meridian Θ=45° in which minimum cylinder power is added at Θ=0° (where the meridian is a mono-focal, shown at points 1102), and in which the maximum cylinder power is added at Θ=45° where the meridian is configured as a bi-focal (shown along line 1104). The added power to the non-peak corrective meridian increases the tolerance of the IOL to misalignment from the corrective axis.

FIG. 12 illustrates a trifocal intraocular lens with the angularly varying phase members in accordance with an illustrative embodiment. As shown in FIG. 12, the added varying cylinder power is added between the peak corrective meridian Θ=0° and the non-peak corrective meridian Θ=45°, as shown in FIG. 11. As further shown, a trifocal optics 1202 is added. The trifocal 1202 does not have an angularly varying phase member.

Figure 13:
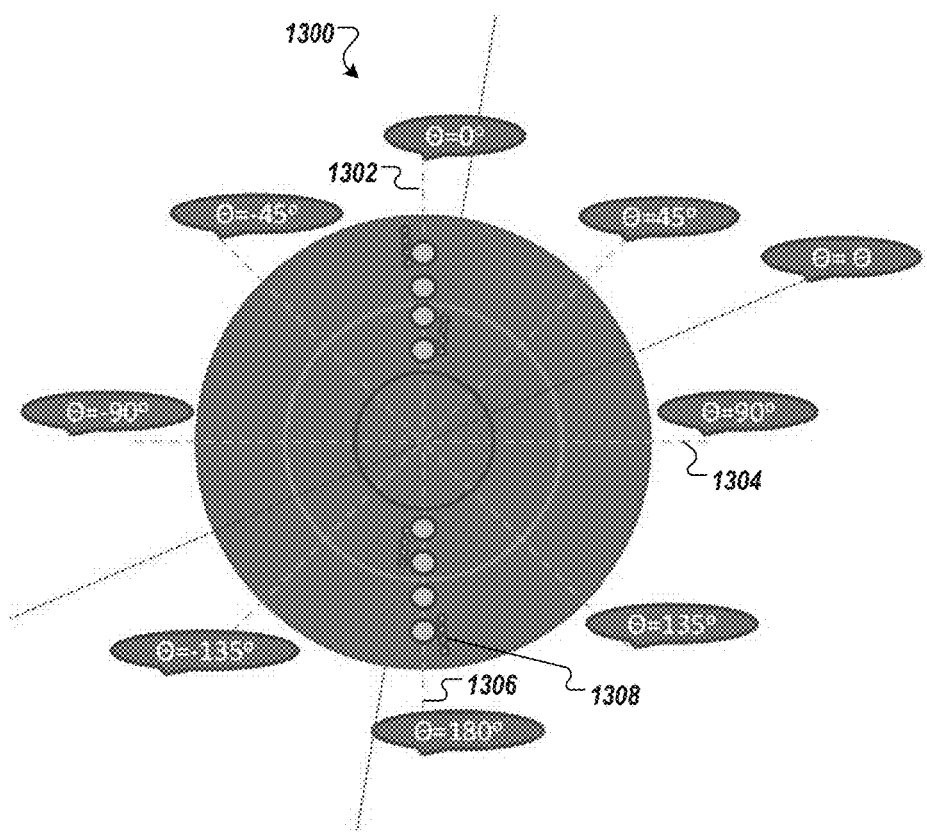
FIG. 13 is a diagram of an exemplary ophthalmic apparatus that includes angularly-varying phase members (refractive, diffractive, or both) in accordance with another illustrative embodiment.

FIG. 13 illustrates an ophthalmic apparatus 1300 having angularly varying phase members to extend tolerance of ocular astigmatism by varying extended depth of focus at each meridian through an optimized combination of angularly and zonally diffractive phase structure on each meridian in accordance with an illustrative embodiment.

As shown in FIG. 13, the ophthalmic apparatus 1300 includes a first corrective meridian 90° *N°±α° (variable 01), where a is the extended tolerance of the first corrective meridian, and N is an integer. For N=0, 1, 2, 3, 4, the meridians includes 0° (1302), ±90° (1304), and 180° (1306). In some embodiments, α is ±3°, ±3.25°, ±3.5°, ±3.75°, ±4°, ±4°, ±4.25°, ±4.5°, ±4.75°, ±5°, ±5.25°, ±5.5°, ±5.75°, ±6°, ±6.25°, ±6.5°, ±6.75°, ±7°, ±7.25°, ±7.5°, ±7.75°, ±8°, ±8.25°, ±8.5°, ±8.75°, ±9°, ±9.25°, ±9.5°, ±9.75°, and ±10°. Where a is ±10°, the IOL would have a dynamic and optimized efficiency for correcting astigmatic effects that can tolerate misalignment of the cylindrical axis up to 10 (variable 08) degrees in either counter clockwise or clockwise rotation. It is contemplated that terms noted as variables may be varied, modified, or adjusted, in some embodiments, to produce desired or intended effects and benefits, as discussed herein.

FIG. 14 illustrates a table for a trifocal IOL configured with the angularly varying phase members. As shown in FIG. 14, the light transmission efficiency at a first corrective foci 1402 (e.g., at the retina) is about 100% while other foci along the same meridian is about 0%. This configuration establishes the first corrective meridian 1402 at 0=0° and other meridians, e.g., θ=±90° and, e.g., 180°, as a monofocal with additional chromatic aberration reduction.

In addition, at meridian 45° *N°±α° (1408 and 1410) (variable 02), the light transmission efficiency varies for three point of focus (shown as 1408a, 1408b, and 1408c) (e.g., at the front of the retina, at the retina, and behind the retina) of the optics at this meridian. For N=1, 2, 3, 4, the meridians includes ±45° and ±90°. As shown in FIG. 14, at the first foci (1408a) (e.g., at the front of the retina), the light transmission efficiency is about 25% (variable 03), and the optics includes added power that matches the ocular astigmatic power corresponding to the human astigmatism tolerance level. At the second foci (1408b) (e.g., at the retina), the light transmission efficiency is about 50% (variable 04) efficiency. At the third foci (1408c) (e.g., behind the retina), the light transmission efficiency is about 25% (variable 05), and the optics include added power having the same magnitude as the first foci though with an opposite sign. At other meridians, the focus on the retina has efficiency between 0.5% and 100% (variable 06) and the other focus not on the retina has efficiency between 0% and 25% (variable 07). In some embodiments, the light transmission efficiency are varied via different materials that may be stacked, e.g., as a stacking lens, where each layer is comprised of a different material. In other embodiments, the angularly-varying phase members may be comprised of a material or materials that have a variation in refractive index, a gradient index, or a programmed index, for example liquid crystal which creates transmission efficiency change.

The thickness profile $T_1(r, \theta)$ for the IOL may be characterized by Equation 2 below.

$$T_1(r,\theta)=t_1(r)|\cos^2(\theta)|+t_2(r)|\sin^2(\theta)| \quad \text{(Equation 2)}$$

According to Equation 2, $t_1(r)$ and $t_2(r)$ are step heights for each zone, and they each matches an optical path difference (OPD) from $-2\lambda$ to $2\lambda$, where $\lambda$ is the design wavelength at zonal radius r.

Equation 2 may be simplified and represented as Equation 3, where A is adjusts the size of the extended operating band of the angularly varying phase member, and B provides an offset of the center of the angularly varying phase member with respect to a pre-defined reference frame (e.g., Θ=0° or Θ=90°, etc.).

$$T_1(r,\theta)=\cos[A\theta+B] \qquad \text{(Equation 3)}$$

Example: Angularly Varying Phase Members that Varies Along Angular Position

FIGS. 15-18, comprising, FIGS. 15A, 15B, 16A, 16B, 16C, 17A, 17B, 18A, 18B, and 18C, depict the ophthalmic apparatus with angularly varying phase members in accordance with other illustrative embodiments. According to these embodiments, the angularly varying phase members are located with a fixed-size zone and varies only along the angular position. In FIGS. 15A, 15B, 16B, 16C, 17A, 17B, 18B, and 18C, height profiles are illustrated via representative echelette elements for a diffractive surface.

Figures 15A, 15B:
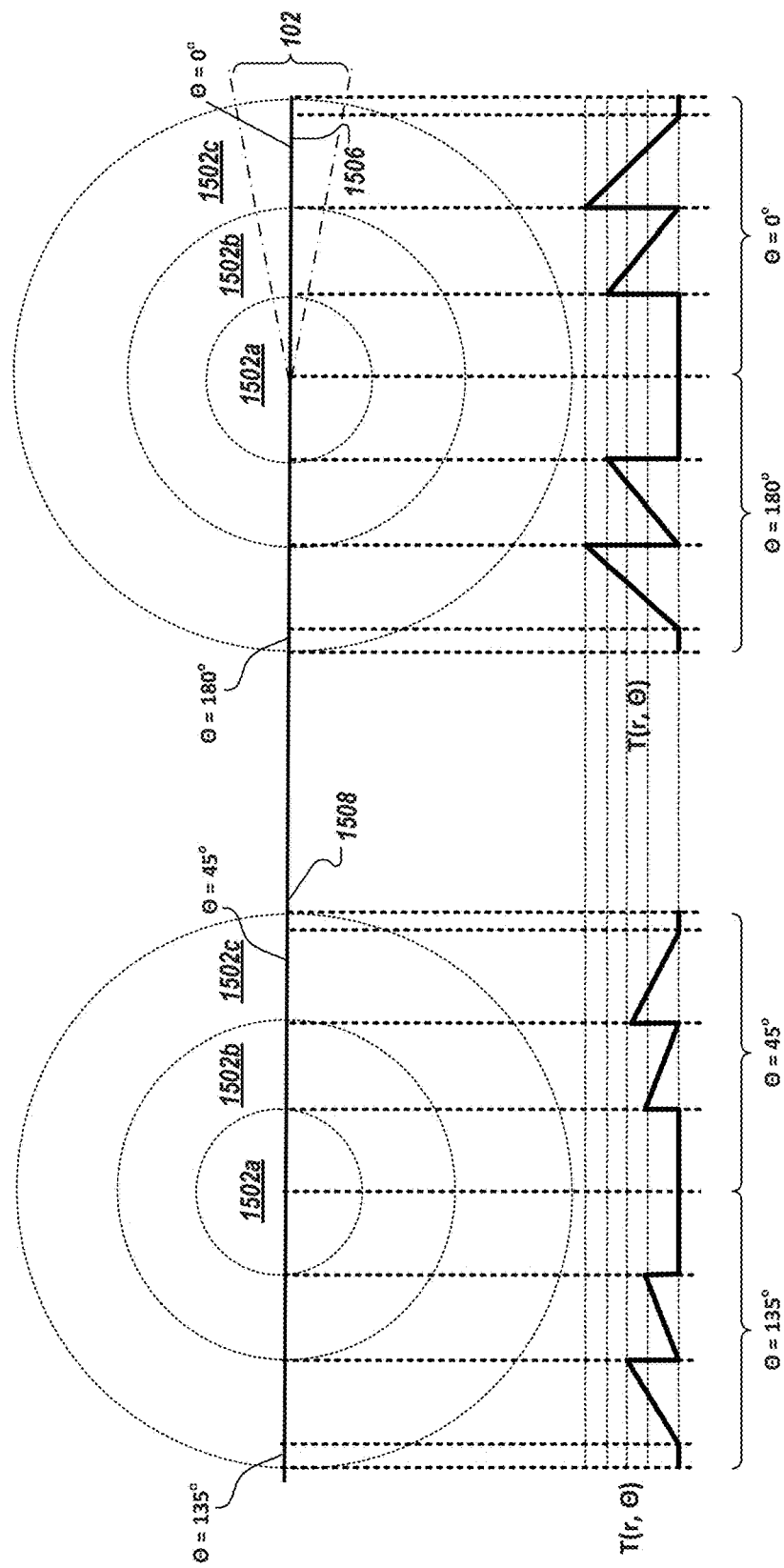
FIGS. 15A and 15B are diagrams of an exemplary ophthalmic apparatus that includes angularly-varying phase members with asymmetric height profiles in accordance with another illustrative embodiment.

As shown in FIGS. 15A-15B, the ophthalmic apparatus includes a plurality of zones 1502 (shown as 1502a, 1504b, and 1504c). The zones 1502a, 1502b, 1502c defined at a first corrective meridian θ=0° and 180° (1506) has approximately the same zone length (i.e., cylinder power) as the zones 1502a, 1502b, 1502c defined at a second meridian θ=45° and 135° (1508). As further shown in FIGS. 16A, 16B, and 16C, the height profile (shown as 1602, 1604, 1606, 1608, 1610, and 1612) of the face of the lens varies along the angular position θ=0°, θ=9°, θ=18°, θ=27°, θ=36°, and θ=45°.

FIGS. 17A and 17B illustrate an ophthalmic apparatus having a height profile across the multiple zones (shown as 1702a, 1702b, and 1702c) in which the height of the face of the lens angularly varies with the meridian axes. As shown in FIGS. 18A, 18B, and 18C, the height profile (shown as 1802, 1804, 1806, 1808, 1810, and 1812) of the face of the lens varies along the angular position θ=0°, θ=9°, θ=18°, θ=27°, θ=36°, and θ=45°.

Referring back to FIG. 13, in another aspect, the ophthalmic apparatus includes a plurality of alignment markings, including a first set of alignment markings 1302 and a second set of alignment markings 1304, that indicate the corrective meridian of the lens. In some embodiments, the first set of alignment markings 1302 is located at the meridian θ=0° and 180°. The second set of alignment markings 1304 may include corresponding sets of markets to define a tolerance band for the lens. In some embodiments, the second set of alignment markings 1304 is located at ±5° radial offset from the first set of alignment markings 1302.

Example: Refractive Lens Surfaces with Angularly Varying Phase Members

Figures 19A, 19B:
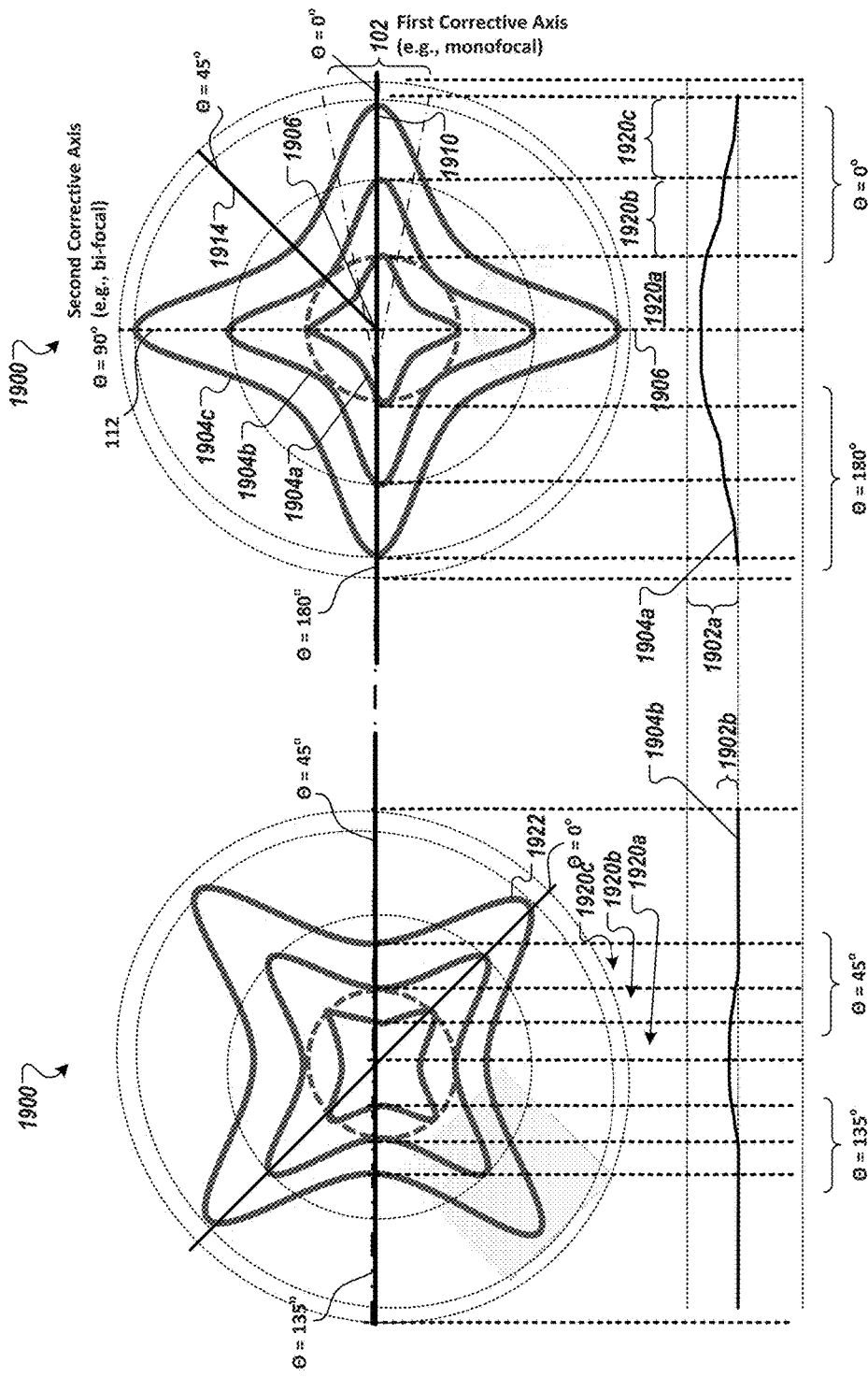
FIGS. 19A and 19B are diagrams of an exemplary ophthalmic apparatus that includes refractive angularly-varying phase members in accordance with another illustrative embodiment.

FIGS. 19A and 19B are diagrams of an exemplary ophthalmic apparatus 1900 that includes refractive angularly-varying phase members 102 in accordance with another illustrative embodiment. A height profile 1902 (shown as 1902a and 1902b) of the refractive surface 1904 (shown as 1904a and 1904b) is shown at θ=0° and θ=45°. As shown in FIG. 19A, the first height profile 1902a of the lens transitions into the second height profile 1904b. Here, the inflection point of the refractive surface is shown to vary spatially (i.e., changing radial values) and angularly (i.e., changing height or thickness values).

Figure 20E:
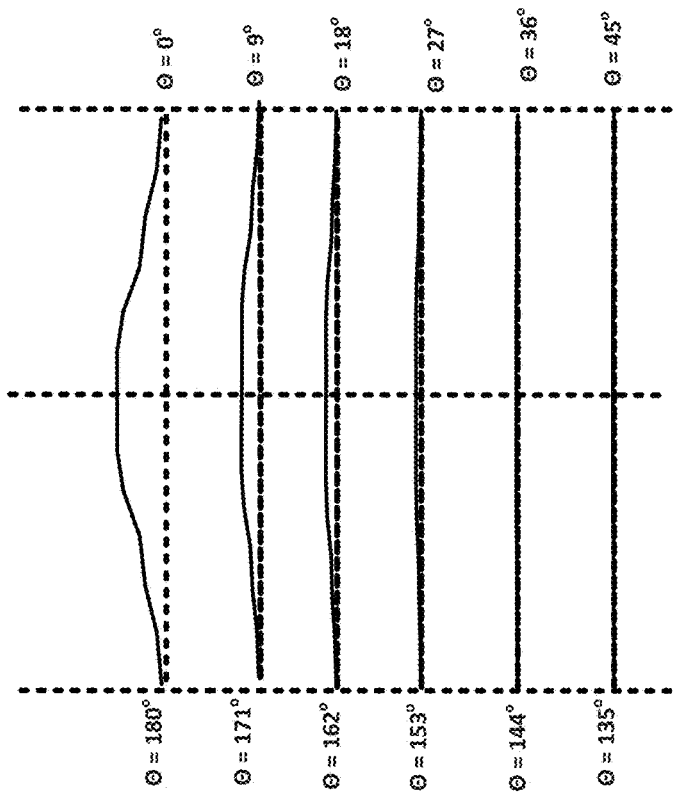

FIGS. 20A, 20B, 20C, 20D, and 20E illustrate a plurality of exemplary height profiles of the anterior or posterior face across the angularly phase members of the ophthalmic apparatus of FIGS. 19A-19B, in accordance with an illustrative embodiment. That is, the height profile is shown between the first high power meridian (at Θ=0°) and the operational edge of the angularly varying phase members (e.g., at Θ=±α, e.g., Θ=10° and Θ=−10°) in accordance with an illustrative embodiment. In FIG. 20B, representative height profiles at Θ=0° (2002); Θ=2° (2004); Θ=4° (2006); Θ=6° (2008); Θ=8° (2010); and Θ=10° (2012) (also shown in FIG. 20A) are provided as cross-sections of the echelette at the different meridians shown in FIG. 20A. As shown, the height profiles at axes nearby to the first high power meridian (e.g., between ±10°) have a similar shape, as the first high power meridian. The height profile varies in a continuous gradual manner (e.g., having a sine and cosine relationship) along the radial direction. This can be observed in FIGS. 20B and 20C. In FIG. 20B, the overall refractive profile is shown, and in FIG. 20C, an inflection point 2014 (e.g., shown as points 2014a, 2014b, 2014c, 2014d, 2014e, and 2014f) defined at a given zone boundary is shown. This transition of the inflection points 2014 may be described as a cosine-based or sine-based function, or a function derived from a combination thereof.

The thickness profile T1(r, θ) for the refractive design may be characterized by Equation 4 below.

$$T_1(r,\theta)=t_1(r)|\cos^2(\theta)|+t_2(r)|\sin^2(\theta)| \qquad \text{(Equation 4)}$$

According to Equation 4, $t_1(r)$ and $t_2(r)$ are the add power for each zone, and they each match optical power needs from −200D to +5.0D, for a design wavelength at zonal radius r.

FIG. 20C illustrates a first portion of the height profiles (near the optical axis) at Θ=0° (202); Θ=2° (204); Θ=4° (206); Θ=6° (208); Θ=8° (210); and Θ=10° (212) superimposed next to one another. This variation of the height profile along the radial axis provides a lens region that focuses light at the desired foci and other foci nearby. To this end, radial offset (i.e., misalignment) of the ophthalmic apparatus from the center axis of a desired corrective meridian results in its nearby regions focusing the light to the desired foci.

Figure 20D:
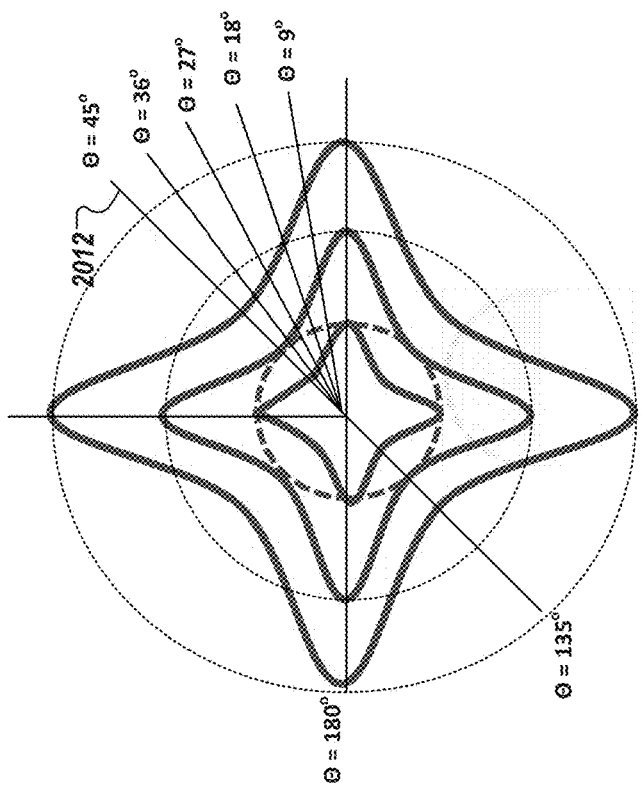

In FIGS. 20D and 20E, example height profiles of the lens surface between Θ=0° and Θ=45° are shown. As shown in FIGS. 20D and 20E, the height profiles of the angularly varying phase member vary as a cosine-based or sine-based function. In some embodiments, the height profiles of the lens surface between Θ=45° and Θ=90° are mirrored at Θ=45° to the lens surface between Θ=0° and Θ=45°.

It is contemplated that refractive angularly varying phase member can vary symmetrically or asymmetrically, for a given zone, as well as between the multiple zones, as described, for example, in relation to FIGS. 8, 9, 16, and 18. That is, inflection points in the refractive surface at a given zone (e.g., a first zone) may vary, in the radial and angular direction, at the same rate with inflection points in the refractive surface at another zone (e.g., a second zone), as described in relation to the diffractive element of FIG. 8. In addition, in some embodiments, inflection points in the refractive surface at a given zone (e.g., a first zone) may vary, in the radial and angular direction, at a different rate with inflection points in the refractive surface at another zone (e.g., a second zone), as described in relation to the diffractive element of FIG. 9. In addition, in some embodiments, inflection points in the refractive surface at a given zone (e.g., a first zone) may vary, only in the angular direction, at a same or different rate with inflection points in the refractive surface at another zone (e.g., a second zone), as described in relation to the diffractive element of FIGS. 16 and 18.

Example: Multi-Focal Refractive Ophthalmic Apparatus with Diffractive or Refractive Angularly Varying Phase Members FIG. 21, comprising FIGS. 21A, 21B, and 21C, is a diagram illustrating an exemplary ophthalmic apparatus 2100 that includes refractive or diffractive angularly-varying phase members 102, in accordance with another illustrative embodiment.

The angularly-varying phase member 102, in FIG. 21, can be characterized as Equation 5, where r(θ) is the contour radius for the given meridian added power A(θ), wavelength λ, zone number n, and the scaling value s(θ), all at meridian θ.

$$r(\theta) = \sqrt{2 \cdot n \cdot \frac{s(\theta) \cdot \lambda}{A(\theta)}} \quad \text{(Equation 5)}$$

In FIG. 21A, the lens 2100 provides a mono-focal at corrective meridian Θ=0° and 180°. In addition, the lens 2100 provides a second mono-focal at corrective meridian Θ=90° and −90°. In some embodiments, the mono-focal corrective meridian Θ=0° and 180° and the mono-focal corrective meridian Θ=90° and −90° have the same focal point. In other embodiments, the mono-focal corrective meridian Θ=0° and 180° and the mono-focal corrective meridian Θ=90° and −90° have different focal points.

Referring still to FIG. 21A, the lens 2100 provides a first bi-focal at Θ=−45° and 135° and, in addition, the lens 2100 provides a second bi-focal at Θ=45° and −135°. In some embodiments, the bi-focal corrective meridian −45° and 135° and the bi-focal corrective meridian Θ=45° and −135° have the same focal point. In other embodiments, the bi-focal corrective meridian −45° and 135° and the bi-focal corrective meridian 45° and −135° have different focal points.

As shown in FIG. 21B, intraocular lens 2100 has a base cylindrical power (e.g., 6.0 Diopters) to which angularly varying phase members having additional cylindrical power are added. The angularly varying phase members adds the cylindrical power having an extended tolerance of operation, for example, up to ±10° (of misalignment) from a given corrective meridian (e.g., an astigmatism meridian). As shown, the additional cylindrical power are added to a surface sag coordinate (shown as "sag(z)"). Specifically, the added cylindrical power (shown as "Value θ" in FIG. 21B), for each given angular position θ (2104), in this exemplary lens design, varies between about −200 Diopters and about −0.01 Diopters (shown as "Value θ" 2104) and between about 0.01 Diopters and about 6.0 Diopters (shown as "Value θ" 2106). The added power is provided over the surface of the intraocular lens having a diameter 2108 of 6.0 mm (millimeters). Radial positions 2114 (shown as 2114a and 2114b) are illustratively shown in FIGS. 21A and 21B. As shown in FIG. 21C, the added cylindrical power, along each radial positions (e.g., at Θ=−180° to Θ=180°), at radial positions 2114a and 2114b are provided.

Referring still to FIG. 21B, the added cylindrical power of 0.01 Diopters and about 6.0 Diopters and of −200 Diopters and about −0.01 Diopters is added via a refractive surface 2110 (e.g., as shown having an "ETA(r, θ) surface profile"). As shown in FIG. 21B, the refractive surface 2110 has a modified thickness value at sag surface value of "0" at the center of the lens. The sag surface value, as shown, decreases to generate the refractive surface profile, as for example, described in relation to FIG. 4D. It should be appreciated that the provided sag surface profile is merely illustrative. It is contemplated that equivalent refractive surfaces may be produced on various lens surface in additive or subtractive manner, as shown, for example, but not limited to, in relation to FIGS. 4A-4D.

Referring still to FIG. 21B, the added cylindrical power profile 2112 may be used to provide distant vision and emmetropia correction for a given patient. Emmetropia generally refers to a state in which the eye is relaxed and focused on an object more than 20 feet away in which light coming from the focus object enters the eye in a substantially parallel, and the rays are focused on the retina without effort. To this end, image at all meridian can reach 20/20 "uncorrected distance visual acuity" (UDVA).

Referring to back to FIG. 21A, the added cylindrical power profile 2112 of FIG. 21B is added at angular position Θ=Θ° (shown as "Θ=Θ° 2116"). To this end, the angularly varying phase members, as described herein, for example, including those described in relation to FIGS. 1-2, 7-9, and 15-20 may be applied at any angular position along the lens surface, to generate a multi-focal lens.

Referring still to FIG. 21A, in some embodiment, a complementary angularly varying phase member may be added in a given quadrant of the lens. For example, an intraocular lens may include a first angularly varying phase member at an angular position between Θ=45° and Θ=90°; the intraocular lens may include a second angularly varying phase member at an angular position between Θ=0° and Θ=45° in which the second angularly varying phase member is mirrored, along the axis Θ=45°, with respect to the first angularly varying phase member.

Example: Alignment Markings for Extended Tolerance Band

Figure 22A:
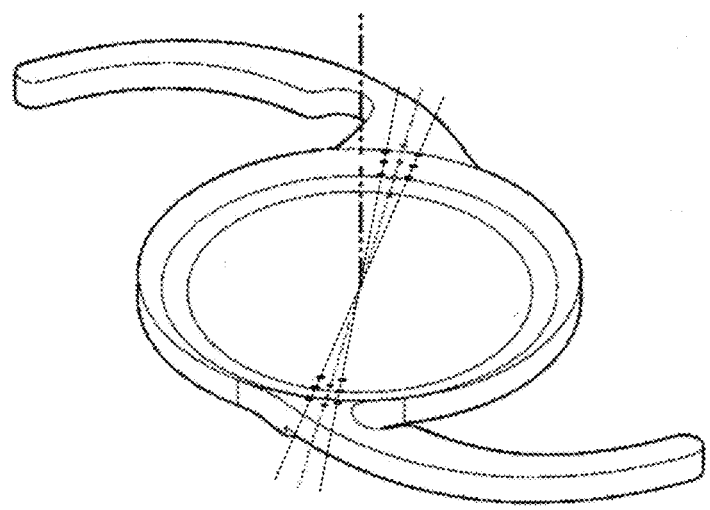
FIGS. 22A and 22B are diagrams illustrating a top and bottom view of an ophthalmic apparatus of FIGS. 15A-15B with extended tolerance band markers in accordance with an illustrative embodiment.
Figure 22B:
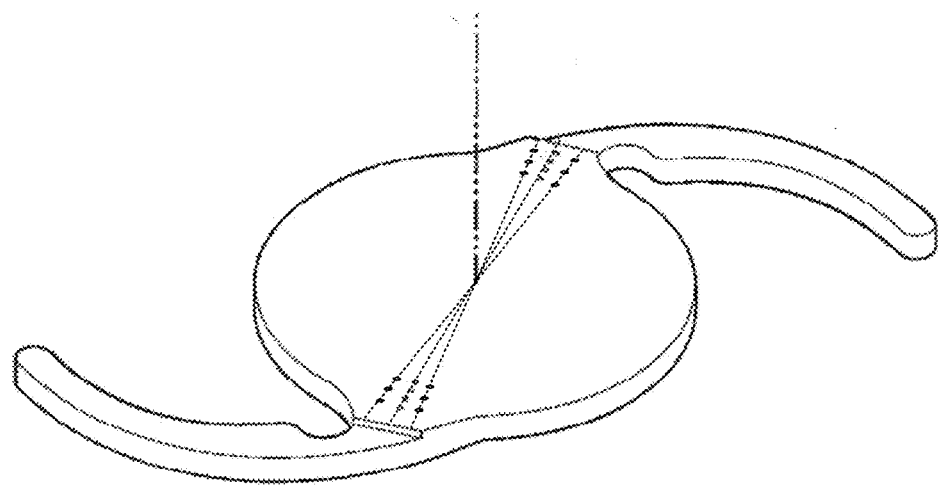

FIGS. 22A and 22B depicts an ophthalmic apparatus with an extended tolerance astigmatic band. The ophthalmic apparatus includes the second set of alignment markings 1308 as discussed in relation to FIG. 13.

Example Method of Generating Surfaces with Angularly-Varying Phase Members

Figure 23:
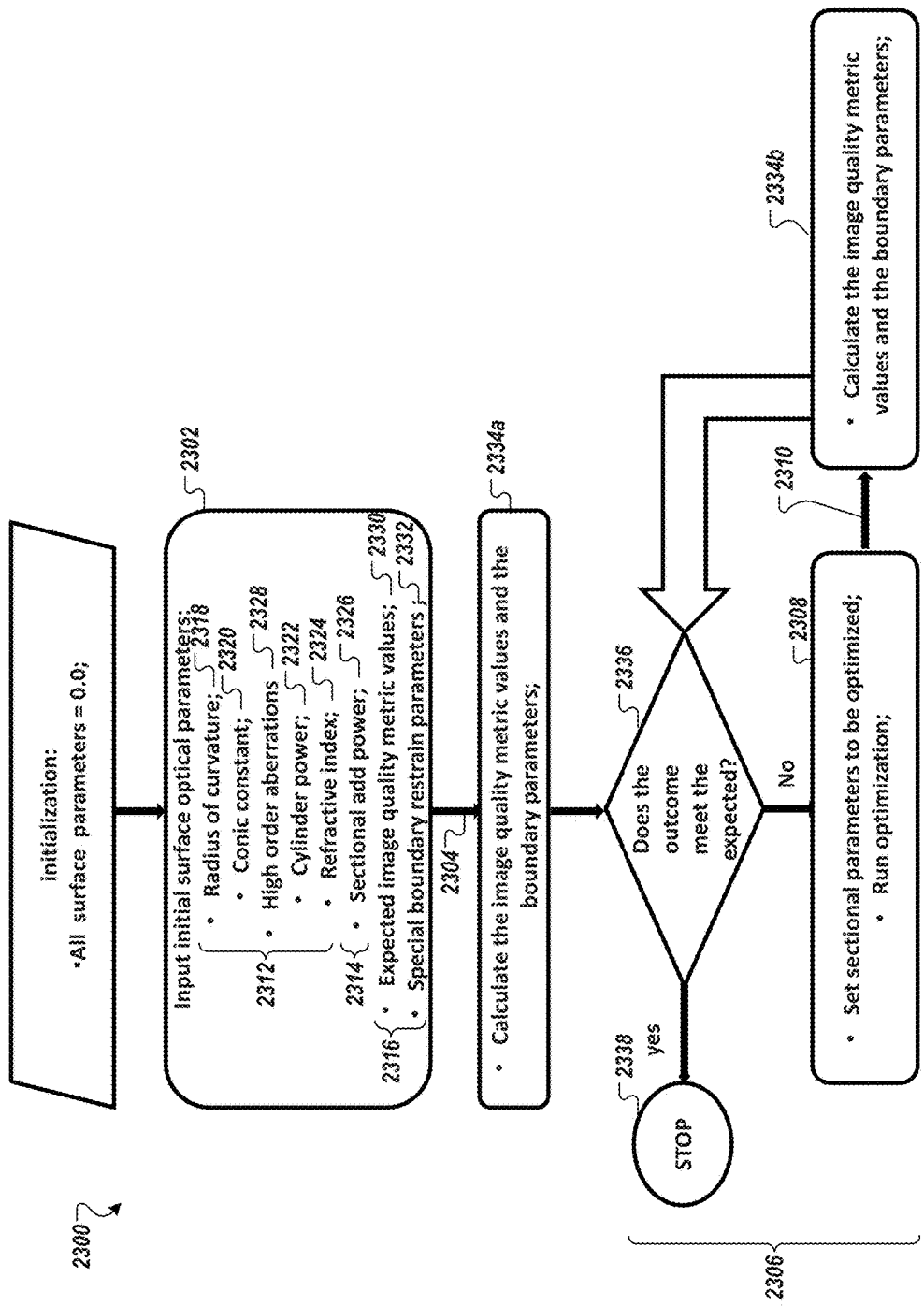
FIG. 23 is diagram of a method to generate, via a processor, the surface with the angularly-varying phase members, in accordance with an illustrative embodiment.

FIG. 23 is diagram of a method 2300 to generate, via a processor, the surface with the angularly-varying phase members, in accordance with an illustrative embodiment. As shown in FIG. 23, the method 2300 includes generating (2302), via a processor, an initial design (2304) comprising a base surface (with base cylindrical power) and sectional enhancements (with added cylindrical power) and iteratively generating (2308) and evaluating, a revised design (2310), generated according to an optimization routine (2308) that is performed based on sectional parameters, until pre-defined image quality metric values and boundary parameter are achieved. The sectional enhancements power of the initial design and the iterative design is the surface with the angularly-varying phase members.

Referring still to FIG. 23, the method 2300 includes generating (2302) a first design (2304) via i) initial surface optical parameter, including a) base surface optical parameters 2312 and b) sectional surface optical parameters 2314, and ii) the pre-defined image quality metric values 2316. The base surface optical parameters 2312 include, in some embodiments, parameters associated with a radius of curvature for the toric lens (shown as "Radius of curvature" 2318), parameters associated with conic constant and aspheric coefficients (shown as "Conic constant" 2320), parameters associated with base cylinder power (shown as "Cylinder power" 2322), and parameters associated lens and/or coating material characteristics such as refractive index (shown as "Refractive index" 2324). Other parameters may be used as part of the base surface optical parameters 2312. The section surface optical parameters 2314, in some embodiments, includes parameters associated with sectional added power and meridian characteristics (shown as "Sectional add power" 2328) and parameters associated with high order aberration characteristics, e.g., Zernike aberrations above second-order (shown as "High order aberrations" 2328).

Referring still to FIG. 23, the parameters associated with the sectional added power 2326, in some embodiments, include a cylindrical power, for a given optical zone. In some embodiments, the cylindrical power for the added power are all refractive, all diffractive, or a combination of both. The parameters associated with the high order aberration characteristics 2328, in some embodiments, include polynomial values (e.g., based on Zernike polynomials, Chebyshev polynomials, and combinations thereof) or characteristics such as polynomial orders and types as well as meridian boundaries for the high order aberrations. The high order aberration is constraint, e.g., from minimum to maximum cylindrical power over one or more meridian sections. In some embodiments, the high order aberrations is constraint or designated to a meridian, e.g., that corresponds to a corneal irregular geometry or limited retinal area functions. Such customization has a potential to truly benefit patients having cornea with or without astigmatism, patients with local Keratoconus with or without astigmatism, patients with glaucoma, patients with retinal macular degeneration (AMD), and the like.

Referring still to FIG. 23, the parameters associated with the pre-defined image quality metric value 2316 includes parameters associated with expected image quality metric (shown as "Expected image quality metric values" 2330) and parameters associated with special boundary restrain parameters (shown as "Special boundary restrain parameters" 2332). In some embodiments, image quality metric is based a comparison of a base polychromatic diffraction MTF (modular transfer function) (e.g., tangential and sagittal) to a number of error polychromatic diffraction MTFs values, e.g., where one or more polychromatic diffraction MTFs are determined for one or more misalignments of the generated toric lens from its intended operating meridians, e.g., at 5-degree misalignment and at 10-degree misalignment.

Referring still to FIG. 23, the initial design (2304) is evaluated (2334a) to determine image quality metric values (e.g., the base polychromatic diffraction MTF, e.g., at 0 degree misalignment) and the error polychromatic diffraction MTFs, e.g., at the 5 and 10 degrees misalignment) and boundary parameters. The determined image quality metric values are evaluated (2336) to determine whether the image quality metric values and boundary parameters meet an expected outcome, e.g., a value of 0.2. In some embodiments, the expected outcome is whether there is no cut off through spatial frequency beyond 100 cpd. Upon determining that the condition is met, the method 2300 is stop (2338). It is contemplated that other image quality metrics may be used, e.g., the optical transfer function (OTF), phase transfer function (PhTF), and etc.

Where the condition is not met, the method 2300 adjusts (2308) sectional parameters to be optimized and rerun the optimization to generate the revised design 2310. In some embodiments, the adjusted sectional parameters may include power $A(\theta)$, wavelength $\lambda$, zone number n, and the scaling value $s(\theta)$, as for example, shown in FIGS. 19A-19B, 20A-20E, 21A-21C, which is expressed as $$r(\theta) = \sqrt{2 \cdot n \cdot \frac{s(\theta) \cdot \lambda}{A(\theta)}},$$

where $r(\theta)$ is the contour radius for the given meridian added power $A(\theta)$, wavelength k, zone number n, and the scaling value $s(\theta)$, all at meridian $\theta$.

Referring back to FIG. 23, the method 2300 then includes evaluating (2334b) the revised design 2310 to determine image quality metric values (e.g., the base polychromatic diffraction MTF, e.g., at 0 degree misalignment) and the error polychromatic diffraction MTFs, e.g., at the 5 and 10 degrees misalignment) and boundary parameters, as discussed in relation to step 2334a, and re-evaluating (2336) whether the revised image quality metric values and boundary parameters meet the expected outcome, as discussed in relation to step 2336.

In some embodiments, the method 2300 is performed in an optical and illumination design tool such as Zemax (Kirkland, Wash.). It is contemplated that the method 2300 can be performed in other simulation and/or design environment.

Figure 24:
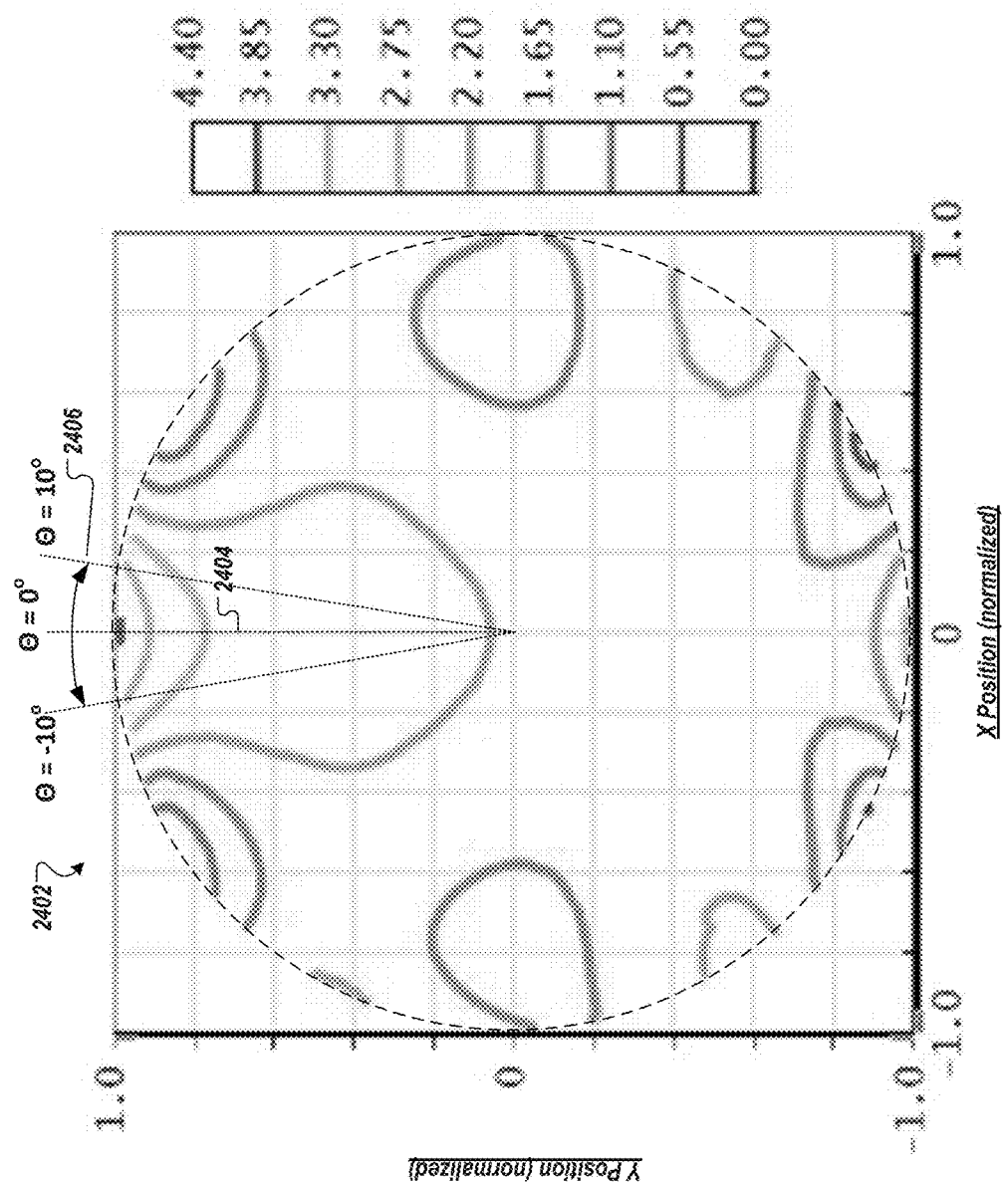
FIG. 24 is a diagram of an example freeform-polynomial surface area that provides extended rotational tolerance, in accordance with an illustrative embodiment.

Ophthalmic Apparatus Having Extended Tolerance Band with Freeform Refractive Surfaces FIG. 24 is a diagram of an example freeform-polynomial surface area 2402 that provides extended rotational tolerance, in accordance with an illustrative embodiment. The freeform-polynomial surface area 2402 is mapped to a surface of an ophthalmic apparatus 324 (not shown—see FIG. 4) to provide cylinder power to the ophthalmic apparatus, e.g., for the correction an astigmatism, or the like, such that the ophthalmic apparatus can be subjected to a cylindrical axis misalignment (CAM) (shown via arrow 2406) of the meridian 2404 (also referred to as "axis' 2404) of up to 10 degrees without degradation of the corrective performance (e.g., with regard to visual acuity (VA) or modular transfer function (MTF)), as compared to when there no misalignment.

Notably, the freeform-polynomial surface area 2402 is defined as a mathematical expression that is a combination of one or more polynomial expressions each having a distinct complex orders. Examples of polynomial expressions includes, but are not limited to, Chebyshev-based polynomial expression, Zernike-based polynomial expression. The combination of one or more polynomial expressions may be used to define an angularly-varying phase member that is tolerant of cylindrical axis misalignment (CAM) up to an extended band of operation without degradation of the corrective performance such as visual acuity (VA) or modular transfer function (MTF) as compared to when there no misalignment.

In some embodiments, one or more polynomial expressions are combined with different complex orders and the results are tested to determine that corrective performance (e.g., with regard to visual acuity (VA) or modular transfer function (MTF) are met.

As used herein, a "Chebyshev-based polynomial" refers to a mathematical expression that is expressed as a combination of one or more Chebyshev polynomial components in which the Chebyshev polynomial components is a Chebyshev polynomials of the first kind and/or a Chebyshev polynomials of the second kind. The Chebyshev polynomial can include, as a combination, the Chebyshev polynomial component along with another polynomial expression (e.g., Zernike polynomials, combinations of Zernike polynomials, other polynomials, or combination thereof, and etc.)

As used herein, a "Zernike-based polynomial" refers to a mathematical expression that is expressed as a combination of one or more Zernike polynomial components in which the Zernike polynomial components is a Zernike polynomial. The Zernike polynomial can include, as a combination, a Zernike polynomial component along with another polynomial expression (e.g., Chebyshev polynomials, combinations of Chebyshev polynomials, other polynomials, or combination thereof, and etc.)

Referring back to FIG. 24, the freeform-polynomial surface area 2402 of FIG. 24 is defined as a mathematical expression that is a combination of one or more polynomial expressions each having a distinct complex orders. In some embodiments, the freeform-polynomial surface area 2402 is defined as a second thickness value T(x,y) for a cylinder surface superimposed on a first thickness value (e.g., a base or typical aspheric height profile), in which T(x, y) is defined by Equation 6:

$$T(x,y)=\{c(i,j)*\cos(i*\arccos(t))*\cos(j*\arccos(t))\} \quad \text{(Equation 6)}$$

where $c(i, j)$ is a coefficient based on i and j, which are each orders of the polynomial and expressed as integers, x and y are spatial locations on the freeform-polynomial surface area, and t is a normalized parameter for angular positions having values between $-1.0$ and $1.0$. The base thickness value can be from a typical aspheric thickness profile. In some embodiments, the coefficient $c(i,j)$ is based on a basis function that adjust the normalized amplitudes of each respective location of the lens as represented by the Chebyshev polynomial. A Chebyshev polynomial (of the first kind), along one dimension, can be expressed as $T_k(x)=\cos(k*\cos^{-1}(x))$, where k is an order that is an integer. In two dimension, a Chebyshev polynomial (of the first kind) can be expressed as $T_{i,j}(x, y)=\cos(i*\cos^{-1}(x))*\cos(j*\cos^{-1}(y))$, where x and y values have a numerical value between $-1.0$ and $+1.0$, and Tij are normalized to a value of $-1.0$ and $+1.0$.

Referring still to FIG. 24, the freeform-polynomial surface area 2402 of FIG. 24 is derived from Chebyshev polynomials as shown in Equation 6 having i-order of 0 to 6 and a j-order of 0 to 6. Equation 7 shows the expanded mathematical expression for the second freeform-polynomial surface area 2402 of FIG. 24.

$$\begin{aligned}T(x, y) = &\; c(0, 0)*\cos(0*\cos^{-1}(t))*\cos(0*\cos^{-1}(t)) + \\ &\; c(0, 1)*\cos(0*\cos^{-1}(t))*\cos(1*\cos^{-1}(t)) + \\ &\; c(0, 2)*\cos(0*\cos^{-1}(t))*\cos(2*\cos^{-1}(t)) + \\ &\; c(0, 3)*\cos(0*\cos^{-1}(t))*\cos(3*\cos^{-1}(t)) + \\ &\; c(0, 4)*\cos(0*\cos^{-1}(t))*\cos(4*\cos^{-1}(t)) + \\ &\; c(0, 5)*\cos(0*\cos^{-1}(t))*\cos(5*\cos^{-1}(t)) + \\ &\; c(0, 6)*\cos(0*\cos^{-1}(t))*\cos(6*\cos^{-1}(t)) + \\ &\; c(1, 0)*\cos(1*\cos^{-1}(t))*\cos(0*\cos^{-1}(t)) + \\ &\; c(1, 1)*\cos(1*\cos^{-1}(t))*\cos(1*\cos^{-1}(t)) + \\ &\; c(1, 2)*\cos(1*\cos^{-1}(t))*\cos(2*\cos^{-1}(t)) + \\ &\; c(1, 3)*\cos(1*\cos^{-1}(t))*\cos(3*\cos^{-1}(t)) + \end{aligned} \quad \text{(Equation 7)}$$

-continued
$$\begin{aligned}&\; c(1, 4)*\cos(1*\cos^{-1}(t))*\cos(4*\cos^{-1}(t)) + \\ &\; c(1, 5)*\cos(1*\cos^{-1}(t))*\cos(5*\cos^{-1}(t)) + \\ &\; c(1, 6)*\cos(1*\cos^{-1}(t))*\cos(6*\cos^{-1}(t)) + \\ &\; \ldots c(6, 0)*\cos(6*\cos^{-1}(t))*\cos(0*\cos^{-1}(t)) + \\ &\; c(6, 1)*\cos(6*\cos^{-1}(t))*\cos(1*\cos^{-1}(t)) + \\ &\; c(6, 2)*\cos(6*\cos^{-1}(t))*\cos(2*\cos^{-1}(t)) + \\ &\; c(6, 3)*\cos(6*\cos^{-1}(t))*\cos(3*\cos^{-1}(t)) + \\ &\; c(6, 4)*\cos(6*\cos^{-1}(t))*\cos(4*\cos^{-1}(t)) + \\ &\; c(6, 5)*\cos(6*\cos^{-1}(t))*\cos(5*\cos^{-1}(t)) + \\ &\; c(6, 6)*\cos(6*\cos^{-1}(t))*\cos(6*\cos^{-1}(t)) = \\ &\; c(0, 0) + c(0, 1)*\cos(\cos^{-1}(t)) + \\ &\; c(0, 2)*\cos(\cos(2*\cos^{-1}(t)) + c(0, 3)*\cos(3*\cos^{-1}(t)) + \\ &\; c(0, 4)*\cos(4*\cos^{-1}(t)) + c(0, 5)*\cos(5*\cos^{-1}(t)) + \\ &\; c(0, 6)*\cos(6*\cos^{-1}(t)) + c(1, 0)*\cos(\cos^{-1}(t))* + \\ &\; c(1, 1)*\cos(\cos^{-1}(t))*\cos(\cos^{-1}(t)) + \\ &\; c(1, 2)*\cos(\cos^{-1}(t))*\cos(2*\cos^{-1}(t)) + \\ &\; c(1, 3)*\cos(\cos^{-1}(t))*\cos(3*\cos^{-1}(t)) + \\ &\; c(1, 4)*\cos(\cos^{-1}(t))*\cos(4*\cos^{-1}(t)) + \\ &\; c(1, 5)*\cos(\cos^{-1}(t))*\cos(5*\cos^{-1}(t)) + \\ &\; c(1, 6)*\cos(\cos^{-1}(t))*\cos(6*\cos^{-1}(t)) + \\ &\; \ldots c(6, 0)*\cos(6*\cos^{-1}(t))*\cos(0*\cos^{-1}(t)) + \\ &\; c(6, 1)*\cos(6*\cos^{-1}(t))*\cos(1*\cos^{-1}(t)) + \\ &\; c(6, 2)*\cos(6*\cos^{-1}(t))*\cos(2*\cos^{-1}(t)) + \\ &\; c(6, 3)*\cos(6*\cos^{-1}(t))*\cos(3*\cos^{-1}(t)) + \\ &\; c(6, 4)*\cos(6*\cos^{-1}(t))*\cos(4*\cos^{-1}(t)) + \\ &\; c(6, 5)*\cos(6*\cos^{-1}(t))*\cos(5*\cos^{-1}(t)) + \\ &\; c(6, 6)*\cos(6*\cos^{-1}(t))*\cos(6*\cos^{-1}(t)) \end{aligned}$$

Referring still to FIG. 24, a power pupil map with uniformly distributed contour lines of the calculated cylindrical power for the freeform-polynomial surface area 2402 is shown. The corrective meridian is located at about $\Theta=0°$ (shown as axis 104) with a center portion of the freeform-polynomial surface area 2402 being disposed at this $\Theta$ position. Off-center structures of the freeform-polynomial surface area 2402 extend from the center structure in a gradually varying manner (e.g., as defined by the combination of Chebyshev polynomials described in relation to Equation 7) to apply cylinder power to a band of meridians surrounding the corrective meridian enabling the ophthalmic apparatus to operate off-axis (or off-meridian) to the corrective meridian (e.g., the astigmatism meridian). Notably, there are no more than 0.6-Diopter difference between any neighboring uniformly distributed contour lines.

Figure 25:
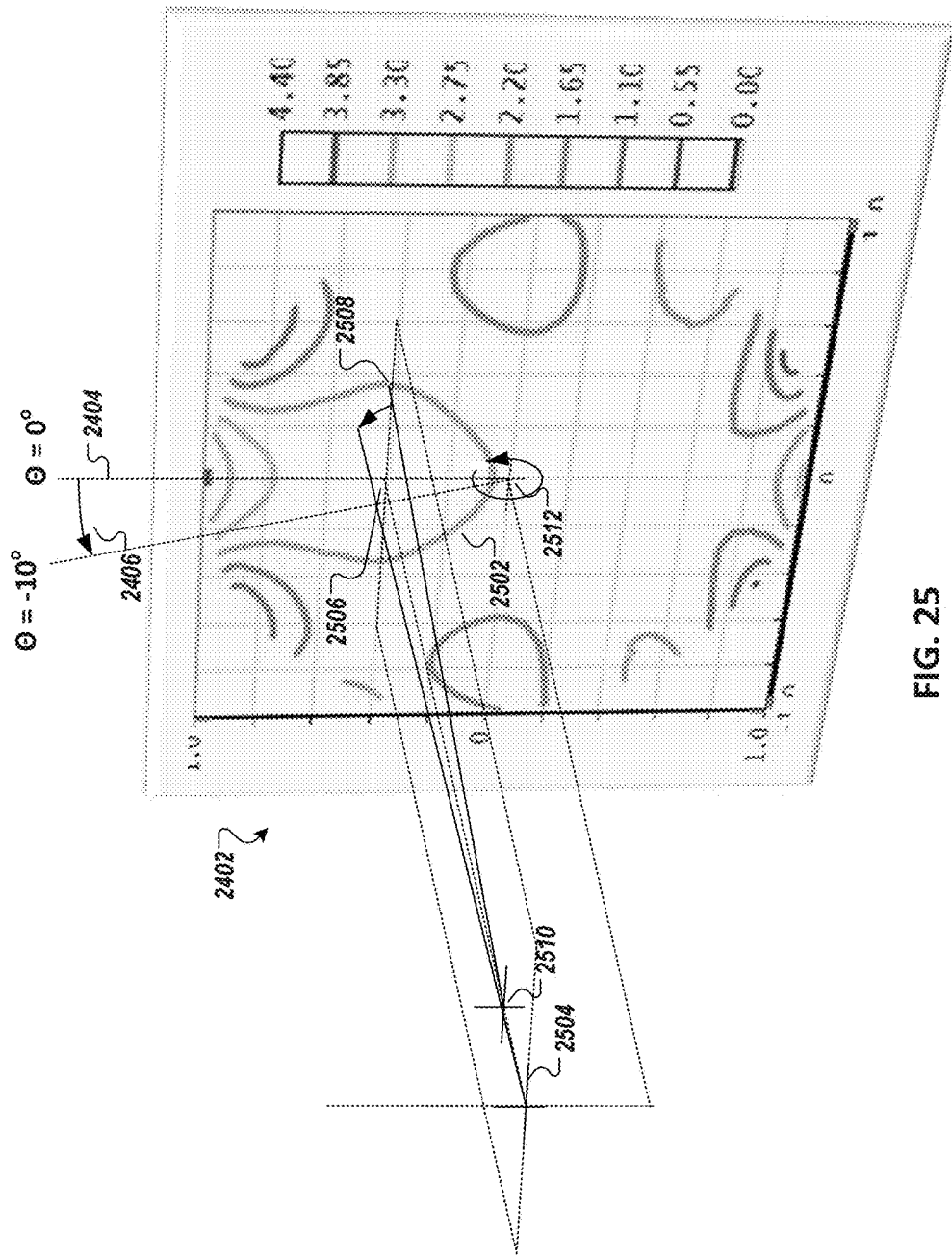
FIG. 25 illustrates an example operation of the freeform-polynomial surface area of FIG. 24 when subjected to misalignment, in accordance with an illustrative embodiment.

FIG. 25 illustrates an example operation of the freeform-polynomial surface area of FIG. 24 when subjected to misalignment, in accordance with an illustrative embodiment. The freeform-polynomial surface area 2402, as a diffractive or refractive structure, in some embodiments, varies the extended depth of focus to a plurality of nearby focus points. To this end, light directed to such nearby focus points are thus directed to the desired focus point when the ophthalmic apparatus is subjected to a rotational offset from a primary intended axis of alignment, thereby extending the rotational tolerance of the apparatus to an extended tolerance band. In FIG. 25, a portion (2502) of the freeform-polynomial surface area 2402 has a focus point 2504 (e.g., referred to as a "main focus point" 2504, e.g., to correct for an astigmatism) that is generated by a region about the center 2506 of the portion 2502 of the freeform-polynomial surface area 2402. In this example, a nearby region 2508 of that portion 2502 has a focus point 2510 (e.g., referred to as an "auxiliary focus point" 2510) that is offset from the main focus point 2504. When the freeform-polynomial surface area 2402 is rotated about axis 2512, e.g., as misalignment 2402 is introduced to the corrective meridian $\Theta=0°$ (2404), the focus point 2510 of region 2508 is moved towards the main focus point 2504, thereby extending the band of operation of the freeform-polynomial surface area 2402. Remarkably, this extended tolerance astigmatism band delivers cylinder power to correct for the astigmatism for a range of meridians (e.g., up to $\pm 10°$ as shown in FIG. 24, though can be more in other embodiments), thereby eliminating any need for additional corrective measures (e.g., supplemental corrective devices or another surgical intervention) when the implanted ophthalmic apparatus is not perfectly aligned to the desired astigmatism meridian in the eye.

Put another way, the freeform-polynomial surface area 2402 facilitates an extended band of the corrective meridian that has minimal, and/or clinically acceptable, degradation of the visual acuity and modulation transfer function when the ophthalmic apparatus is subjected to rotational misalignment between the astigmatic axis and a center axis of the corrective meridian.

Corneal Irregular Geometry or Limited Retinal Area Functions

In another aspect, the freeform-polynomial surface area 2402 of FIG. 24 is optimized to purposely place accumulated high surface amplitude to non-functional retinal area so that the functional areas can fully benefit the enhanced image quality stability of the freeform-polynomial surface design. Examples of non-functional retinal areas may include, but not limited to, areas of gradual loss of sight (e.g., associated with glaucoma or retinal macular degeneration (e.g., age-related macular degeneration, AMD). The freeform-polynomial surface area 2402 of FIG. 24 can be similarly optimized to emphasize needs for a cornea that irregularly shaped with or without astigmatism and with local Keratoconus with or without astigmatism.

In particular, the freeform-polynomial surface area 2402, in some embodiments, are optimized by further modification of the weights (e.g., c(i,j) as discussed in relation to Equation 6 or Equation 7) in the combined Chebyshev polynomials and the Zernike or extended polynomials used to characterize or design the geometry of the freeform-polynomial surface area 2402. As noted above, the c(i,j) is used to scale the normalized surface generated by the Chebyshev polynomials or the Zernike polynomials. C(i,j) is also used to adjust and/or emphasize cylindrical power for corneal irregular geometry or limited retinal area functions.

As shown in Equations 6 and 7, the freeform-polynomial surface area 2402 is defined by a surface sag (or power) that is a weighted sum of Chebyshev polynomials (Zernike and other polynomials may be used with, or in substitute of, the Chebyshev polynomials) with the coefficient c(i, j) (e.g., shown in Equation 6).

The coefficient c(i, j) are weights that may be modified or set based on specific knowledge of the local coordinates of the special cornea irregularity. To this end, the coefficient c(i, j) allows the specific polynomials to be freely shifted in space (i.e., spatial) domain to match the local coordinates. The coefficient c(i, j) as weights for each polynomial can be a function of local coordinates function and implemented as a filter with low-, medium-, or high-pass transmission operations.

Results of IOL with Exemplified Freeform-Polynomial Surfaces

Figure 26:
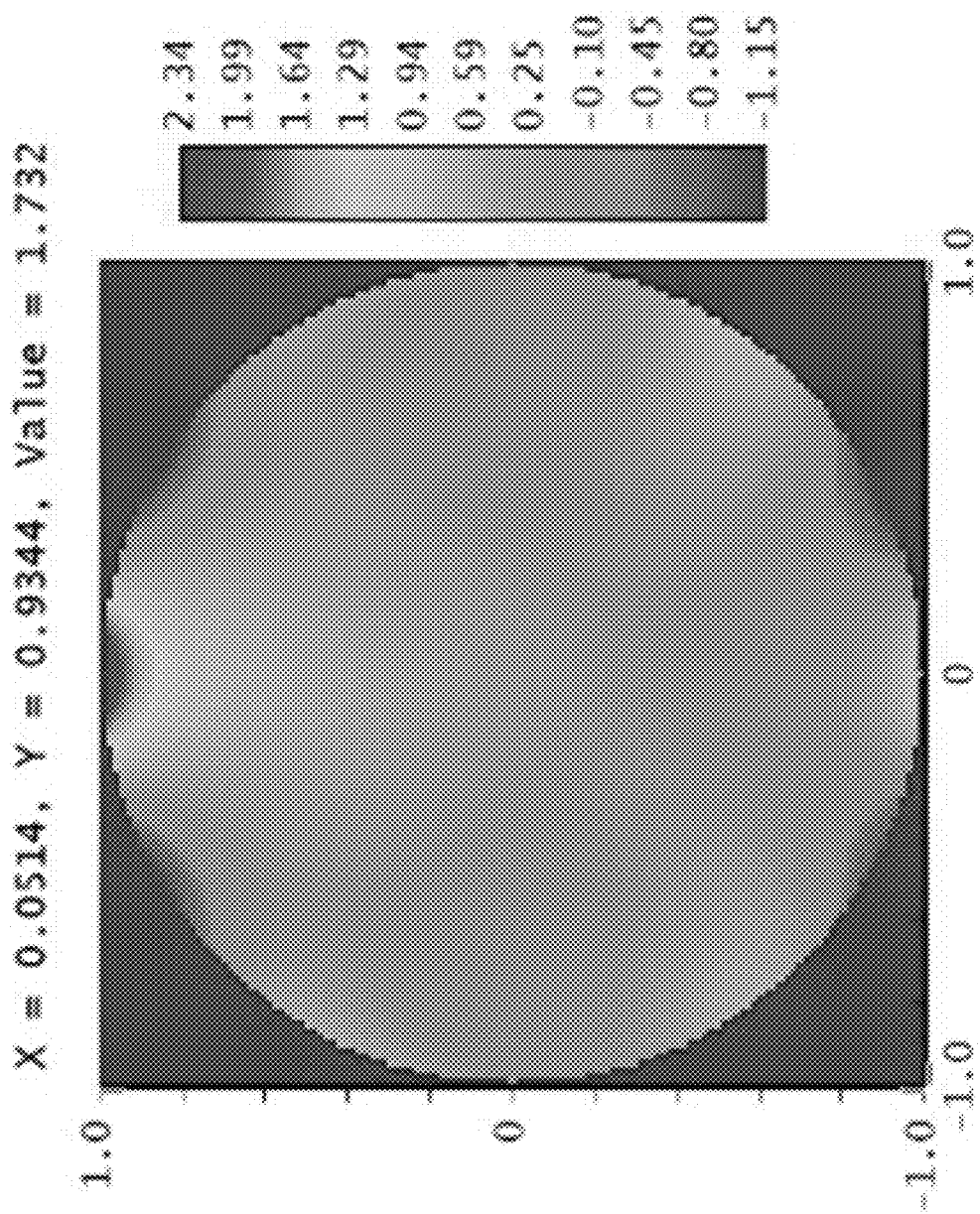
FIG. 26 shows a combined cylinder map generated from the combination of the IOL cylindrical power (provided, in part, via the freeform-polynomial surface) combined with the corneal cylindrical power through meridians.

FIG. 26 shows a combined cylinder map generated from the combination of the IOL cylindrical power (provided, in part, via the freeform-polynomial surface) combined with the corneal cylindrical power through meridians. As discussed above with reference to FIG. 24, and as can be seen from the IOL cylinder map through meridians around the clock, there is remarkably no more than about 0.6D difference for any continuous uniformly distributed contour lines at the IOL plane. The IOL SE is 20D at the IOL plane. The IOL cylinder map of FIG. 24 is combined with the IOL SE to provide the overall IOL cylindrical map. This overall IOL cylindrical map is then combined with a test corneal cylindrical power. The resulting combination (shown in FIG. 26) remarkably shows little variation in the cylinder map of the combined IOL cylindrical power the corneal cylindrical power. That is, the astigmatism associated with test corneal cylindrical power has been attenuated and/or corrected for by the IOL cylindrical power provided, in part, by the freeform-polynomial surface.

Figure 27A:
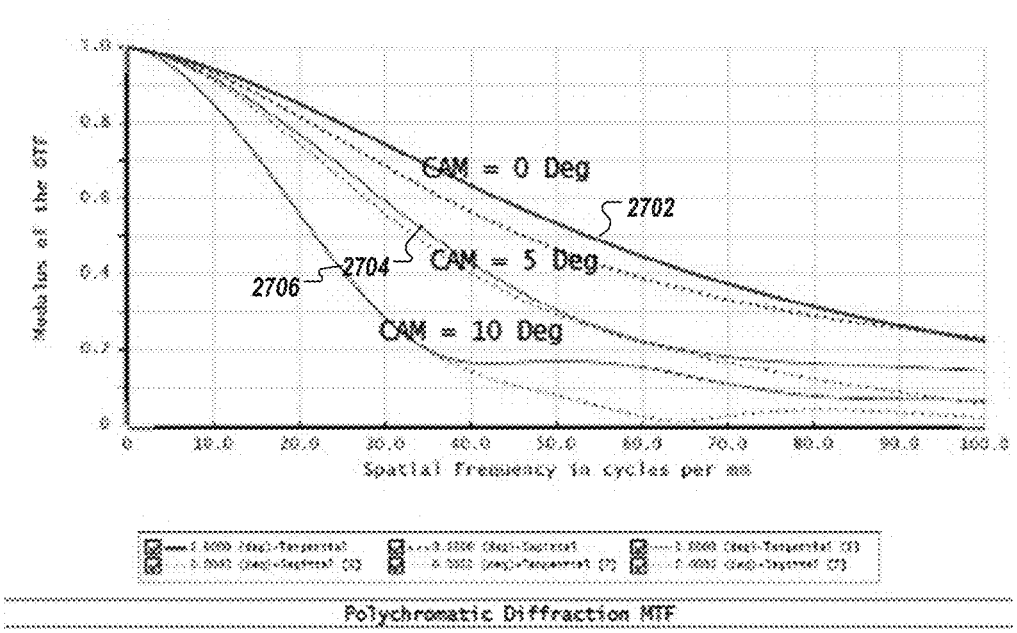
FIGS. 27A and 27B each shows calculated MTF values as spatial frequencies of an exemplified IOL in a physiological eye model with astigmatic cornea in different cylindrical axis misalignment (CAM) situations between the cornea and the IOL for an iris pupil.
Figure 27B:
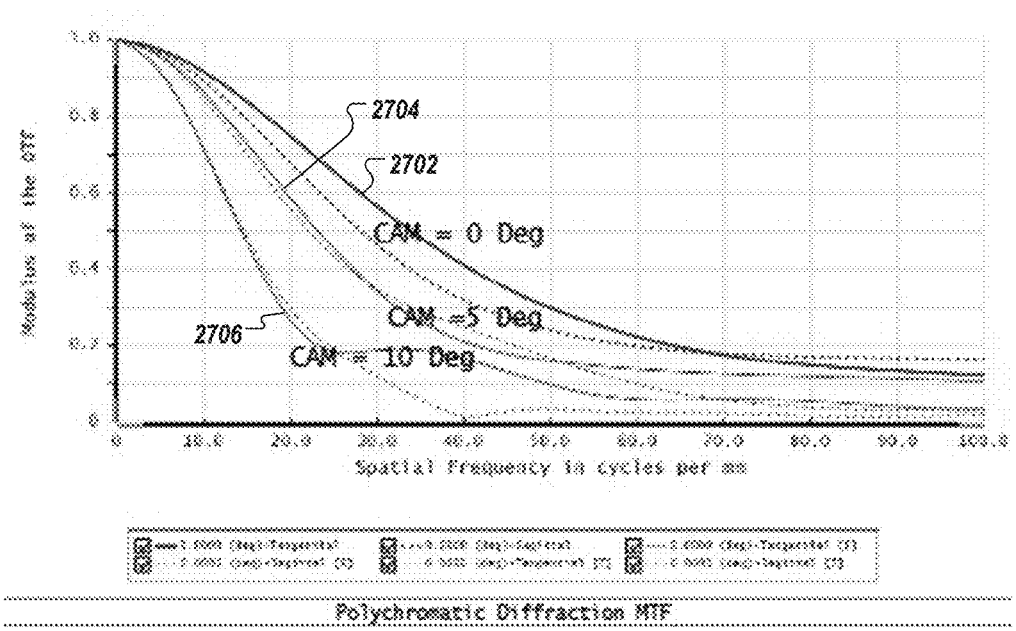

FIGS. 27A and 27B each shows calculated MTF values as spatial frequencies of an exemplified IOL in a physiological eye model with astigmatic cornea in different cylindrical axis misalignment (CAM) situations between the cornea and the IOL for an iris pupil. Notably, as shown in FIGS. 27A and 27B, the modulation transfer function (MTF) is maintained across the extended range of alignment for a lens configured with the freeform-polynomial surface area 2402 of FIG. 24. Specifically, in FIGS. 27A and 27B, the MTFs for misalignment at 0 degrees, 5 degrees, and 10 degrees are shown (shown as "CAM=0 Deg" 2702, "CAM=5 Deg" 2704, and "CAM=10 Deg" 2706). In FIG. 27A, the iris pupil is about 3.0 mm. In FIG. 27B, the iris pupil is about 5.0 mm.

Notably, as can also be seen from the MTF curves, there are no cut-offs of the spatial frequency beyond 100 cpd (cycles per degree), which for an IOL with SE (Spherical Equivalent) of 20D (Diopters), this spatial frequency is approximately 30 cpd.

Example of Multi-Zonal IOL with the Exemplified Freeform-Polynomial Surfaces

In another aspect, a multi-zonal IOL with freeform-polynomial surfaces is disclosed. In some embodiments, the multiple zonal structure includes one or more zonal surfaces defines by Chebyshev-based polynomials while other zonal surfaces are defined by other polynomials (e.g., Zernike and Chebyshev polynomials).

Figure 28A:
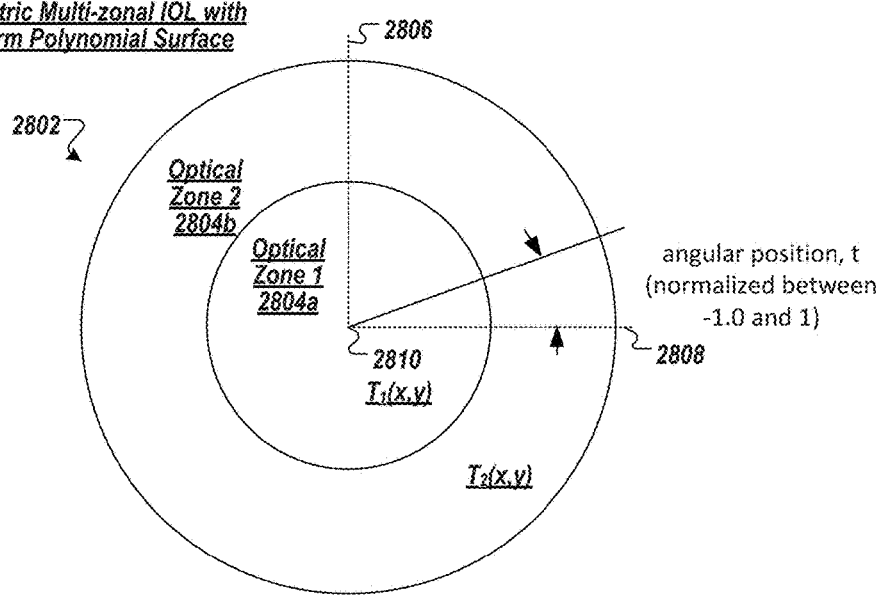
FIG. 28A shows a diagram of a freeform-polynomial surface area (e.g., the second or third height profile) of a second optical zone that symmetrically spans part of the optical face of the apparatus, in accordance with an illustrative embodiment.

In some embodiments, the freeform-polynomial surface area (e.g., the second or third height profile) symmetrically spans part of the optical face of the apparatus). FIG. 28A shows a diagram of a freeform-polynomial surface area (e.g., the second or third height profile) of a second optical zone that symmetrically spans part of the optical face of the apparatus, in accordance with an illustrative embodiment.

As shown in FIG. 28A, the ophthalmic apparatus includes an optical face 2802 (e.g., the portion of the face surface of the ophthalmic apparatus that include corrective optical structures) that includes the one or more optical zones 2804

(shown as "optical zone 1" 2804*a* and "optical zone 2" 2804*b*). The first zone of the optical face has a boundary defined by a first axis 2806 of the face and a second axis 2808 of the face (e.g., wherein the first axis is orthogonal to the second axis), and each of the x-spatial locations at value −1.0 and at value 1.0 is located at a first radial position along the first axis between a center location 2810 of the ophthalmic apparatus and the boundary, and each of the y-spatial locations at value −1.0 and at value 1.0 is located at the first radial position along the second axis between the center location of the ophthalmic apparatus and the boundary. As shown, the "optical zone 1" 2804*a* has a first T(x,y) height profile (e.g., as described in relation to Equation 6) that is superimposed over, e.g., the base or typical aspherical height profile. In some embodiments, the "optical zone 1" 2804*a* has a surfaces defined by other polynomials (e.g., Zernike, or combination of Zernike and Chebyshev polynomials).

In some embodiments, the second "optical zone 2" 2804*b* is characterized by a third height profile $T_2(x,y)$ (e.g., an extra height profile associated with cylinder power) superimposed on a first height profile (e.g. a base or typical aspheric height profile), the third height profile being defined as:

$$T_2(x,y) = \Sigma\{c_2(i_2,j_2) * \cos(i_2 * \arccos(t_2)) * \cos(j_2 * \arccos(t_2))\} \quad \text{(Equation 8)}$$

where $c_2(i_2, j_2)$ is a coefficient based on $i_2$ and $j_2$, which are each integers (e.g., ranging between 0 and 10), x and y are spatial locations on the second freeform-polynomial surface area and has values between −1.0 and 1.0, and $t_2$ is a normalized parameter having values between −1.0 and 1.0 (e.g., associated with the intended correction meridian). In some embodiments, the "optical zone 2" 2804*b* has a surfaces defined by other polynomials (e.g., Zernike, or combination of Zernike and Chebyshev polynomials).

In some embodiments, the freeform-polynomial surface area (e.g., the second or third height profile) asymmetrically spans part of the optical face of the apparatus. That is, the first zone of the optical face has a boundary defined by a first axis of the face and a second axis of the face (e.g., wherein the first axis is orthogonal to the second axis). Each of the x-spatial locations at value −1.0 and at value 1.0 is located at a first radial position along the first axis between a center location of the ophthalmic apparatus and the boundary, and each of the y-spatial locations at value −1.0 and at value 1.0 is located at a second radial position along the second axis between the center location of the ophthalmic apparatus and the boundary, where the first radial position and the second radial position are different.

Figure 28B:
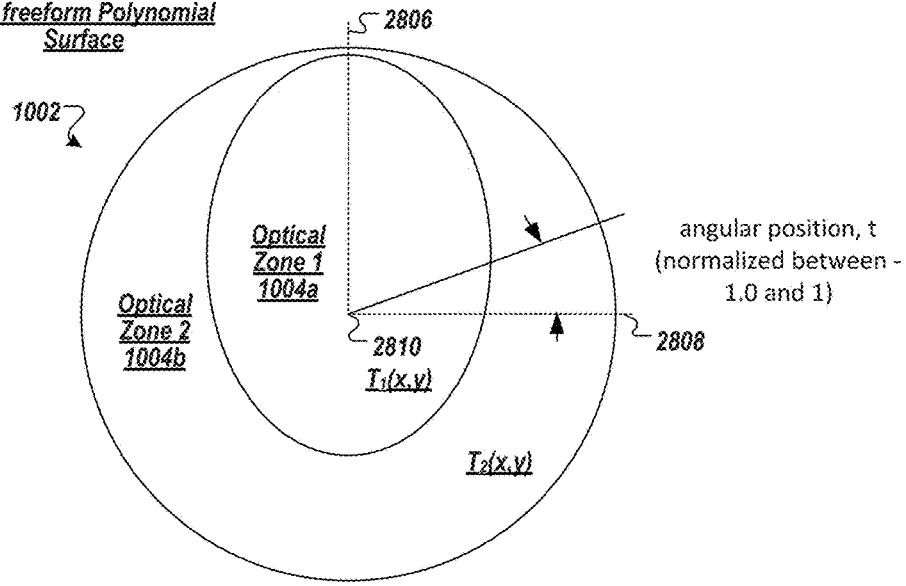
FIG. 28B shows a diagram of a freeform-polynomial surface area (e.g., the second or third height profile) of a second optical zone that symmetrically spans part of the optical face of the apparatus, in accordance with an illustrative embodiment.

FIG. 28B shows a diagram of a freeform-polynomial surface area (e.g., the second or third height profile) of a second optical zone that symmetrically spans part of the optical face of the apparatus, in accordance with an illustrative embodiment.

As shown in FIG. 28B, the ophthalmic apparatus includes the optical face 2802 (e.g., the portion of the face surface of the ophthalmic apparatus that include corrective optical structures) that includes the one or more optical zones 28004 (shown as "optical zone 1" 2804*a* and "optical zone 2" 2804*b*) that are asymmetric one another. The first zone of the optical face has a boundary defined by a first axis 2806 of the face and a second axis 2808 of the face (e.g., wherein the first axis is orthogonal to the second axis), and each of the x-spatial locations at value −1.0 and at value 1.0 is located at a first radial position along the first axis between a center location 2810 of the ophthalmic apparatus and the boundary, and each of the y-spatial locations at value −1.0 and at value 1.0 is located at the first radial position along the second axis between the center location of the ophthalmic apparatus and the boundary. As shown, the "optical zone 1" 2804*a* has a first T(x,y) height profile (e.g., as described in relation to Equation 1) that is superimposed over, e.g., the base or typical aspherical height profile. In some embodiments, the "optical zone 1" 2804*a* has a surfaces defined by other polynomials (e.g., Zernike, or combination of Zernike and Chebyshev polynomials).

In some embodiments, the second "optical zone 2" 2804*b* is characterized by a third height profile $T_2(x,y)$ (e.g., as described in relation to Equation 7) that are each superimposed over, e.g., the base or typical aspherical height profile. In some embodiments, the "optical zone 2" 2804*b* has a surfaces defined by other polynomials (e.g., Zernike, or combination of Zernike and Chebyshev polynomials).

It is contemplated that other zone shapes may be used for a given zone of the multiple zones. Example of other zone shape include, but not limited to, a rectangle, diamond, and various freeform polygons.

Referring back to FIG. 23, the diagram also shows a method to generate, via a processor, the freeform-polynomial surface area of FIG. 24, in accordance with an illustrative embodiment. As shown in FIG. 23, the method includes generating (2302), via a processor, an initial design (2304) comprising a base surface (with base cylindrical power) and sectional enhancements for freeform-polynomial surface area—with added cylindrical power derived from the Chebyshev-based polynomial expression, Zernike-based polynomial expression—and iteratively generating (2306) and evaluating, a revised design (2310), generated according to an optimization routine (2308) that is performed based on sectional parameters, until pre-defined image quality metric values and boundary parameter are achieved. The sectional enhancements power of the freeform-polynomial surface area initial design and the iterative freeform-polynomial surface area design are the ETA polynomial surface of FIG. 24.

Referring still to FIG. 23, the parameters associated with the sectional added power 2326 for the freeform-polynomial surface area, in some embodiments, include a mathematical expression comprising a combination of one or more polynomial expressions (e.g., Chebyshev-based polynomial expression, Zernike-based polynomial expression, etc.) each having a distinct complex orders. In some embodiments, the cylindrical power for the added power are all refractive. The parameters associated with the high order aberration characteristics 1128, in some embodiments, include polynomial values (e.g., based on Zernike polynomials, Chebyshev polynomials, and combinations thereof) or characteristics such as polynomial orders and types as well as meridian boundaries for the high order aberrations. The high order aberration is constrained, e.g., from minimum to maximum cylindrical power over one or more meridian sections. In some embodiments, the high order aberrations is constrained or designated to a meridian, e.g., that corresponds to a corneal irregular geometry or limited retinal area functions. In other embodiments, the high order aberrations may be introduced as weights a freeform polynomial weights to form the freeform-polynomial surface area. In such embodiments, the high order aberrations and its meridian locations on the lens surface may be optimized prior to the freeform polynomial weights being determined to facilitate a customized design that is tailored for a given patient (i.e., particularly in view of corneal irregular geometry or limited retinal area functions). Such customization has a potential to truly benefit patients having cornea with or without astigmatism, patients with local Keratoconus with or without astigmatism, patients with glaucoma, patients with retinal macular degeneration (AMD), and the like.

The adjusted sectional parameters (e.g., 2308) may include adjusting values for i and j of the Chebyshev or Zernike polynomials, as discussed in reference to Equation 6 or Equation 7. In some embodiments, only one value of i or j of the Chebyshev or Zernike polynomials is adjusted to generate each design variant. In other embodiments, the values of i and j of the Chebyshev or Zernike polynomials are adjusted concurrently.

Figure 29:
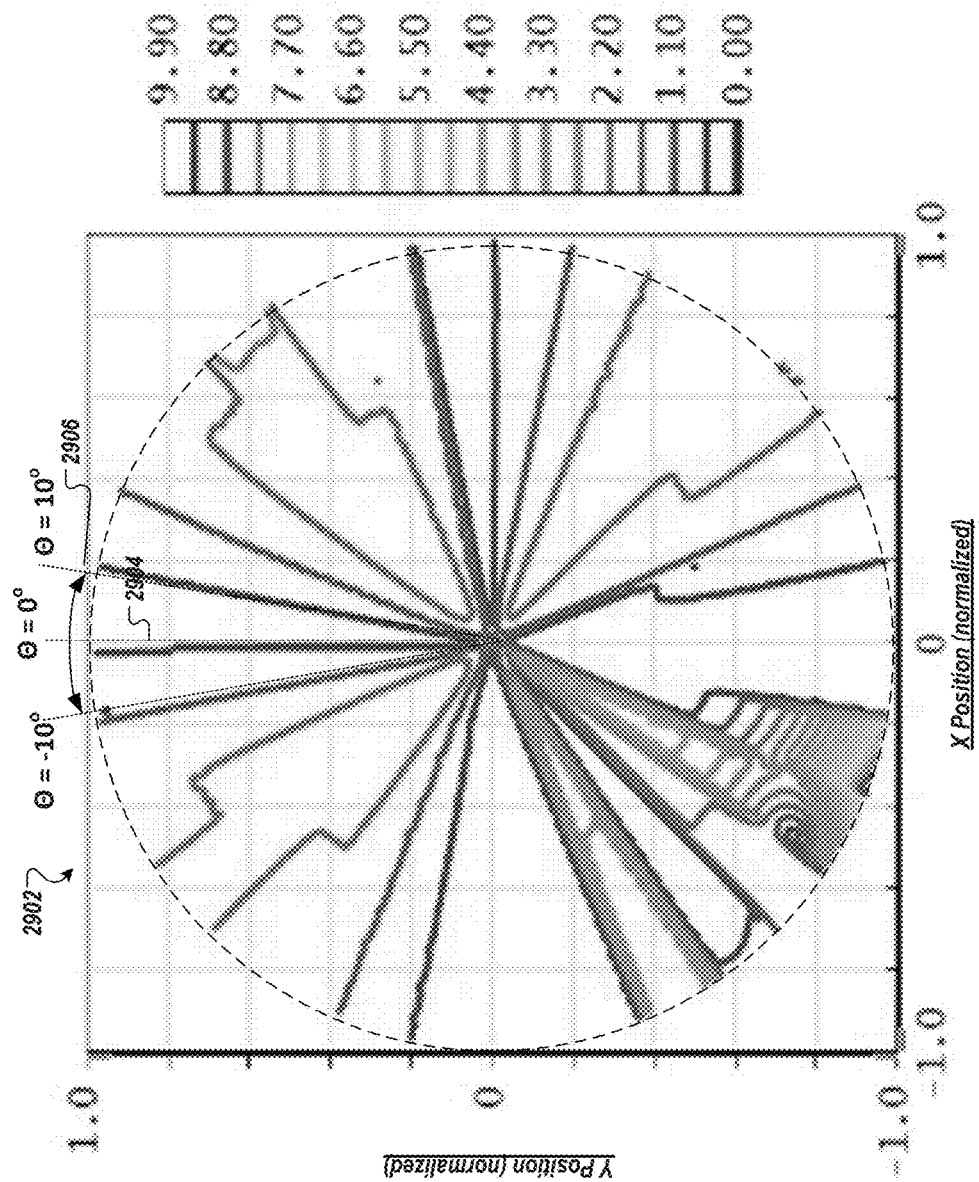
FIG. 29 is a diagram of cylindrical map of a polynomial surface that is uniformly arranged over a plurality of meridians that provides extended rotational tolerance, in accordance with an illustrative embodiment.

Ophthalmic Apparatus with Extended Tolerance Band by Modifying Refractive Powers in Uniform Meridian Distribution FIG. 29 is a diagram of cylindrical map of a polynomial surface 2902 (also referred to as an ETA polynomial surface 2902) that is uniformly arranged over a plurality of meridians that provides extended rotational tolerance, in accordance with an illustrative embodiment. The polynomial surface 2902 is mapped to a surface of an ophthalmic apparatus 324 (not shown—see FIG. 4) to provide cylinder power to the ophthalmic apparatus, e.g., for the correction an astigmatism, or the like, such that the ophthalmic apparatus can be subjected to a cylindrical axis misalignment (CAM) (shown via arrow 2904) of the meridian 2906a of up to 10 degrees without degradation of the corrective performance (e.g., with regard to visual acuity (VA) or modular transfer function (MTF)), as compared to when there no misalignment.

Notably, the polynomial surface 2902 is uniformly arranged, in this embodiment, over a plurality of meridians 2906 for every 0.5D (diopters). It should be appreciated that other values can be used. In some embodiments, the polynomial surface 2902 is uniformly arranged over a plurality of meridians 2906 for every 0.41D (diopters). In some embodiments, the polynomial surface 2902 is uniformly arranged over a plurality of meridians 2906 for every 0.42D (diopters). In some embodiments, the polynomial surface 2902 is uniformly arranged over a plurality of meridians 2906 for every 0.44D (diopters). In some embodiments, the polynomial surface 2902 is uniformly arranged over a plurality of meridians 2906 for every 0.46D (diopters). In some embodiments, the polynomial surface 2902 is uniformly arranged over a plurality of meridians 2906 for every 0.45D (diopters). In some embodiments, the polynomial surface 2902 is uniformly arranged over a plurality of meridians 2906 for every 0.48D (diopters). In some embodiments, the polynomial surface 2902 is uniformly arranged over a plurality of meridians 2906 for every 0.52D (diopters). In some embodiments, the polynomial surface 2902 is uniformly arranged over a plurality of meridians 2906 for every 0.54D (diopters). In some embodiments, the polynomial surface 2902 is uniformly arranged over a plurality of meridians 2906 for every 0.56D (diopters). In some embodiments, the polynomial surface 2902 is uniformly arranged over a plurality of meridians 2906 for every 0.58D (diopters). In some embodiments, the polynomial surface 2902 is uniformly arranged over a plurality of meridians 2906 for every 0.60D (diopters). The number of the added power at which the meridian are uniformly distributed is set at an individual eye's tolerance of meridian power change such as the astigmatic or cylinder power. This value changes individually, up to 1.0D (diopters), but on average a comfortable tolerance is about 0.5D at the IOL plane.

Figure 30:
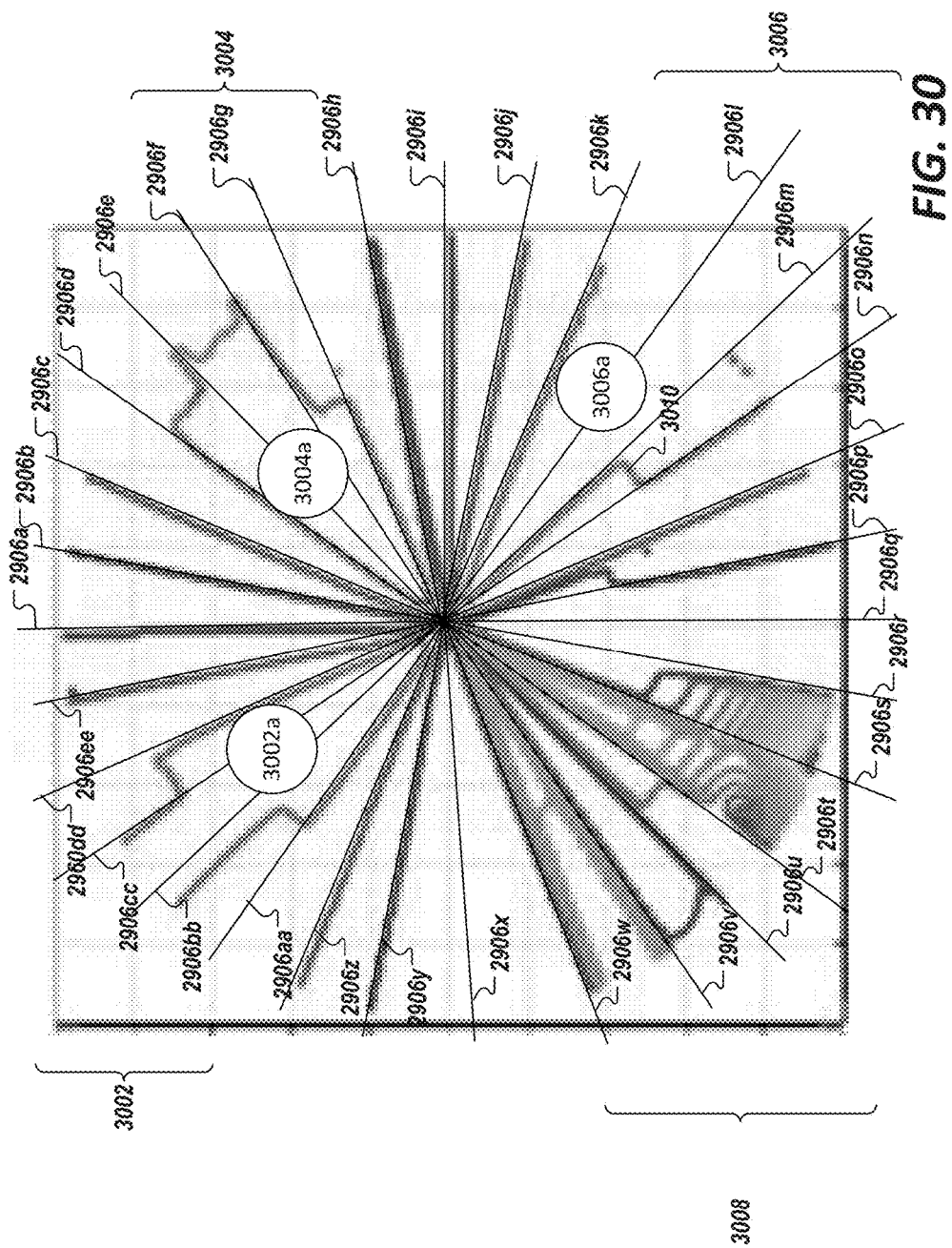
FIG. 30 is a diagram of the ETA polynomial surface of FIG. 29 shown with the plurality of uniformly arranged meridians, in accordance with an illustrative embodiment.

FIG. 30 is a diagram of the ETA polynomial surface 2902 of FIG. 29 shown with the plurality of uniformly arranged meridians 206 (shown as 2906a-2906ee), in accordance with an illustrative embodiment. As shown in FIG. 30 (and in FIG. 29), the ETA polynomial surface 2902, in this example, includes three regions 3002, 3004, 3006 (the center shown as 3002a, 3004a, and 3006a) of corrective cylindrical power—the first region 3002 spanning between meridians 2906aa and 2906dd; the second region 3004 spanning between meridians 2906d and 2906g; and the third region 3006 spanning between meridians 2906k and 2906n. As shown, each of the meridians (2906a-2906q and 2906x-2906a) are uniformly arranged (i.e., uniformly spaced at various angular positions—here about 11 degrees apart) for every 0.5D (diopters).

As shown in FIG. 30, meridian 2906a is located at about 90 degrees; meridian 2906b is located at about 79 degree; meridian 2906c is located at about 67 degree; meridian 2906d is located at about 55 degree; meridian 2906e is located at about 44 degree; meridian 2906f is located at about 33 degree; meridian 2906g is located at about 24 degree; meridian 2906h is located at about 11 degree; meridian 2906i is located at about 0 degree; meridian 2906j is located at about −12 degree; meridian 2906k is located at about −24 degree; meridian 29061 is located at about −36 degree; meridian 2906m is located at about −47 degree; meridian 2906n is located at about −56 degree; meridian 2906o is located at about −67 degree; meridian 2906p is located at about −79 degree; and meridian 2906q is located at about −90 degree; meridian 2906r is located at about −100 degree; meridian 2906s is located at about −112 degree; meridian 2906t is located at about −125 degree; meridian 2906u is located at about −135 degree; meridian 2906v is located at about −145 degree; meridian 2906w is located at about −158 degree; meridian 2906x is located at about −176 degree; meridian 2906y is located at about 168 degree; meridian 2906z is located at about 157 degree; meridian 2906aa is located at about 145 degree; meridian 2906bb is located at about 133 degree; meridian 2906cc is located at about 123 degree; meridian 2906dd is located at about 113 degree; and meridian 2906ee is located at about 101 degree.

It is contemplated that the ETA polynomial surface 102 may include more than three regions of corrective cylindrical power, e.g., a fourth region, a fifth region, and etc. In such embodiments, the regions between the corrective meridians may be uniformly reduced, e.g., to about 10 degrees apart, about 9 apart, about 8 degrees apart, about 7 degrees apart, and etc.

Table 1 illustrates examples of toric IOL designs with meridians uniformly distributed for a same added power, for a 0.25D same added power, for a 0.5D same added power, for a same 0.75D same added power, and for a same 1.0D same added power.

TABLE 1

| Added Power (in diopters) between each meridian | Max Added Power (diopters) | Number of meridians (from low to low power over ¼ of the lens) | Max number of corrective regions |
|---|---|---|---|
| 0.25 D | 4 D | 16 (4/0.25) | 6 |
| 0.5 D | 4 D | 8 (4/0.5) | 3 |
| 0.75 D | 4 D | 5.3 (4/0.75) | 3 |
| 1.0 D | 4 D | 4 (4/1) | 3 |

As shown in Table 1, when the meridians are uniformly arranged for a same added power of 0.5D, for a 4D base, there are 8 meridians between the high power meridian and the low power meridian in a quadrant of the polynomial surface between meridian 2906a and 2906i. This allows for up to 3 corrective regions on the polynomial surface, as shown in FIG. 30. In another embodiment, when the meridians are uniformly arranged for a same added power of 0.75D, for a 4D base, there are 5.4 meridians between the high power meridian and the lower power. This allows up to 3 corrective regions of the polynomial surface. In another embodiment, when the meridians are uniformly arranged for a same added power of 0.25D, for a 4D base, there are 16 meridians between the high power meridian and the lower power. This allows up to 6 corrective regions of the polynomial surface. In another embodiment, when the meridians are uniformly arranged for a same added power of 1.0, for a 4D base, there are 2 meridians between the high power meridian and the lower power. This allows up to 3 corrective regions of the polynomial surface, which has the high power meridian center located at meridians 2906e, 2906s, and 2906cc.

Figure 31:
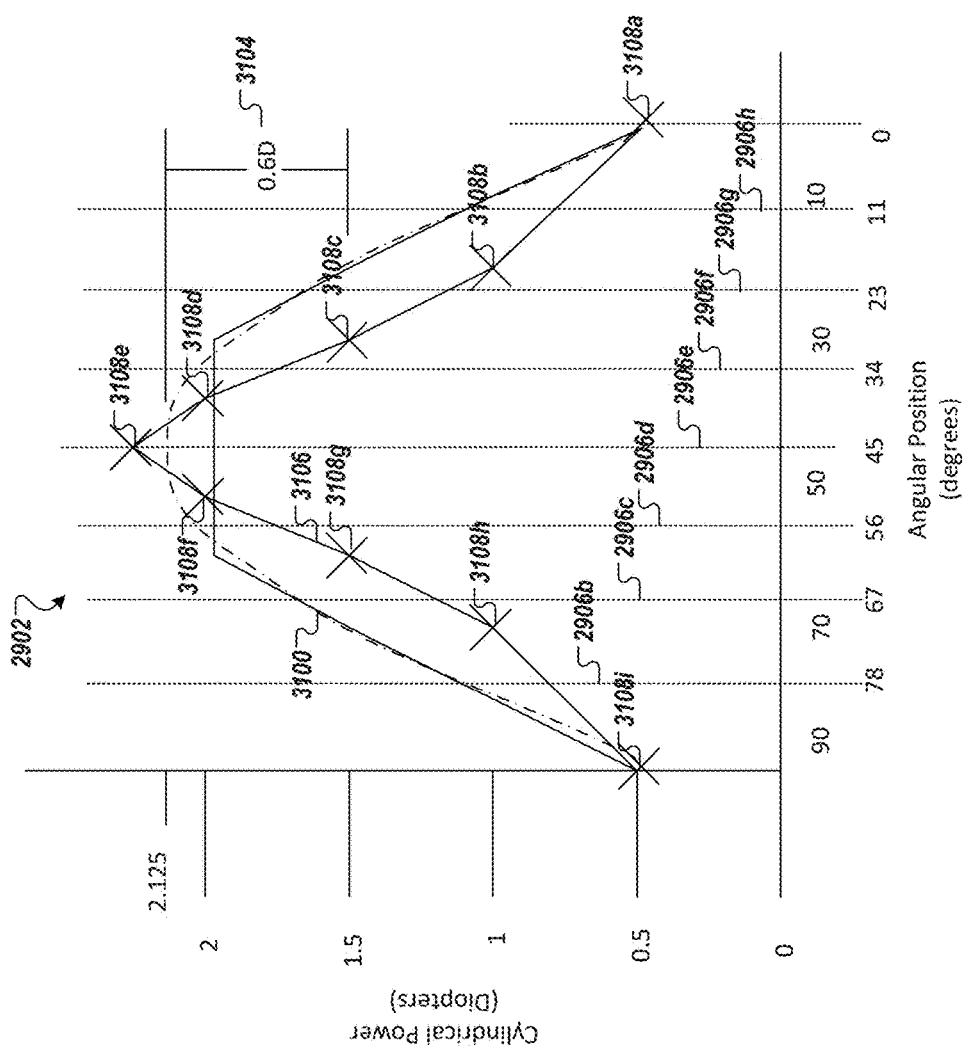
FIG. 31 is a profile of the polynomial surface of FIG. 29 with the plurality of uniformly arranged meridians, in accordance with an illustrative embodiment.

FIG. 31 is a profile of the polynomial surface of FIG. 29 with the plurality of uniformly arranged meridians, in accordance with an illustrative embodiment. As shown in FIG. 31, each meridian (e.g., 2906b, 2906c, 2906d, 2906e, 29060 is defined by an angular position that is uniformly arranged, about 11 degrees apart, for every 0.5D (diopters). In addition, the majority of meridian power change, from one meridian to the next, generates a change of more than 0.6D power difference (shown as 3104). The result is a profile that is more uniformly sloped that provided extended range of operation beyond about 5 degrees of misalignment (e.g., up to 10 degrees misalignment), as compared to a conventional or macro regular cylindrical surface with power changes according to COS(2*theta) trend, for a given difference between two meridians, shown as profile 3106. As shown in profile 3106, the meridian distribution is not uniform. Specifically, the meridian (in degrees) from the minimum power meridian—namely 0 degrees (3108a)—is located at a 20.7-degree position (3108b), a 30-degree position (3108c), a 37.8-degree position (3108d), a 45.0-degree position (3108e), a 52.2-degree position (31080, a 60-degree position (3108g), a 69.3-degree position (3108h), a 90.0-degree position (3108i), and etc., in a periodic trend, which provides a non-uniform meridian difference of about 20.7 degrees (between 3108a and 3108b), about 9.3 degrees (between 3108b and 3108c), about 7.8 degrees (between 3108c and 3108d), about 7.2 degrees (between 3108d and 3108e), about 7.2 degrees (between 3108e and 31080, about 7.8 degree (between 3108f and 3108g), about 9.3 (between 3108g and 3108h), and about 20.7 degree (between 3108h and 3108i).

Referring still to FIG. 31, off-center structures of the polynomial surface 2902 extend from the center structure in a gradually varying manner to apply cylinder power to a band of meridians surrounding the corrective meridian enabling the ophthalmic apparatus to operate off-axis (or off-meridian) to the corrective meridian (e.g., the astigmatism meridian). Notably, there are no more than 0.6-Diopter difference between any neighboring uniformly distributed contour lines.

In some embodiments, the polynomial surface 2902 is defined by a combination of spline or polynomial (e.g., a Zernike polynomial, a Chebyshev polynomial, or a combination of both) that is constrained by the condition of the meridians being uniformly arranged apart for a same given added diopter of power up to 1.0D (diopters).

Figure 32:
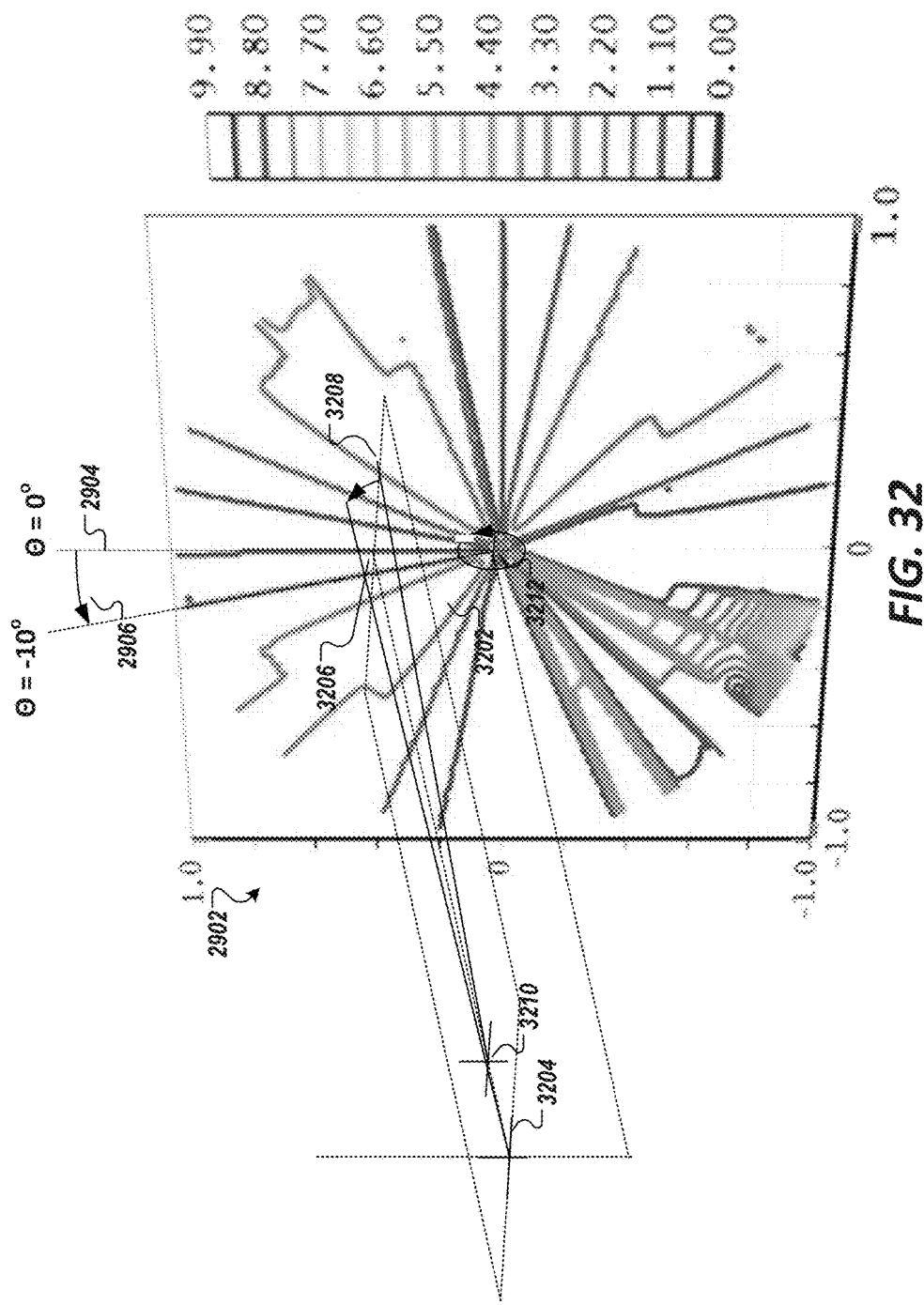
FIG. 32 illustrates an example operation of the polynomial surface of FIG. 29 when subjected to misalignment, in accordance with an illustrative embodiment.

FIG. 32 illustrates an example operation of the polynomial surface 2902 of FIG. 29 when subjected to misalignment, in accordance with an illustrative embodiment. The polynomial surface 2902, as a diffractive or refractive structure, in some embodiments, varies the extended depth of focus to a plurality of nearby focus points. To this end, light directed to such nearby focus points are thus directed to the desired focus point when the ophthalmic apparatus is subjected to a rotational offset from a primary intended axis of alignment, thereby extending the rotational tolerance of the apparatus to an extended tolerance band. In FIG. 32, a portion (3202) of the polynomial surface 2902 has a focus point 3204 (e.g., referred to as a "main focus point" 3204, e.g., to correct for an astigmatism) that is generated by a region about the center 3206 of the portion 3202 of the polynomial surface 2902. In this example, a nearby region 3208 of that portion 3202 has a focus point 3210 (e.g., referred to as an "auxiliary focus point" 3210) that is offset from the main focus point 3204. When the polynomial surface 2902 is rotated about axis 2912, e.g., as misalignment 2906 is introduced to the corrective meridian $\Theta=0°$ (2904), the focus point 3210 of region 3208 is moved towards the main focus point 3204, thereby extending the band of operation of the polynomial surface 2902. Remarkably, this extended tolerance astigmatism band delivers cylinder power to correct for the astigmatism for a range of meridians (e.g., up to $\pm 10°$ as shown in FIG. 29, though can be more in other embodiments), thereby eliminating any need for additional corrective measures (e.g., supplemental corrective devices or another surgical intervention) when the implanted ophthalmic apparatus is not perfectly aligned to the desired astigmatism meridian in the eye.

Put another way, the polynomial surface 2902 facilitates an extended band of the corrective meridian that has minimal, and/or clinically acceptable, degradation of the visual acuity and modulation transfer function when the ophthalmic apparatus is subjected to rotational misalignment between the astigmatic axis and a center axis of the corrective meridian.

Results of IOL with Exemplified Freeform-Polynomial Surfaces

Figure 33:
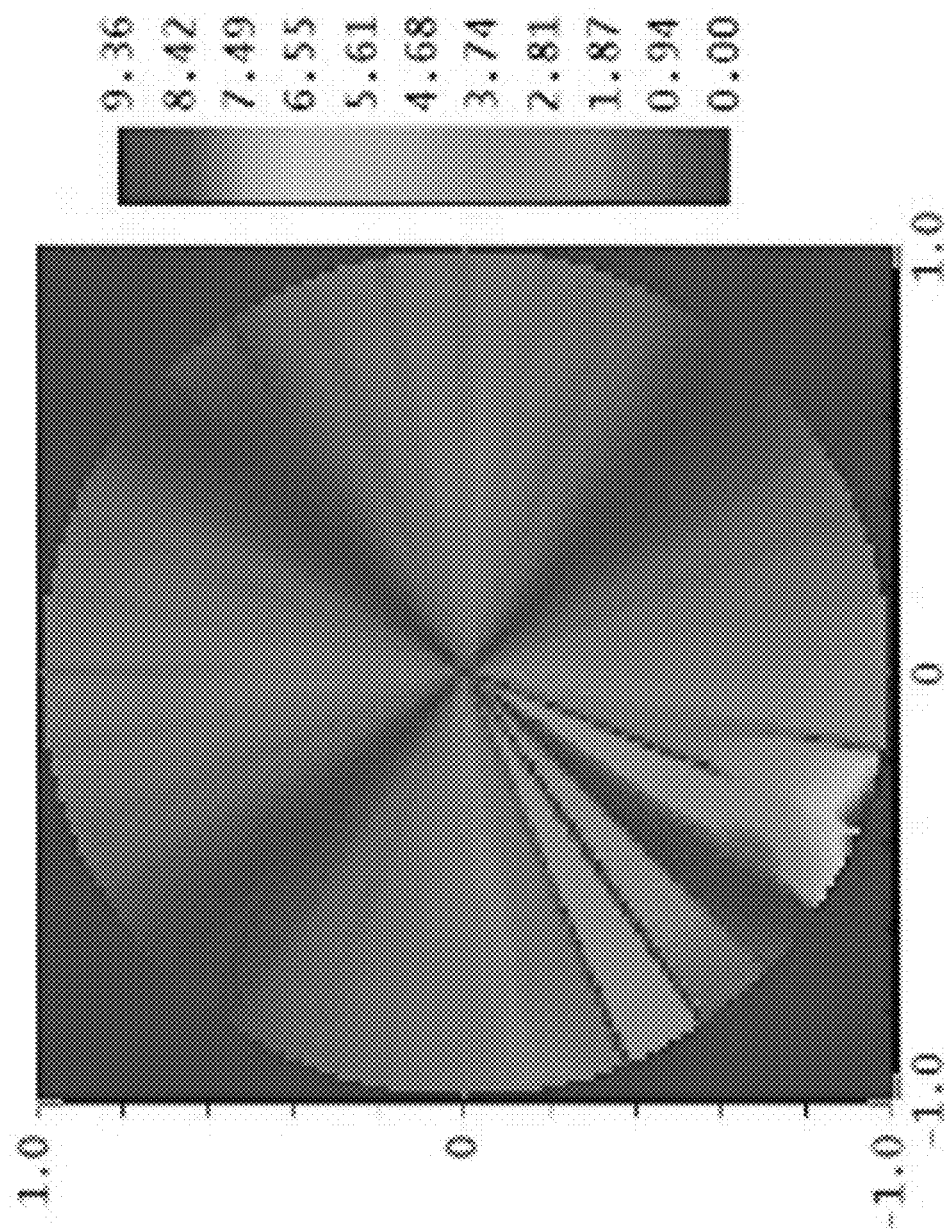
FIG. 33 shows a combined cylinder map generated from the combination of the IOL cylindrical power (provided, in part, via the polynomial surface) combined with the corneal cylindrical power through meridians.
Figure 34:
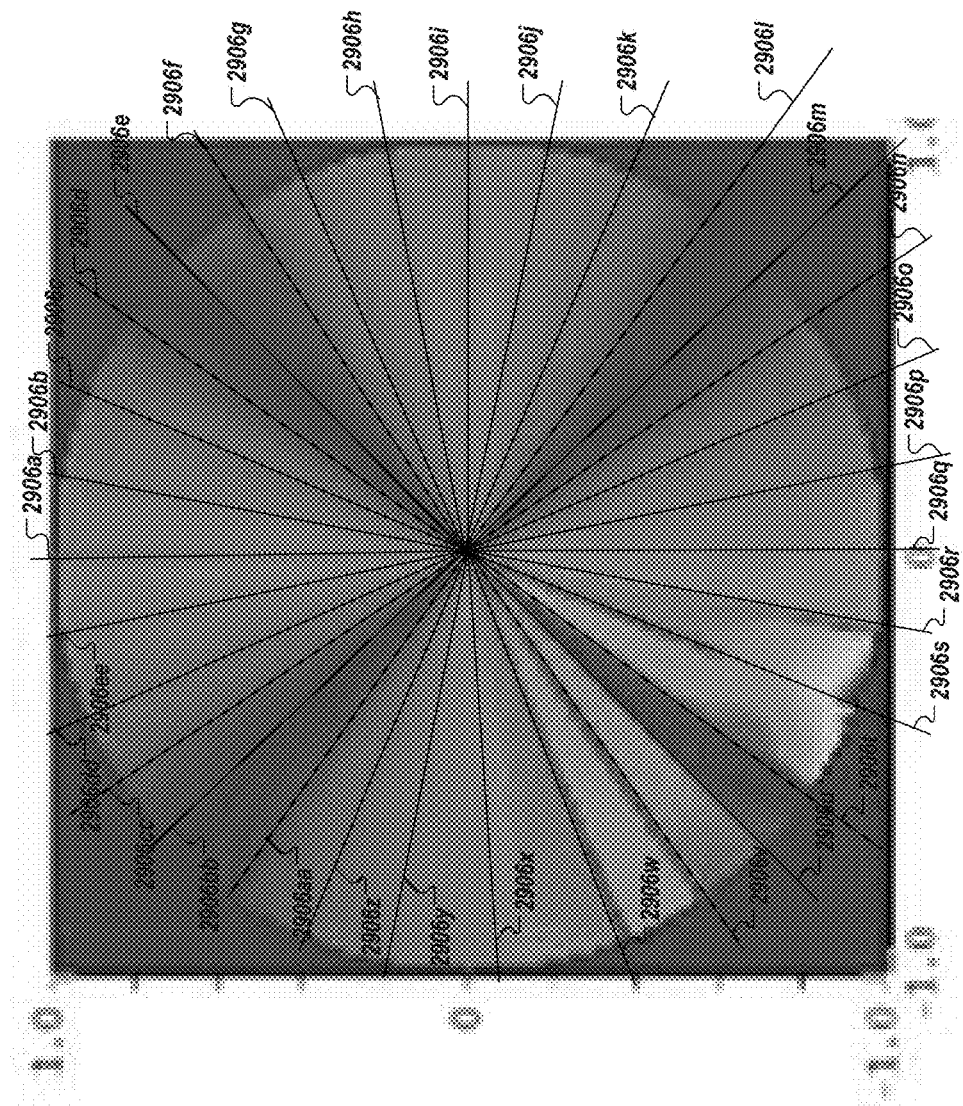
FIG. 34 shows the combined cylinder map of FIG. 33 with the meridians shown in FIG. 30 superimposed thereon.

FIG. 33 shows a combined cylinder map generated from the combination of the IOL cylindrical power (provided, in part, via the polynomial surface) combined with the corneal cylindrical power through meridians. FIG. 34 shows the combined cylinder map of FIG. 33 with the meridians shown in FIG. 30 superimposed thereon.

As discussed above with reference to FIG. 29, and as can be seen from the IOL cylinder map through meridians around the clock, there is remarkably no more than about 0.6D difference for any continuous uniformly distributed contour lines at the IOL plane. The IOL SE is 20D at the IOL plane. The IOL cylinder map of FIG. 29 is combined with the IOL SE to provide the overall IOL cylindrical map. That is, the astigmatism associated with test corneal cylindrical power has been attenuated and/or corrected for by the IOL cylindrical power provided, in part, by the polynomial surface.

Figure 35A:
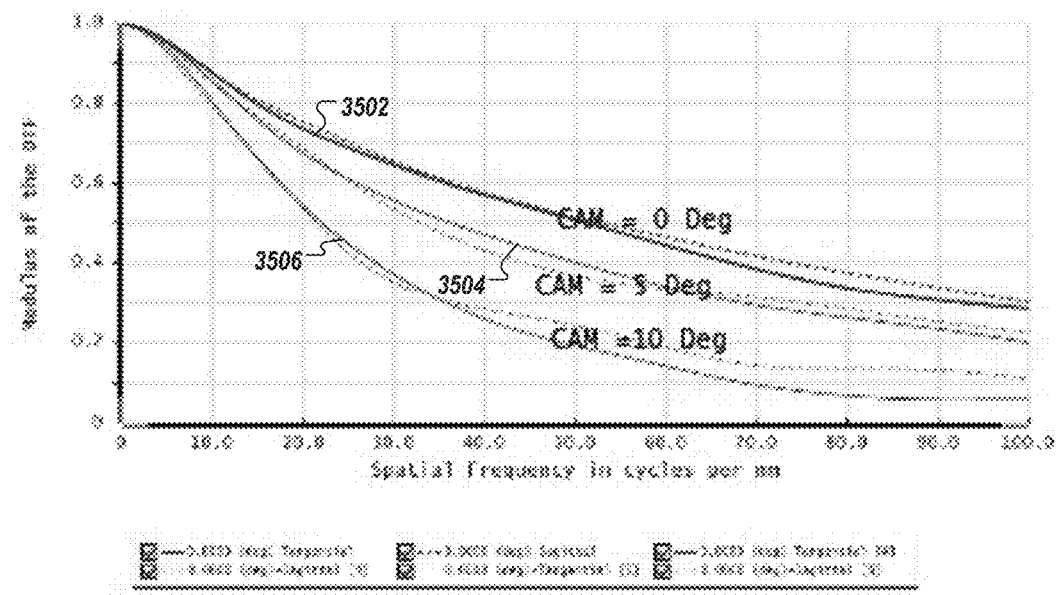
FIGS. 35A and 35B each shows calculated MTF values as spatial frequencies of an exemplified IOL 100 in a physiological eye model with astigmatic cornea in different cylindrical axis misalignment (CAM) situations between the cornea and the IOL for an iris pupil.
Figure 35B:
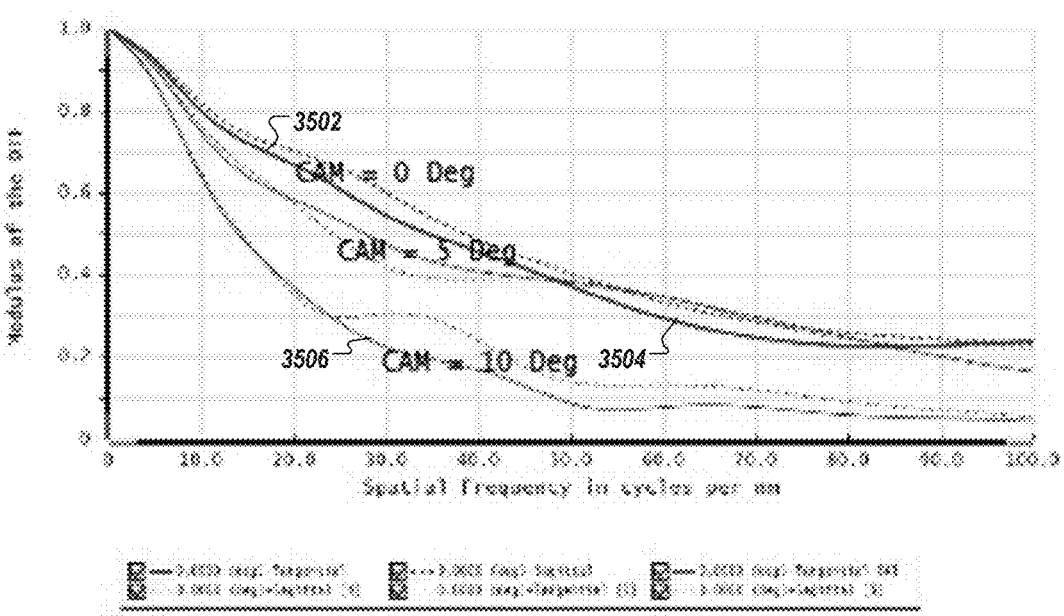

FIGS. 35A and 35B each shows calculated MTF values as spatial frequencies of an exemplified IOL 100 in a physiological eye model with astigmatic cornea in different cylindrical axis misalignment (CAM) situations between the cornea and the IOL for an iris pupil. Notably, as shown in FIGS. 35A and 35B, the modulation transfer function (MTF) is maintained across the extended range of alignment for a lens configured with the freeform-polynomial surface area 2902 of FIG. 29. Specifically, in FIGS. 35A and 35B, the MTFs for misalignment at 0 degrees, 5 degrees, and 10 degrees are shown (shown as "CAM=0 Deg" 3502, "CAM=5 Deg" 3504, and "CAM=10 Deg" 3506). In FIG. 35A, the iris pupil is about 3.0 mm. In FIG. 35B, the iris pupil is about 5.0 mm.

Notably, as can also be seen from the MTF curves, there are no cut-offs of the spatial frequency beyond 100 cpd (cycles per degree), which for an IOL with SE (Spherical Equivalent) of 20D (Diopters), this spatial frequency is approximately 30 cpd.

Corneal Irregular Geometry or Limited Retinal Area Functions

In another aspect, the polynomial surface 2902 of FIG. 29 is optimized to purposely place accumulated high surface amplitude (also referred to high order aberration) to non-functional retinal area so that the functional areas can fully benefit the ETA designs, that is, the enhanced image quality stability. Examples of non-functional retinal areas may include, but not limited to, areas of gradual loss of sight (e.g., associated with glaucoma or retinal macular degeneration (AMD).

Referring to FIG. 30, an accumulated high surface amplitude results at area 3008 to provide enhanced image quality stability for the three corrective regions 3002, 3004, 3006 that have uniform distributions discussed herein. In some embodiments, the corrective regions (e.g., 3002, 3004, 3006) effectively span over a region greater than 90 degrees to angular extent. Confined by a finite surface region, it is contemplated that the accumulated (high) surface amplitude area 3008 is purposely positioned (in a manner similar to the positioning of the corrective regions 3002, 3004, 3006) to coincide, e.g., with areas of limited retinal functionality that may be present with a given patient. That is, the accumulated (high) surface area is specifically optimized optically to target the special optical needs of the entire eye on this area.

Figure 36:
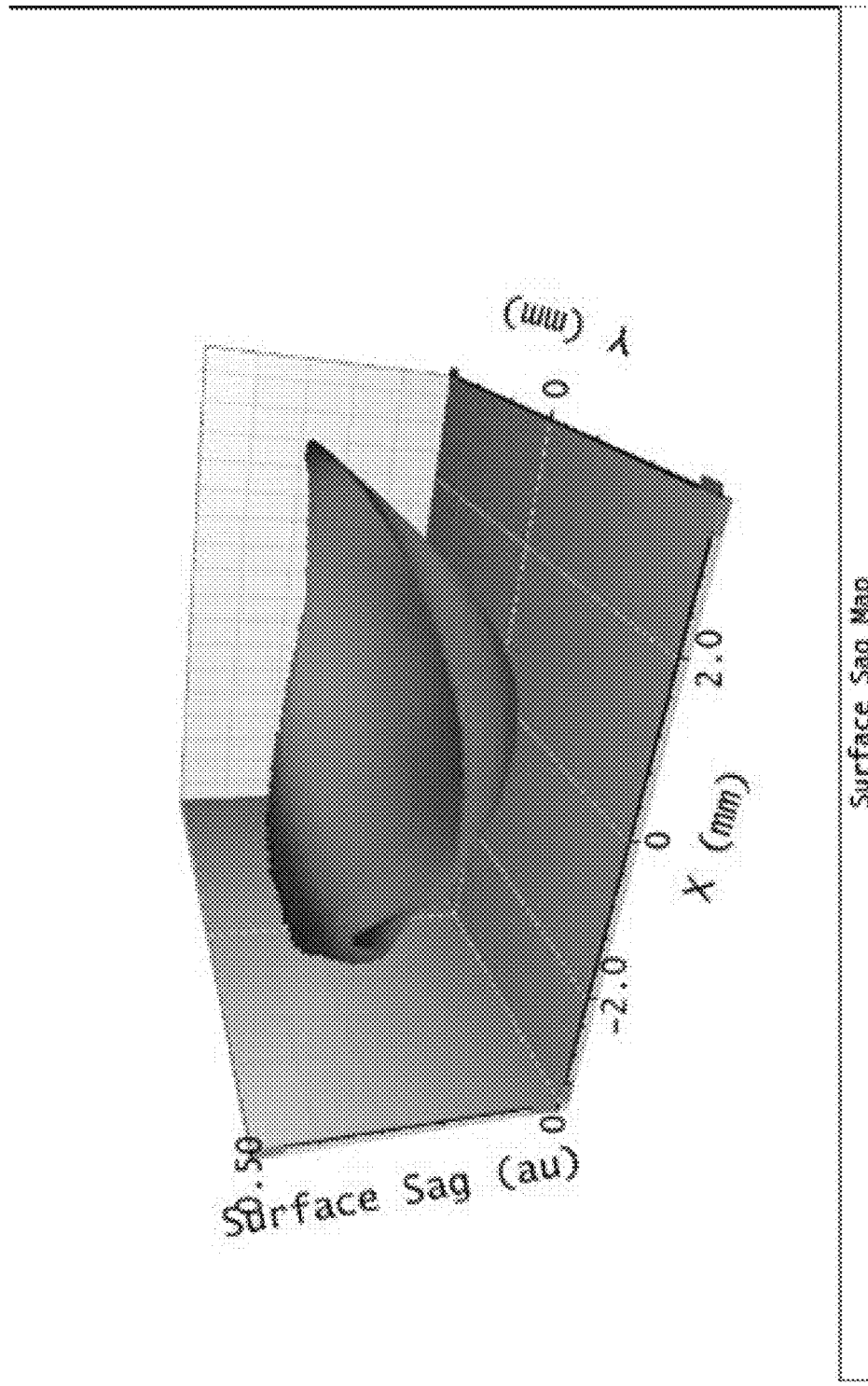
FIG. 36 is a surface SAG map of the polynomial surface 2902 of FIG. 29, in accordance with an illustrative embodiment.

FIG. 36 is a surface SAG map of the polynomial surface 2902 of FIG. 29, in accordance with an illustrative embodiment.

Referring back to FIG. 23, the diagram also shows a method to generate, via a processor, the polynomial surface of FIG. 29, in accordance with an illustrative embodiment. As shown in FIG. 23, the method includes generating (2302), via a processor, an initial freeform polynomial design (2304) comprising a base surface (with base cylindrical power) and sectional enhancements (with added cylindrical power in which each meridian is uniformly arranged for a same given added power) and iteratively generating (2306) and evaluating, a revised freeform polynomial design (1310), generated according to an optimization routine (2308) that is performed based on sectional parameters, until pre-defined image quality metric values and boundary parameter are achieved. The sectional enhancements power of the initial freeform polynomic design and the iterative freeform polynomic design are the ETA polynomial surface of FIG. 29.

The section surface optical parameters 1314 of the freeform polynomial surface, in some embodiments, includes parameters associated with sectional added power and meridian characteristics (shown as "Sectional add power" 1328) and parameters associated with high order aberration characteristics, e.g., Zernike aberrations above second-order (shown as "High order aberrations" 1328).

Referring still to FIG. 23, the parameters associated with the sectional added power 1326, in some embodiments, include a cylindrical power, for a given optical zone, for a same given added power in which meridians are uniformly arranged. In some embodiments, the cylindrical power for the added power are all refractive. The parameters associated with the high order aberration characteristics 1328, in some embodiments, include polynomial values (e.g., based on Zernike polynomials, Chebyshev polynomials, and combinations thereof) or characteristics such as polynomial orders and types as well as meridian boundaries for the high order aberrations. The high order aberration is constrained, e.g., from minimum to maximum cylindrical power over one or more meridian sections. In some embodiments, the high order aberrations is constrained or designated to a meridian, e.g., that corresponds to a corneal irregular geometry or limited retinal area functions. In such embodiments, the high order aberrations and its meridian locations on the lens surface may be optimized prior to the meridians for the uniform regions are determined to facilitate a customized design that is tailored for a given patient (i.e., particularly in view of corneal irregular geometry or limited retinal area functions). Such customization has a potential to truly benefit patients having cornea with or without astigmatism, patients with local Keratoconus with or without astigmatism, patients with glaucoma, patients with retinal macular degeneration (AMD), and the like.

Referring still to FIG. 23, the parameters associated with the pre-defined image quality metric value 1316 includes parameters associated with expected image quality metric (shown as "Expected image quality metric values" 1330) and parameters associated with special boundary restrain parameters (shown as "Special boundary restrain parameters" 1332). In some embodiments, image quality metric is based a comparison of a base polychromatic diffraction MTF (modular transfer function) (e.g., tangential and sagittal) to a number of error polychromatic diffraction MTFs values, e.g., where one or more polychromatic diffraction MTFs are determined for one or more misalignments of the generated toric lens from its intended operating meridians, e.g., at 5-degree misalignment and at 10-degree misalignment.

Referring still to FIG. 23, the initial design (1304) is evaluated (1334a) to determine image quality metric values (e.g., the base polychromatic diffraction MTF, e.g., at 0 degree misalignment) and the error polychromatic diffraction MTFs, e.g., at the 5 and 10 degrees misalignment) and boundary parameters, e.g., as shown in FIGS. 35A and 35B. The determined image quality metric values are evaluated (1336) to determine whether the image quality metric values and boundary parameters meet an expected outcome, e.g., a value of 0.2. In some embodiments, the expected outcome is whether there is no cut off through spatial frequency beyond 100 cpd. Upon determining that the condition is met, the method 1300 is stop (1338). It is contemplated that other image quality metrics may be used, e.g., the optical transfer function (OTF), phase transfer function (PhTF), and etc.

Where the condition is not met, the method 1300 adjusts (1308) sectional parameters to be optimized and rerun the optimization to generate the revised design 1310. The adjusted sectional parameters may include meridians locations and meridian spacing among neighboring meridians. The optimization may include allowing the uniform contour lines to move from one meridian to a next meridian up based on an upper limit amount and a lower limit amount. As shown in FIG. 30, the uniform contour line 3010 is show transitioning from meridian 2906m to meridian 2906n. The transition is constrained to occur along a specific radial position and without abrupt transition points.

Referring back to FIG. 23, the method 300 then includes evaluating (2334b) the revised design 2310 to determine image quality metric values (e.g., the base polychromatic diffraction MTF, e.g., at 0 degree misalignment) and the error polychromatic diffraction MTFs, e.g., at the 5 and 10 degrees misalignment) and boundary parameters, as discussed in relation to step 2334*a*, and re-evaluating (2336) whether the revised image quality metric values and boundary parameters meet the expected outcome, as discussed in relation to step 2336.

The present technology may be used, for example, in the Tecnis toric intraocular lens product line as manufactured by Abbott Medical Optics, Inc. (Santa Ana, Calif.).

It is not the intention to limit the disclosure to embodiments disclosed herein. Other embodiments may be used that are within the scope and spirit of the disclosure. In some embodiments, the above disclosed angularly varying phase members may be used for multifocal toric, extended range toric, and other categorized IOLs for extended tolerance of astigmatism caused by factors including the cylindrical axis misalignment. In addition, the above disclosed angularly varying phase members may be applied to spectacle, contact lens, corneal inlay, anterior chamber IOL, or any other visual device or system.

Exemplary Computer System

Figure 37:
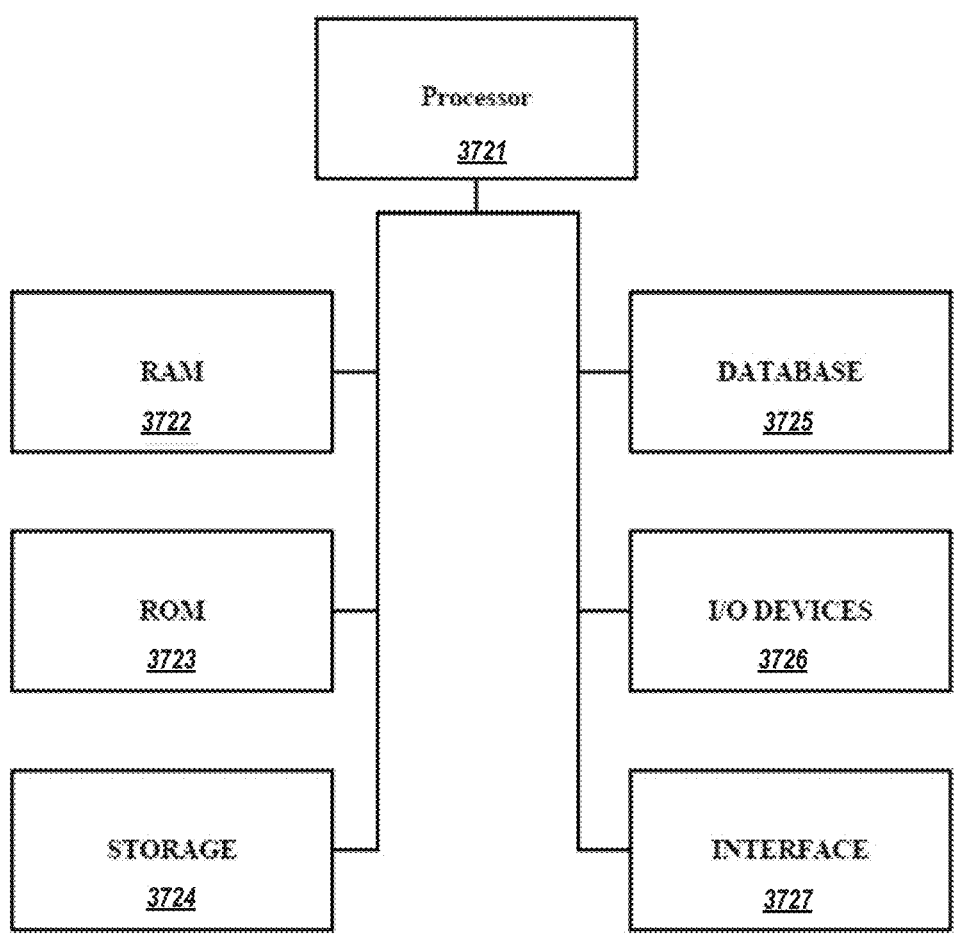
FIG. 37 is a diagram of an example computing device configured to generate the surface with the angularly-varying phase members.

FIG. 37 is a diagram of an example computing device configured to generate the surface with the angularly-varying phase members. As used herein, "computer" may include a plurality of computers. The computers may include one or more hardware components such as, for example, a processor 3721, a random access memory (RAM) module 3722, a read-only memory (ROM) module 3723, a storage 3724, a database 3725, one or more input/output (I/O) devices 3726, and an interface 3727. Alternatively and/or additionally, controller 3720 may include one or more software components such as, for example, a computer-readable medium including computer executable instructions for performing a method associated with the exemplary embodiments. It is contemplated that one or more of the hardware components listed above may be implemented using software. For example, storage 3724 may include a software partition associated with one or more other hardware components. It is understood that the components listed above are exemplary only and not intended to be limiting.

Processor 3721 may include one or more processors, each configured to execute instructions and process data to perform one or more functions associated with a computer for indexing images. Processor 3721 may be communicatively coupled to RAM 3722, ROM 3723, storage 3724, database 3725, I/O devices 3726, and interface 3727. Processor 3721 may be configured to execute sequences of computer program instructions to perform various processes. The computer program instructions may be loaded into RAM 3722 for execution by processor 3721. As used herein, processor refers to a physical hardware device that executes encoded instructions for performing functions on inputs and creating outputs.

RAM 3722 and ROM 3723 may each include one or more devices for storing information associated with operation of processor 3721. For example, ROM 3723 may include a memory device configured to access and store information associated with controller 3720, including information associated with IOL lenses and their parameters. RAM 3722 may include a memory device for storing data associated with one or more operations of processor 3721. For example, ROM 3723 may load instructions into RAM 3722 for execution by processor 3721.

Storage 3724 may include any type of mass storage device configured to store information that processor 3721 may need to perform processes consistent with the disclosed embodiments. For example, storage 3724 may include one or more magnetic and/or optical disk devices, such as hard drives, CD-ROMs, DVD-ROMs, or any other type of mass media device.

Database 3725 may include one or more software and/or hardware components that cooperate to store, organize, sort, filter, and/or arrange data used by controller 3720 and/or processor 3721. For example, database 3725 may store hardware and/or software configuration data associated with input-output hardware devices and controllers, as described herein. It is contemplated that database 3725 may store additional and/or different information than that listed above.

I/O devices 3726 may include one or more components configured to communicate information with a user associated with controller 3720. For example, I/O devices may include a console with an integrated keyboard and mouse to allow a user to maintain a database of images, update associations, and access digital content. I/O devices 3726 may also include a display including a graphical user interface (GUI) for outputting information on a monitor. I/O devices 3726 may also include peripheral devices such as, for example, a printer for printing information associated with controller 3720, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 3727 may include one or more components configured to transmit and receive data via a communication network, such as the Internet, a local area network, a workstation peer-to-peer network, a direct link network, a wireless network, or any other suitable communication platform. For example, interface 3727 may include one or more modulators, demodulators, multiplexers, demultiplexers, network communication devices, wireless devices, antennas, modems, and any other type of device configured to enable data communication via a communication network.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

What is claimed is:

1. A rotationally-tolerant intraocular lens (IOL), the intraocular lens comprising a multi-zonal optic body comprising one or more angularly-varying phase members that each includes an optimized combination of angularly and zonally diffractive phase structure located across one or more optical zones to apply power at one or more correcting meridian, wherein each of the one or more angularly-varying phase members applies the power at a given correcting meridian and vary an extended depth of focus to a plurality of nearby points of focus to provide an extended tolerance to misalignment of the intraocular lens when implanted in an eye, the multi-zonal optic body forming a first angularly-varying phase member having a peak cylinder power centered at a first correcting meridian, the first angularly-varying phase member at the peak cylinder power being configured to direct light, at the first correcting meridian, to a first point of focus on the retina, wherein at angular positions nearby to the first correcting meridian, the angularly-varying phase member varies, at each optical zone, and is configured to direct light to points of focus nearby to the first point of focus such that the multi-zonal optic body, when rotational offset from the peak cylinder power, directs light from the nearby points of focus to the first point of focus, thereby establishing an extended band of operational meridians over the first correcting meridian, wherein each phase structure has a height profile at a face of the multi-zonal optic body that varies along the extended band of operational meridians over each respective corrective meridian.

2. The intraocular lens of claim 1, wherein the multi-zonal lens body forms the angularly-varying phase member, wherein a height profile $T1(r, \theta)$ for each meridian $\theta$ is defined as:

$$T1(r,\theta)=t_1(r)|COS^2(\theta)|+t_2(r)|SIN^2(\theta)|$$

where $t_1(r)$ and $t_2(r)$ are the added power for each zone.

3. The intraocular lens of claim 2, wherein the multi-zonal lens body comprises at least four optical zones, the at least four optical zones forming an angularly varying efficiency quadric optics.

4. The intraocular lens of claim 3, wherein the angularly-varying phase members, collectively, form a pattern that is expressed as $$r(\theta) = \sqrt{2 \cdot n \cdot \frac{s(\theta) \cdot \lambda}{A(\theta)}},$$

where $r(\theta)$ is the contour radius for the given meridian added power $A(\theta)$, wavelength $\lambda$, zone number n, and the scaling value $s(\theta)$, all at meridian $\theta$.

5. The intraocular lens of claim 1, wherein the angularly-varying phase member spans an optical zone defined by a polynomial-based surface coincident at a plurality of meridians having distinct cylinder powers, wherein each of the plurality of meridians is uniformly arranged on the optical zone for a same given added diopter of power up to 1.0D.

6. The intraocular lens of claim 5, wherein differences among each continuously uniformly distributed contour line, at a given IOL plane, associated with a given meridian of the plurality of meridians is less than about 0.6D (diopters).

7. The intraocular lens of claim 5, wherein the polynomial-based surface is characterized by a series of weighted cosine-based functions.

8. The intraocular lens of claim 1, wherein the one or more angularly-varying phase members each spans a first optical zone defined by a freeform-polynomial surface area coincident with one or more distinct cylinder powers, wherein the freeform-polynomial surface area is defined as a mathematical expression comprising a combination of one or more polynomial expressions each having a distinct complex orders.

9. The intraocular lens of claim 8, wherein at least one of the one or more polynomial expressions are selected from the group consisting of a Chebyshev polynomial and a Zernike polynomial.

10. The intraocular lens of claim 8, wherein the freeform-polynomial surface area establishes the extended band of operational meridian across a range selected from the group consisting of about ±4 degrees, about ±5 degrees, about ±6 degrees, about ±7 degrees, about ±8 degrees, about ±9 degrees, about ±10 degrees, about ±11 degrees, about ±12 degrees, about ±13, degrees, about ±14 degrees, and about ±15 degrees.

11. The intraocular lens of claim 8, wherein the freeform-polynomial surface area has a second height profile $T(x,y)$ on a first base height profile, the second height profile being defined as:

$$T(x,y)=\Sigma\{c(i,j)*\cos(i*\arccos(t))*\cos(j*\arccos(t))\}$$

where c(i, j) is a coefficient based on i and j, which are each integers, x and y are spatial locations on the freeform-polynomial surface area, and t is a normalized parameter having values between −1.0 and 1.0.

12. The intraocular lens of claim 11, wherein the coefficients $c(i,j)$ or $c_2(i_2, j_2)$ are a function of local coordinates that puts accumulated high surface amplitude to area of non-functional retinal area.

13. The intraocular lens of claim 11, wherein the coefficients $c(i,j)$ or $c_2(i_2, j_2)$ are a function of local coordinates that accounts for irregular corneal shape.

14. The intraocular lens of claim 8, wherein the one or more optical zones includes the first optical zone and a second optical zone, wherein the second optical zone is defined by a second freeform-polynomial surface region characterized and defined by a second polynomial, wherein the second freeform-polynomial surface area has a third height profile $T_2(x,y)$ superimposed on a first height profile (e.g. a base or typical aspheric height profile), the third height profile being defined as:

$$T_2(x,y)=\Sigma\{c_2(i_2,j_2)*\cos(i_2*\arccos(t_2))*\cos(j_2*\arccos(t_2))\}$$

where $c_2(i, j)$ is a coefficient based on $i_2$ and $j_2$, which are each integers, x and y are spatial locations on the second freeform-polynomial surface area and has values between −1.0 and 1.0, and $t_2$ is a normalized parameter having values between −1.0 and 1.0.

15. The intraocular lens of claim 14, wherein the first freeform-polynomial surface area and the second freeform-polynomial surface area each comprises a monofocal lens, a bifocal lens, a multi-focal lens, or an extended range of vision lens.

16. The intraocular lens of claim 1, wherein the angularly-varying phase member is formed of a refractive structure.

17. The intraocular lens of claim 1, wherein the angularly-varying phase member is formed of a diffractive structure.

18. The intraocular lens of claim 1, wherein an offset of each meridian of the plurality of meridians of about 10 degrees causes a MTF (modulation transfer function) measure change of less than 10% at 30 cycles per degree (cpd).

19. The intraocular lens of claim 1, wherein the multi-zonal optic body forms a a second angularly-varying phase member having a second peak cylindrical power centered at a second correcting meridian, the second angularly-varying phase member at the second peak cylinder power being configured to direct light to a second point of focus on the retina, wherein at angular positions nearby to the first meridian, wherein the second angularly-varying phase member varies along meridian nearby to the second point of focus such that the multi-zonal optic body, when rotational offset from the second peak cylinder power, directs light from the nearby points of focus to the second point of focus.

20. The intraocular lens of claim 1, wherein the intraocular lens comprises an intraocular toric lens.

* * * * *